US007264970B2

(12) United States Patent
Chandler et al.

(10) Patent No.: US 7,264,970 B2
(45) Date of Patent: Sep. 4, 2007

(54) GENETIC FUNCTIONS REQUIRED FOR GENE SILENCING IN MAIZE

(75) Inventors: Vicki L. Chandler, Tucson, AZ (US); Jay B. Hollick, Berkeley, CA (US); Jane E. Dorweiler, Tucson, AZ (US); Damon Lisch, Albany, CA (US); Ken Kubo, Sacramento, CA (US); Charles Carey, Scottsdale, AZ (US)

(73) Assignees: Regents of the University of California, Oakland, CA (US); University of Oregon, Eugene, OR (US); University of Arizona, Tucson, AZ (US)

( * ) Notice: Subject to any disclaimer, the term of this patent is extended or adjusted under 35 U.S.C. 154(b) by 1034 days.

(21) Appl. No.: 09/972,805

(22) Filed: Oct. 5, 2001

(65) Prior Publication Data

US 2002/0157133 A1    Oct. 24, 2002

Related U.S. Application Data

(60) Provisional application No. 60/238,137, filed on Oct. 5, 2000.

(51) Int. Cl.
*C12N 15/82* (2006.01)
*C12N 5/14* (2006.01)
*A01H 1/00* (2006.01)
*A01H 5/10* (2006.01)
*A01H 5/00* (2006.01)

(52) U.S. Cl. .................. 435/468; 435/412; 435/419; 435/430.1; 800/266; 800/275; 800/298; 800/320.1

(58) Field of Classification Search ............... 435/410, 435/412, 419, 424, 430.1, 468; 800/260, 800/266, 268, 275, 278, 295, 298, 320.1
See application file for complete search history.

(56) References Cited

FOREIGN PATENT DOCUMENTS

WO    WO99/58659    11/1999

OTHER PUBLICATIONS

Chandler et al., Nature Rev. Genet., 2004, vol. 5, pp. 532-544.*
De Wilde, Chris et al. (2000) "Plants as bioreactors for protein production: Avoiding the problem of transgene silencing" *Plant Molecular Biology* 43 (2-3): 347-359.
Lakshminarayan, Iyer M. et al. (2000) "Transgene silencing in monocots" *Plant Molecular Biology* 43 (2-3): 323-346.
Scheid, Ortrun Mittelsten et al. (2000) "Transcriptional gene silencin mutants" *Plant Molecular Biology* 43 (2-3): 235-241.
Walbot, Virginia (2001) "Imprinting of R-r paramutation of B-I and P1, and epigenetic silencing of MuDR/Mu transposons in Zea mays L. are coordinately affected by inbred background" *Genetical Research* 77 (3): 219-226.

Amedeo, P. et al., "Distruption of the plant gene *MOM* releases transcriptional silencing of methylated genes" *Nature* 405 (2000): 203-206.
Chandler, V. L. "Paramutation: Allelic Interactions that Cause Heritable Changes in Transcription", *Molecular Biology Meeting (Abstract)*, Queenstown, New Zealand (Aug. 1998).
Chandler, V. L. "Epigenetic Control of Gene Expression in Plants", *Symposium: Plant Physiology 2000 and Beyond: Breaking the Mold (Abstract #30002)*, Providence, Rhode Island (Jul. 23, 2001).
Chandler, V. L. and K. J. Hardeman. "The *Mu* Elements of *Zea mays*" *Adv. Genetics* 30 (1992): 77-122.
Chandler, V. L. and H. Vaucheret. "Gene Activation and Gene Silencing" *Plant Physiol.* 125 (2001): 145-8.
Chandler, V. L. and V. Walbot, "DNA modification of a maize transposable element correlates with loss of activity" *Proc. Natl. Acad. Sci. USA* 83 (1986): 1767-71.
Chandler, V. L. et al., "Paramutation: Allelic Interactions that Cause Heritable Changes in Transcription", *Abstracts of papers presented at the EMBO Workshop on "Chromatin and Epigenetic Regulation"*, Heidelberg (Oct. 4-7, 1997): 41.
Chandler, V. L. et al. "Paramutation in maize" *Plant Mol. Biol.* 43 (2000): 121-145.
Chandler, V. L. et al., "*b* and *pl* Paramutation in Maize: Heritable Transcription States Programmed during Development", *Epigenetic Mechanisms of Gene Regulation*, V.E.A. Russo et al. eds. (New York: Cold Spring Harbor Laboratory Press) (1996): 389-390.
Chandler, V. L. et al. "Mutants that prevent paramutation also affect other types of epigenetic silencing" *46th International NIBB Conference, Genetics & Epigenetics, 1st 100 years*: Mar. 6-10, 2001, Abstract.
Chomet, P. et al. "Identification of a Regulator Transposon That Controls the *Mutator* Transposable Element System in Maize" *Genetics* 129 (1991): 261-70.
Cogoni, C. and G. Macino. "Isolation of quelling-defective (*qde*) mutants impaired in posttranscriptional transgene-induced gene silencing in *Neurospora crassa*" *Proc. Natl. Acad. Sci. USA* 94 (1997): 10233-10238.
Dalmay, T. et al. "An RNA-Dependent RNA Polymerase Gene in *Arabidopsis* is Required for Posttranscriptional Gene Silencing Mediated by a Transgene but Not by a Virus" *Cell* 101 (2000): 543-553.
Dalmay, T. et al. "SDE3 encodes an RNA helicase required for post-transcriptional gene silcening in *Arabidopsis*" *EMBO J.* 20 (2000): 2069-2077.
Dorweiler, J. E. et al. "Analysis of Paramutation at the *b* Locus of Maize" *39th Annual Maize Genetics Conference Program and Abstracts*, Clearwater Beach, FL (Mar. 13-16, 1997): 36.

(Continued)

*Primary Examiner*—Ashwin Mehta
(74) *Attorney, Agent, or Firm*—Morrison & Foerster LLP

(57) ABSTRACT

Transgenic silencing is a little understood process by which genes introduced into plants are turned off or silenced. Genetic screens were designed to identify corn mutants with reduced gene silencing activity. Such mutant corn lines include Mop1-1; Mop1-2EMS; Mop2-1, mop3-1; CC2343, rmr1-1; rmr1-2; rmr2-1; rmr6-1; rmr7-1; rmr7-2; rmr8-1; rmr9-1; Mop1-4; Mop1-5; and rmr11-1 and seeds derived therefrom, the plants are useful for corn breeding programs to produce inbred and hybrid seed with reduced gene silencing activity.

57 Claims, 32 Drawing Sheets
(11 of 32 Drawing Sheet(s) Filed in Color)

OTHER PUBLICATIONS

Dorweiler, J. E. et al. "Mutations that Affect Paramutation and Correlations with Chromatin Structure" *40th Annual Maize Genetics Conference Program and Abstracts*, Lake Geneva, WI (Mar. 19-22, 1998): 7.

Dorweiler, J. E. et al. "*Mediator of Paramutation2* is a dominant inhibitor of the establishment of paramutation" *42nd Annual Maize Genetics Conference Program and Abstracts*, Coure D'Alene, ID (Mar. 16-19, 2000): 97.

Dorweiler, J. E. et al. "*mediator of paramutation1* Is Required for Establishment and Maintenance of Paramutation at Multiple Maize Loci" *Plant Cell* 12 (2000): 2101-2118.

Fagard, M. et al. "AGO1, QDE-2, and RDE-1 are related proteins required for post-transcruptional gene silencing in plants, quelling in fungi, and RNA interference in animals" *Proc. Natl. Acad. Sci. USA* 97 (2000): 11650-11654.

Fagard, M. and H. Vaucheret. "(Trans)Gene Silencing in Plants: How Many Mechanims?" *Annu. Rev. Plant Physiol. Plant Mol. Biol.* 51 (2000):167-194.u Finnegan, E. J. et al. "Reduced DNA methylation in *Arabidopsis thaliana* results in abnormal plant development" *Proc. Natl. Acad. Sci. USA* 93 (1996): 8449-8454.

Furner, I. J. et al. "Gene Silencing and Homology-Dependent Gene Silencing in Arabidopsis: Genetic Modifiers and DNA Methylation" *Genetics* 149 (1998): 651-662.

Gibbons, R. J. et al. "Mutations in *ATRX*, encoding a SWI/SNF-like protein, cause diverse changes in the pattern of DNA methylation" *Nat. Genet.* 24 (2000): 368-371.

Goff, S. A. et al. "Functional analysis of the transcriptional activator encoded by the maize B gene: evidence for a direct functional interaction between two classes of regulatory proteins" *Genes & Dev.* 6(1992): 864-875.

Goff, S. A. et al. "Transactivation of anthocyanin biosynthetic genes following transfer of *B* regulatory genes into maize tissues" *EMBO J.* 9 (1990): 2517-2522.

Henikoff, S. and L. Comai, "*Trans*-Sensing Effects: The Ups and Downs of Being Together" *Cell* 93 (1998): 329-332.

Hollick, J. B. "The *rmr6* locus affects *pl* paramutation and plant development" *41st Annual Maize Genetics Conference Program and Abstracts*, Lake Geneva, WI, (Mar. 11-14, 1999): 56.

Hollick, J. B. "Genetic components required for paramutation at the p11 locus" *43rd Annual Maize Genetics Conference Program and Abstracts*, Lake Geneva, WI (Mar. 14-18, 2001): 86.

Hollick, J. B. and V. L. Chandler, "Genetic Factors Required to Maintain Repression of a Paramutagenic Mazie *pl1* Allele" *Genetics* 157 (2001): 369-378.

Hollick, J. B. and V. L. Chandler, "Epigenetic Allelic States of a Maize Transcriptional Regulatory Locus Exhibit Overdominant Gene Action" *Genetics* 150 (1998): 891-897.

Hollick, J. B. and V. L. Chandler, "Genetic Factors Affecting Paramutant *pl* Alleles" *39th Annual Maize Genetics Conference Program and Abstracts*, Clearwater Beach, FL (Mar. 13-16, 1997): 37.

Hollick, J. B. and V. L. Chandler, "Genetic Requirements for the Heritable Suppression of a Paramutable pl Allele" *40th Annual Maize Genetics Conference Program and Abstracts*, Lake Geneva, WI (Mar. 19-22, 1997): 7.

Hollick, J. B. and M. P. Gordon, "A poplar treee proteinase inhibitor-like gene promoter is responsive to wounding in transgenic tobacco" *Plant Mol. Biol.* 22 (1993): 561-572.

Hollick, J. B. and D. Lisch. "Diverse roles of required to maintain repression (rmr) factors in gene silencing" *42nd Annual Maize Genetics Conference Program and Abstracts*, Coure D'Alene (Mar. 16-19, 2000): 32.

Hollick, J. B. et al. "Paramutation and related allelic interactions" *Trends Genet.* 13 (1997): 302-308.

Hollick, J. B. et al. "Paramutation Alters Regulatory Control of the Maize *pl* Locus" *Genetics* 154 (2000): 1827-1838.

Hollick, J. B. et al. "Allelic Interactions Heritably Alter the Activity of a Metastable Maize *pl* Allele" *Genetics* 141 (1995): 709-719.

Holliday, R. et al. "Gene Silencing in Mammalian Cells", *Epigenetic Mechanisms of Gene Regulation*, V.E.A. Russo et al. eds. (New York: Cold Spring Harbor Laboratory Press) (1996): 47-59.

Jeddeloh, J.A. et la., "Maintenance of genomic methylation requires a SWI2/SNF2-like protein" *Nature Genet.* 22 (1999):94-97.

Jones, L. et al. "RNA-directed transcriptional gene silencing in plants can be inherited independently of the RNA trigger and requires Met1 for maintenance" *Curr. Biol*, 11 (2001): 747-757.

Jorgensen, R. A. "Cosuppression, Flower Color Patterns, and Metastable Gene Expression States" *Science* 268 (1995): 686-691.

Kakutani, T. et al. "Development abnormalities and epimutations associated with DNA hypomethylation mutations" *Proc. Natl. Acad. Sci. USA* 93 (1996): 12406-12411.

Kakutani, T. et al. "Meiotically and Mitotically Stable Inheritance of DNA Hypomethylation Induced by *ddm1* Mutation of *Arabidopsis thaliana*" *Genetics* 151 (1999): 831-838.

Lisch, D. et al. "Genetic Characterization of the *Mutator* System in Maize: Behavior and Regulation of *Mu* Transposons in a Minimal Line" *Genetics* 139 (1995): 1777-96.

Lisch, D. et al. "Mutations that Affect Paramutations also Reverse Mu element Methylation" *42nd Annual Maize Genetics Conference Program and Abstracts*, Coure D'Alene, ID (Mar. 16-19, 2000); 21.

Lisch, D. and M. Freeling, "Loss of Mutator Activity in a Minimal Line¹" *Maydica* 39 (1994): 289-300.

Martienssen, R. A. "Epigenetic Silencing of Mu Transposable Elements in Maize", *Epigenetic Mechanisms of Gene Regulation*, Russo, V.E.A. et al. eds. (New York: Cold Spring Harbor Laboratory Press) (1996): 593-608.

Matzke, M. A. et al. "Paramutation and transgene silencing: a common response to invasive DNA?" *Trends Plant Sci.* 1 (1996): 382-388.

Mittelsten Scheid, O. et al. "Release of epigenetic gene silencing by trans-acting mutations in *Arabidopsis*" *Proc. Natl. Acad. Sci. USA* 95 (1998): 632-637.

Morel, J. B. and H. Vaucheret. "Post-transciptional gene silencing mutants" *Plant Mol. Biol.* 43 (2000): 275-284.

Mourrain, P. et al. "*Arabidopsis* SGS2 and SGS3 Genes Are Required for Posttranscriptional Gene Silencing and Natural Virus Resistance" *Cell* 101 (2000): 533-542.

Patterson, G. I. et al. "Genetic Analysis of *B-Peru*, a Regulatory Gene in Maize" *Genetics* 126 (1991): 205-220.

Patterson, G. I. et al. "Sequences Required for Paramutation of the Maize *b* Gene Map to a Region Containing the Promoter and Upstream Sequences" *Genetics* 140 (1995): 1389-1406.

Patterson, G. I. et al. "Paramutation, an Allelic Interaction, Is Associated With a Stable and Heritable Reduction of Transcription of the Maize *b* Regulatory Gene" *Genetics* 135 (1993): 881-894.

Radicella, J. P. et al. "Allelic diversity of the maize *B* regulatory gene: different leader and promoter sequences of two *B* alleles determine distinct tissue specificties of anthocynanin production" *Genes & Development* 6 (1992): 2152-2164.

Radicella, J. P. et al. "Cloning and nucleotide sequence of a cDNA encoding B-Peru, a regulatory protein of the anthocyanin pathway in maize" *Plant Mol. Biol.* 17 (1991): 127-130.

Selinger, D. A. and V. L. Chandler, "*B-Bolivia*, an allele of the Maize *b1* Gene with Variable Expression, Contains a High Copy Retrotransposon-Related Sequence Immediately Upstream" *Plant Physiol.* 125 (2001): 1363-79.

Selinger, D. A. and V. L. Chandler, "Characterization of a tissue-specific gene silencing phenomenon involving *B-Bolivia* and CaMV 35S/B chimeric transgenes" *42nd Annual Maize Genetics Conference Program and Abstracts*, Coure D'Alene, ID (Mar. 16-19, 2000): 109.

Selinger, D. A. et al. "The Maize Regulatory Gene *B-Peru* Contains a DNA Rearrangement That Specifies Tissue-Specific Expression Through Both Positive and Negative Promoter Elements" *Genetics* 149 (1998):1125-38.

Vaucheret, H. and M. Fagard, "Transcriptional gene silecning in plants: targets, inducers and regulators" *Trends Genet.* 17 (2001): 29-35.

Vongs, A. et al. "*Arabidopsis thaliana* DNA Methylation Mutants" *Science* 260 (1993): 1926-1928.

Kermicle, Jerry L. "Epigenetic Silencing and Activation of a Maize r Gene", *Epigenetic Mechanisms of Gene Regulation*, V.E.A. Russo et al. eds. (New York: Cold Spring Harbor Laboratory Press) (1996): 267-287.

Matzke, A. J. M. et al. "Homology-dependent gene silencing in transgenic plants: epistatic silencing loci contain multiple copies of methylated transgenes", *Mol. Gen. Genet.* 244 (1994):219-229.

Meyer, P. and H. Saedler. "Homology-dependent gene silencing in plants", *Annu. Rev. Plant Physio. Plant Mol. Biol.* 47 (1996): 23-48.

Scheid, Ortrun Mittelsten et al. "Release of epigeneitc gene silencng by trans-acting mutations in *Arabidopsis*", *Proc. Natl. Acad. Sci. USA* 95 (1998): 632-637.

* cited by examiner

FIG. 3A    FIG. 3B    FIG. 3C
B' Mop1 / mop1-1    B' mop1-1 / mop1-1    B-I Mop1 / Mop1
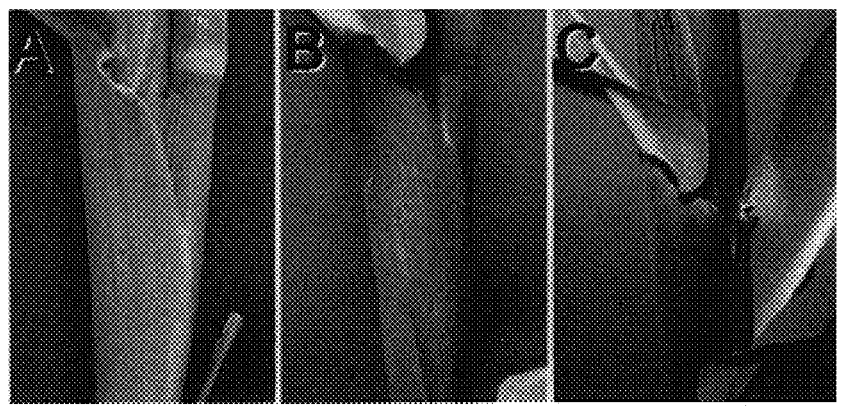
B' Sectors in a    Pl' Mop1 / -    Pl' mop1-1 / mop1-1
B' mop1-1 Plant
FIG. 3D    FIG. 3E    FIG. 3F

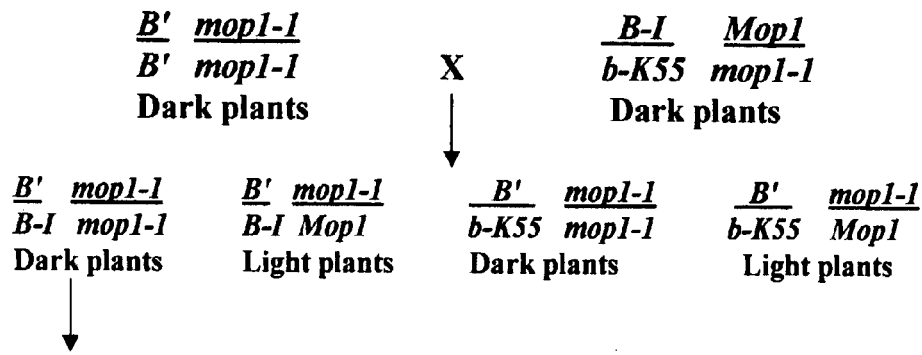

Testcross (by *B-Peru/B-I Mop1/Mop1* tester--diagram shows only *B-Peru* gametes of tester)

Gametes produced if paramutation
is prevented (*B-I* —✕→ *B'*):

50% *B' mop1-1*  X  *B-Peru Mop1*  ⟶  $\underline{B'\quad mop1\text{-}1}$  Light
                                           *B-Peru  Mop1*   plants 50% *B-I mop1-1*  X  *B-Peru Mop1*  ⟶  $\underline{B\text{-}I\quad mop1\text{-}1}$  Dark
                                            *B-Peru  Mop1*    plants Gametes produced if paramutation
occurred (*B-I*———▶*B'*):

100% *B' mop1-1*  X  *B-Peru Mop1*  ⟶  $\underline{B'\quad mop1\text{-}1}$  Light
                                            *B-Peru  Mop1*   plants

FIG. 9

*FIG. 11A*  *FIG. 11B*
*FIG. 11C*  *FIG. 11D*
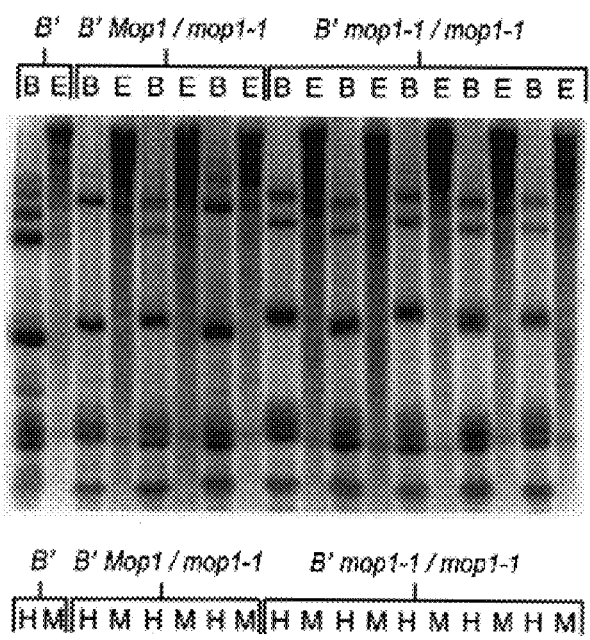
*FIG. 12A*
*FIG. 12B*

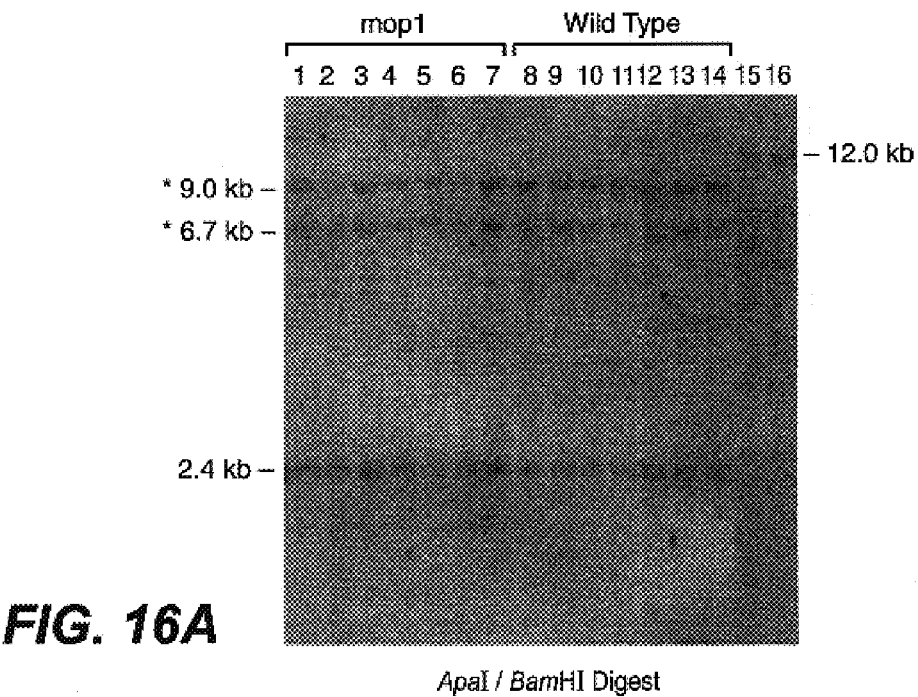
FIG. 16A
ApaI / BamHI Digest
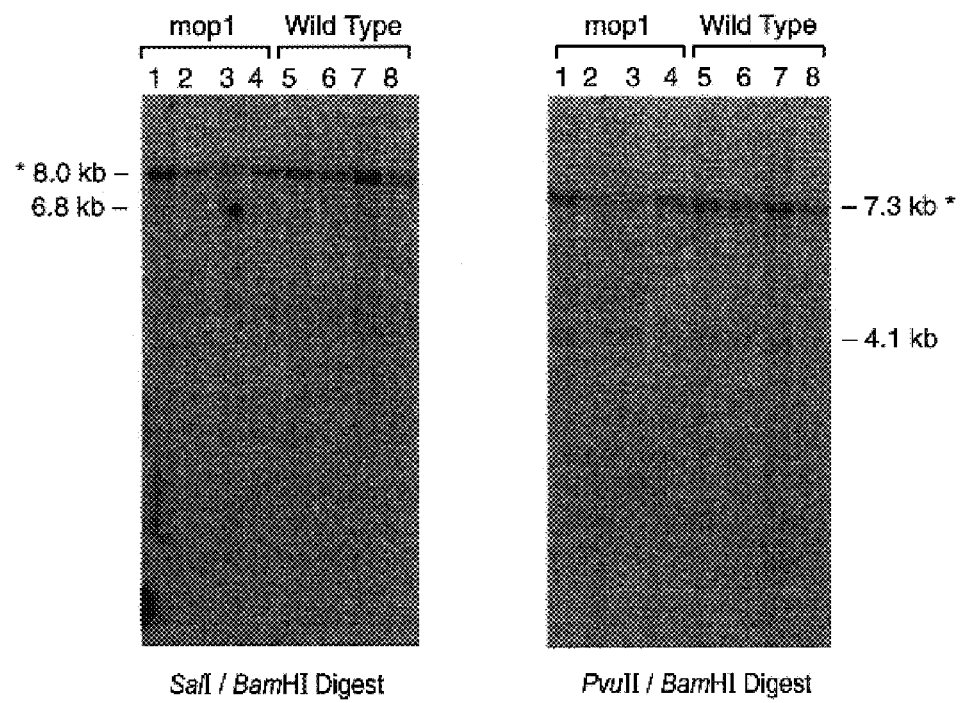
SalI / BamHI Digest
FIG. 16B
PvuII / BamHI Digest
FIG. 16C

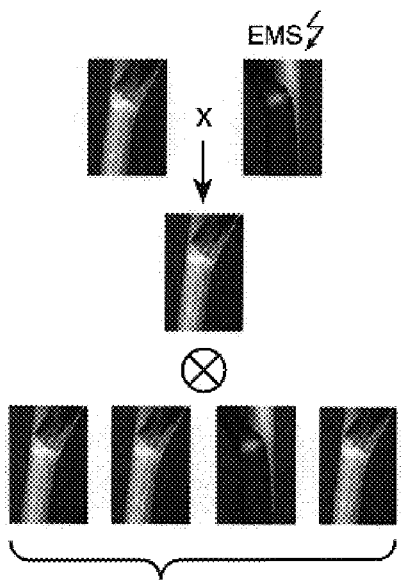 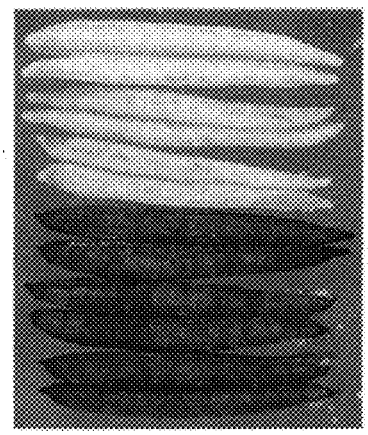
FIG. 17  FIG. 18A
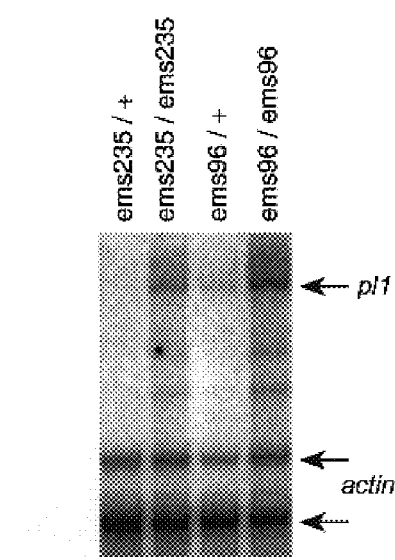 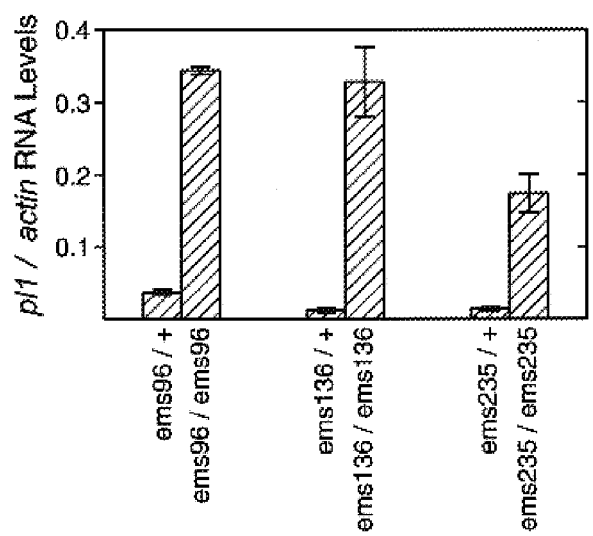
FIG. 18B  FIG. 18C

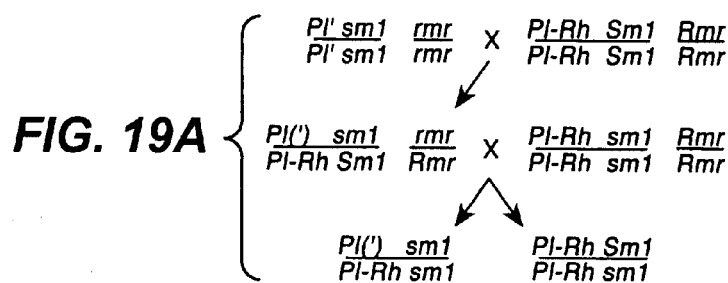
FIG. 19A
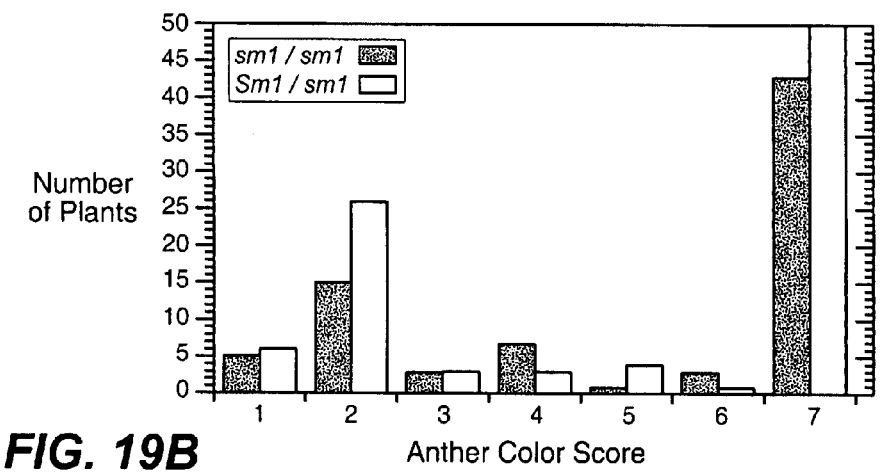
FIG. 19B Anther Color Score
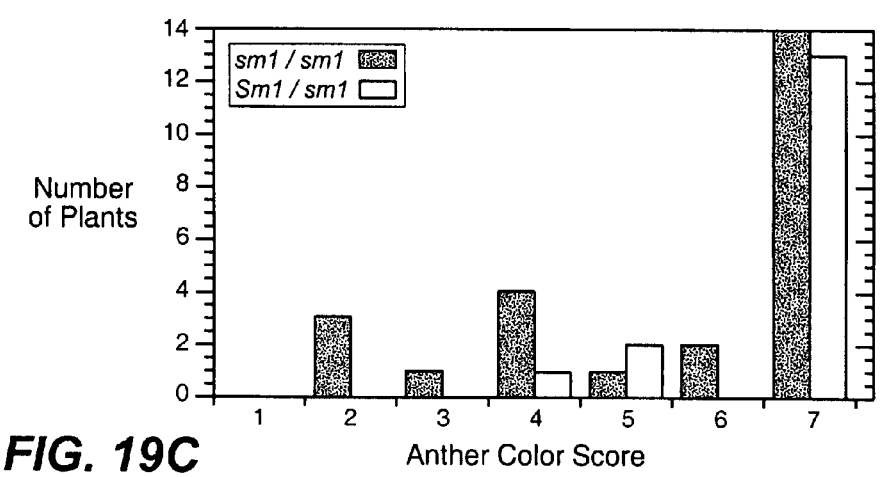
FIG. 19C Anther Color Score

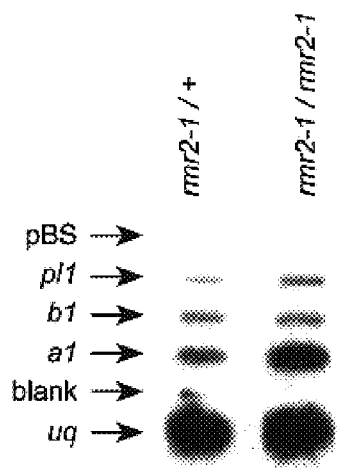
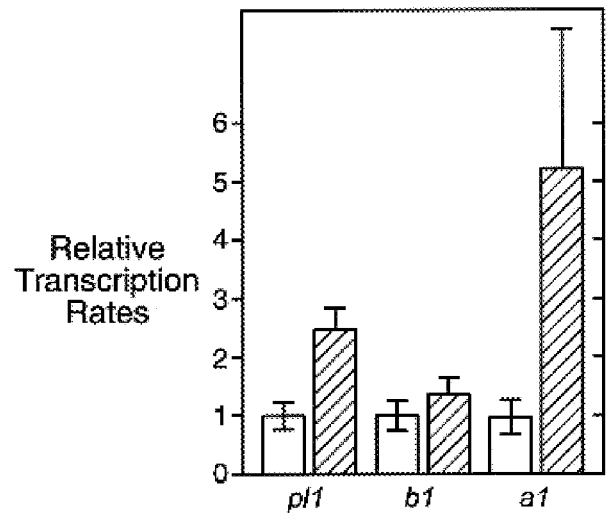
FIG. 22A          FIG. 22B
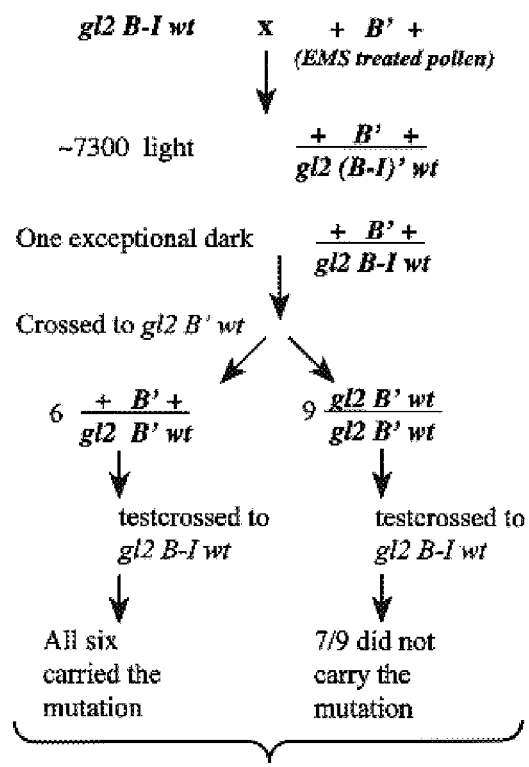
FIG. 23

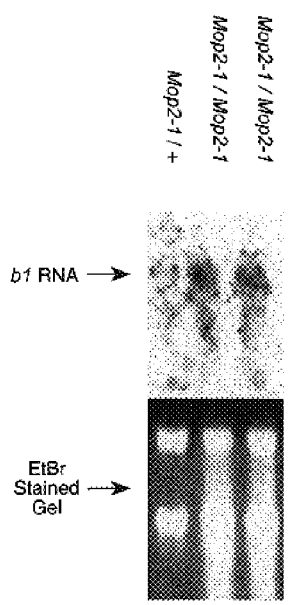
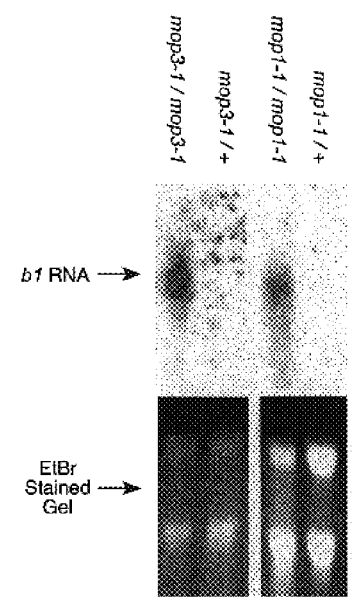
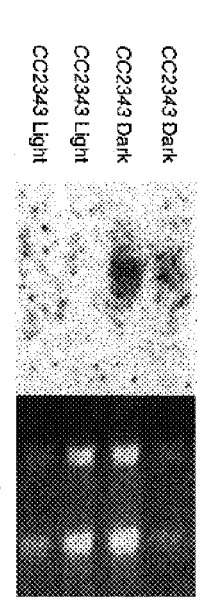
*FIG. 26A*  *FIG. 26B*  *FIG. 26C*

FIG. 29A
B' Mop2-1 / mop2    B' Mop2-1 / Mop2-1
35SB-I
FIG. 29B
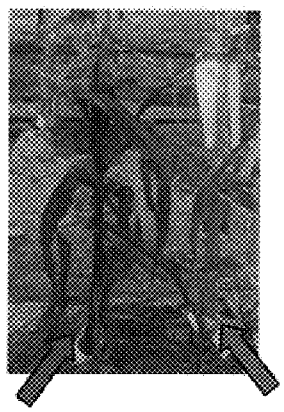
rmr2-1 / rmr2-1    Rmr2 / rmr2-1
35SB-I
FIG. 29C
B' mop1-1 / mop1-1    B' Mop1 / mop1-1
35SB-I
FIG. 29D
rmr1-1 / rmr1-1    Rmr1 / rmr1-1
35SB-I
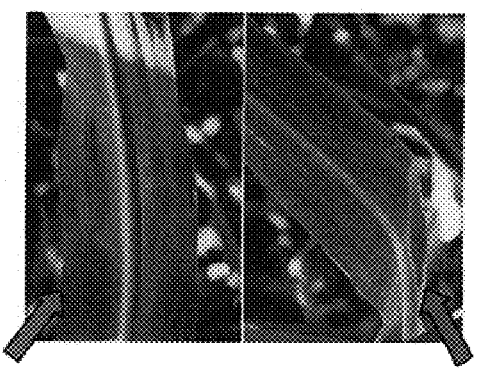
Rmr2 / rmr2-1         rmr2-1 / rmr2-1
BBBS
FIG. 29E

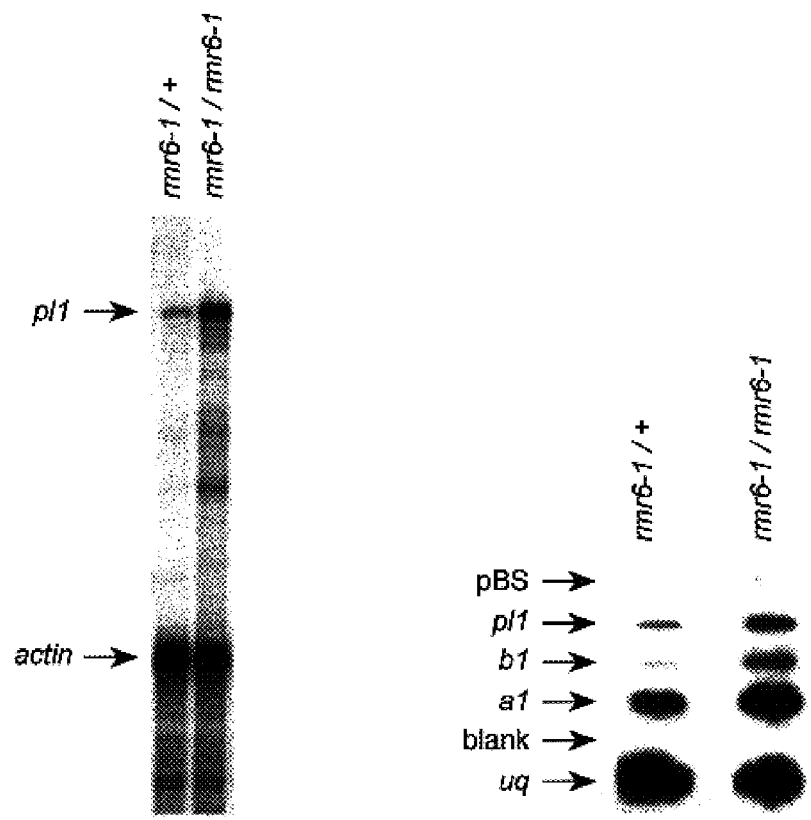
FIG. 34A      FIG. 34B
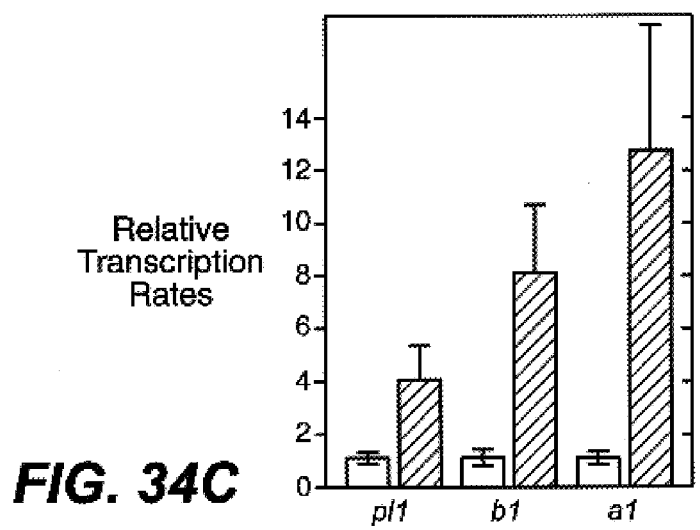
FIG. 34C

GENETIC FUNCTIONS REQUIRED FOR GENE SILENCING IN MAIZE

RELATED APPLICATION

This application claims the benefit under 35 U.S.C. §119(e) of U.S. provisional patent application No. 60/238,137 filed Oct. 5, 2000 which is hereby incorporated by reference in its entirety.

This invention was made with government support under Grant Numbers GM-35971 awarded by the National Institutes of Health; BIR-9104373, BIR-9303601, BIR-9626082, MCB9603638, and MCB998244 awarded by the National Science Foundation; NP-875 awarded by the American Cancer Society, and 97-35301-4430, 97-35301-5308, and 99-35301-7753, awarded by the United States Department of Agriculture. The U.S. Government has certain rights in the invention.

FIELD OF THE INVENTION

This invention is in the field of plant breeding. In particular, this invention relates to the isolation of new maize mutants with reduced gene silencing activity.

BACKGROUND OF THE INVENTION

The goal of *Zea mays* L. (corn) breeding is to combine various desirable traits in a single variety/hybrid. Such desirable traits include greater yield, better stalks, better roots, resistance to pesticides, pests and disease, tolerance to heat and drought, reduced time to crop maturity, better agronomic quality, higher nutritional value, and uniformity in germination times, stand establishment, growth rate, maturity and fruit size.

Modern molecular biology and transgenic technologies (genetic engineering) have greatly accelerated the introduction of new genes and, hence, new traits into corn lines. While useful, genetic engineering is hampered by transgene silencing problems. Transgene silencing is a little understood process by which genes introduced by genetic engineering are silenced or turned off. As such, transgene silencing is a major impediment to the use of genetic engineering for corn improvement. At present, the solution to transgene silencing is to search through a large number of transgenic events for transgene loci that are active and stable. This is a painstaking and laborious process, which greatly increases the cost of corn breeding using genetic engineering techniques.

In addition to transgene silencing, there are other examples of gene silencing that are variable, unstable, but heritable. In corn these include the cycling of transposable elements between active and inactive states and paramutation, gene silencing that occurs through interactions between specific alleles of a gene. The mechanism of silencing is not understood in any case, but current hypotheses invoke heritable alterations to chromatin structure.

There are no known mutants in corn that can prevent or reverse gene silencing. The availability of genetic stocks that prevent the establishment or maintenance of transgene silencing would be extremely useful for engineering and breeding new corn lines.

SUMMARY OF THE INVENTION

In order to meet these needs, the present invention is directed to new corn lines.

In particular, the present invention is directed to a mutant corn plant wherein upon propagation a change in gene activity of a paramutable allele of the mutant corn plant due to its exposure to a paramutagenic allele is reduced as compared to a wild type plant or wherein the gene activity of a paramutagenic allele of the mutant plant is not maintained as compared to a wild type plant. In one format the change in gene activity of an B-I allele due to exposure to a B' allele is prevented in the mutants. In another format, the change in gene activity of an PI-Rh allele due to its exposure to a PI' allele is reduced in the mutants. In another format, the change in activity of an R-d allele due to exposure to an PI' allele is increased in the mutants.

The present invention is further directed to a mutant corn plant derived from a wild type corn plant wherein the mutant corn plant comprises one or more mutations that reduce the establishment, or the maintenance of paramutation or both, in the mutant corn plant as compared to the wild type corn plant. In one embodiment, the mutation is a dominant mutation. In another embodiment, the mutation is a recessive mutation.

In one format, the mutant corn plant of the invention is reduced in the establishment of paramutation at the b1 locus. In another format, the mutant corn plant of the invention is reduced in the establishment of paramutation at the r1 locus. In another format, the mutant corn plant of the invention is reduced in the establishment of paramutation at the pl1 locus. In yet another format paramutation is not established at the b1, r1 and/or pl1 loci in the mutant corn plant of the invention.

In another format, the mutant corn plant is reduced in the maintenance of paramutation at the pl1 locus. In another format, the mutant corn plant is reduced in the heritable maintenance of paramutation at the pl1 locus.

The present invention is further directed to seed produced by the mutant corn plants of the invention. The invention is further directed to progeny seed produced by crossing the mutant corn plants of the invention with another corn plant.

The present invention is further directed to tissue culture of regenerable cells of the mutant corn plants of the invention.

The present invention is further directed to a mutant corn plant that fails to maintain the B' paramutant state, manifest as an increase of 2–3 fold or greater of b1 RNA levels relative to a corresponding wild type plant and to progeny seed produced therefrom.

The present invention is further directed to a mutant corn plant that fails to maintain the PI' paramutant state, manifest as an increase of 2–3 fold or greater of pl1 RNA levels relative to a corresponding wild type plant and to progeny seed produced therefrom.

The present invention is further directed to a mutant corn plant that fails to heritably maintain the PI' paramutant state, manifest as transmission of nonparamutagenic pl1 alleles from a homozygous PI' genotype, and to progeny seed and plants derived therefrom.

The present invention is further directed to a mutant corn plant, in which the normally invariant occurrence of paramutation at the b1, pl1 or r1 loci is prevented, and to progeny seed and plants derived therefrom.

The present invention is further directed to a mutant corn plant exhibiting reduced methylation of Mutator elements in the absence of active MuDR elements, relative to a corresponding wild type plant with methylated Mutator elements and to progeny seed and plants derived therefrom.

The present invention is further directed to a mutant corn plant wherein the mutation causes at least a two-three fold increase in transgene RNA relative to the transgene in sibling or parental wild type plants and to seed and progeny plants derived from the mutant corn plant.

The present invention is further directed to a process of producing a transgenic corn plant with an activated transgene comprising crossing a parental transgenic plant with a mutant plant wherein the parental transgenic plant has a transgene and the mutant plant is derived from a wild type corn plant. In the method, the mutant corn plant has one or more mutations that reduce the establishment or maintenance of paramutation in the mutant plant. In one format, the transgene in the parental transgenic plant is silenced and the mutation activates the silenced transgene. In another format, the transgene in the parental transgenic plant is activated and the mutation serves to prevent the transgene from being silenced in subsequent generations.

In the method of the invention a transgenic plant is produced where a silenced transgene is activated by the presence of a mutation or maintained active where the transgene is active in the parental line. The mutation reduces the establishment or maintenance of paramutation as compared to the wild type plant. In the method of the invention, the first progeny transgenic plant is outcrossed to a wild type corn plant to produce a second progeny transgenic plant wherein the silenced transgene remains activated in the second progeny transgenic plant but the second progeny transgenic plant is no longer reduced in the establishment or maintenance of paramutation as compared to the wild type plant because the mutation that originally activated the transgene is no longer present. This applies to progeny seed and plants derived therefrom.

The invention is further directed to plants produced by the methods of the invention and seed derived therefrom.

In particular, the present invention is directed to new corn plants designated Mop1-1; Mop1-2EMS; Mop2-1; mop3-1; CC2343; rmr1-1; rmr1-2; rmr2-1; rmr7-1; rmr7-2; rmr6-1; rmr8-1rmr9-1; Mop1-4; rmr11-1; Mop1-5 and to seeds derived therefrom.

Accession No. PTA-4030; corn seed designated mop; 1 and having ATCC Accession No. PTA-3829; corn seed designated Mop1-2EMS and having ATCC Accession No. PTA-3826; corn seed designated rmr1-1 and having ATCC Accession No. PTA-3965; corn seed designated rmr1-2 and having ATCC Accession No. PTA-3966; corn seed designated rmr2-1 and having ATCC Accession No. PTA-3956; corn seed designated rmr7-1 and having ATCC Accession No. PTA-3958; corn seed designated rmr6-1 and having ATCC Accession No. PTA-3957; corn seed designated rmr8-1 and having ATCC Accession No. PTA-3960; corn seed designated rmr9-1 and having ATCC Accession No. PTA-3961; corn seed designated rmr7-2 and having ATCC Accession No. PTA-3959; corn seed designated rmr11-1 and having ATCC Accession No. PTA-3962; corn seed designated Mop1-4 and having ATCC Accession No. PTA-3963; corn seed designated cc2343 and having ATCC Accession No. PTA-3827; and corn seed designated Mop1-5 and having ATCC Accession No. PTA-3964.

The present invention is also directed to a corn plant having all of the phenotypic and morphological characteristics of a plant produced from corn seed selected from the seed designated Mop1-1 and having ATCC Accession No. PTA-3828; corn seed designated Mop1-2EMS and having ATCC Accession No. PTA-3826; corn seed designated Mop2-1 and having ATCC Accession No. PTA-4030; corn seed designated mop3-1 and having ATCC Accession No. PTA-3829; corn seed designated rmr1-1 and having ATCC Accession No. PTA-3965; corn seed designated rmr1-2 and having ATCC Accession No. PTA-3966; corn seed designated rmr2-1 and having ATCC Accession No. PTA-3956; corn seed designated rmr7-1 and having ATCC Accession No. PTA-3958; corn seed designated rmr6-1 and having ATCC Accession No. PTA-3957; corn seed designated rmr8-1 and having ATCC Accession No. PTA-3960; corn seed designated rmr9-1 and having ATCC Accession No. PTA-3961; corn seed designated rmr7-2 and having ATCC Accession No. PTA-3959; corn seed designated rmr11-1 and having ATCC Accession No. PTA-3962; corn seed designated Mop1-4 and having ATCC Accession No. PTA-3963; corn seed designated cc2343 and having ATCC Accession No. PTA-3827; and corn seed designated Mop1-5 and having ATCC Accession No. PTA-3964.

The present invention is directed to an ovule or pollen of a plant having all of the phenotypic and morphological characteristics of a plant produced from corn seed where the corn seed is selected from the corn seed designated Mop1-1 and having ATCC Accession No. PTA-3828; corn seed designated Mop1-2EMS and having ATCC Accession No. PTA-3826; corn seed designated Mop2-1 and having ATCC Accession No. PTA-4030; corn seed designated mop3-1 and having ATCC Accession No. PTA-3829; corn seed designated rmr1-1 and having ATCC Accession No. PTA-3965; corn seed designated rmr1-2 and having ATCC Accession No. PTA-3966; corn seed designated rmr2-1 and having ATCC Accession No. PTA-3956; corn seed designated rmr7-1 and having ATCC Accession No. PTA-3958; corn seed designated rmr6-1 and having ATCC Accession No. PTA-3957; corn seed designated rmr8-1 and having ATCC Accession No. PTA-3960; corn seed designated rmr9-1 and having ATCC Accession No. PTA-3961; corn seed designated rmr7-2 and having ATCC Accession No. PTA-3959; corn seed designated rmr11-1 and having ATCC Accession No. PTA-3962; corn seed designated Mop1-4 and having ATCC Accession No. PTA-3963; corn seed designated cc2343 and having ATCC Accession No. PTA-3827; and corn seed designated Mop1-5 and having ATCC Accession No. PTA-3964.

The present invention is further directed to progeny seed produced from crossing a plant grown from a seed selected from the group of corn seed including corn seed designated Mop1-1 and having ATCC Accession No. PTA-3828; corn seed designated Mop1-2EMS and having ATCC Accession No. PTA-3826; corn seed designated Mop2-1 and having ATCC Accession No. PTA-4030; corn seed designated mop3-1 and having ATCC Accession No. PTA-3829; corn seed designated rmr1-1 and having ATCC Accession No. PTA-3965; corn seed designated rmr1-2 and having ATCC Accession No. PTA-3966; corn seed designated rmr2-1 and having ATCC Accession No. PTA-3956; corn seed designated rmr7-1 and having ATCC Accession No. PTA-3958; corn seed designated rmr6-1 and having ATCC Accession No. PTA-3957; corn seed designated rmr8-1 and having ATCC Accession No. PTA-3960; corn seed designated rmr9-1 and having ATCC Accession No. PTA-3961; corn seed designated rmr7-2 and having ATCC Accession No. PTA-3959; corn seed designated rmr11-1 and having ATCC Accession No. PTA-3962; corn seed designated Mop1-4 and having ATCC Accession No. PTA-3963; corn seed designated cc2343 and having ATCC Accession No. PTA-3827; and corn seed designated Mop1-5 and having ATCC Accession No. PTA-3964; with another corn plant and the corn seed produced therefrom.

The present invention is further directed to tissue culture of regenerable cells of corn plants selected from Mop1-1;

Mop1-2EMS; Mop2-1; mop3-1; rmr1-1; rmr1-2; rmr2-1; rmr7-1; rmr6-1; rmr8-1rmr9-1;rmr7-2; rmr11-1; Mop1-4, cc2343 and Mop1-5and seeds derived therefrom, wherein the tissue culture regenerates plants capable of expressing all the physiological and morphological characteristics of the corn plants selected from Mop1-1; Mop1-2EMS; Mop2-1; rmr1-1; rmr1-2; rmr2-1; rmr7-1; rmr7-2; rmr6-1; rmr8-1; rmr9-1; cc2343; rmr11-1; Mop1-4; Mop1-5 and seeds derived therefrom, respectively.

The tissue culture of the invention may include regenerable cells comprising cells derived from embryos, immature embryos, meristematic cells, immature tassels, microspores, pollen, leaves, anthers, roots, root tips, silk, flowers, kernels, ears, cobs, husks, stalks, protoplasts or callus.

The present invention is further directed to corn plants regenerated from the tissue culture of regenerable cells of the invention.

The present invention is further directed to a process of producing corn seed, comprising crossing a first parent corn plant with a second parent corn plant, wherein the first or second corn plant is a corn plant selected from Mop1-1, Mop1-2EMS; mop-2-1; mop-3-1; rmr1-1; rmr1-2; rmr2-1; rmr7-1; rmr7-2; rmr6-1; rmr8-1; rmr9-1; rmr11-1; cc2343; Mop1-4 and Mop1-5. The process of producing the corn seed of the invention comprises the steps of: (a) planting in pollinating proximity seeds of the first and second corn plants; (b) cultivating the seeds of the first and second corn plants into plants that bear flowers; (c) emasculating the male flowers of the first or second corn plant to produce an emasculated corn plant; (d) allowing cross-pollination to occur between the first and second corn plants; and (e) harvesting seeds produced on the emasculated corn plant.

The process of producing the corn seed of the invention also includes hand-pollinations that can be carried out on a large scale. Briefly, female styles are protected from stray pollen by placing small bags over the developing ear shoots, pollen is collected from tassels and placed on the silks of selected plants.

The present invention is further directed to a method of producing hybrid corn plants and hybrid corn seed using the process of the invention and F1 hybrid seed produced therefrom.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The invention will be better understood by reference to drawings in which:

FIG. 1 shows phenotypes and crosses demonstrating paramutation.

FIG. 2 shows structures of genes that undergo paramutation. Coding regions are indicated by black horizontal arrows. The coding and promoter regions are not to scale. Different promoter regions are indicated by distinct boxes. Promoter regions with sequence similarity are indicated by the same boxes: solid, striped or open.

FIGS. 3A–3F show the phenotypes associated with the Mop1-1 mutation. The genotypes of the photographed plants are indicated below each panel. (A) B' Mop1/Mop1-1, (B) B' Mop1-1/Mop1-1, (C) B-I Mop1/Mop1, (D) B' Mop1-1/Mop1-1 plant with B'-like sectors, (E) PI' Mop1/– (either Mop1/Mop1 or Mop1/Mop1-1), (F) PI' Mop1-1/Mop1-1.

FIG. 9 shows a diagram outlining a test for the ability of Mop1-1 to prevent b1paramutation. B'/B' Mop1-1/Mop1-1 plants were crossed to B-I/b Mop1/Mop1-1 plants, generating four types of segregating progeny. The B'/B-I and B'/b progeny were distinguished by restriction fragment length polymorphisms. The B'/b progeny were not analyzed further. Both classes of B'/B-I progeny (dark and light) were crossed with testers heterozygous for B-I/B-Peru, Mop1/Mop1 (and with testers null for b1, not diagrammed) to test whether the B-I allele heterozygous with B' had become B' in the Mop1-1/Mop1-1 versus Mop1/Mop1-1 plants. The expectations for crosses with B'/B-I Mop1-1/Mop1-1 with one type of tester (B-Peru Mop1 which gives purple kernels) are shown. The expectation for the B'/B-I Mop1/Mop1-1 progeny is that all offspring will be light plants (not diagrammed).

FIGS. 11A–11D show phenotypes characteristic of Mop1 mutations relative to Wild-Type siblings. (A) A B' Mop1/Mop1-1 individual bearing a normal tassel. (B) A B' Mop1-1/Mop1-1 individual bearing a feminized tassel (strong tasselseed). (C) A B'/− Mop1-2EMS/Mop1-2EMS individual bearing a severely barrenized tassel. (D) A runty B' Mop1-1/Mop1-1 individual in which the feminized terminal infloresence failed to emerge.

FIGS. 12A–12B show DNA blots assaying methylation of repeated sequences. Individual genotypes are indicated above the DNA blots (B' stands for B'/B' Mop1/Mop1). (A) Samples digested with the methylation insensitive enzyme BstNI (B) and the methylation sensitive enzyme EcoRII (E) were probed with the 45S ribosomal repeat. (B) Samples digested with HpaII (H) or MspI (M) were probed with the centromere repeat.

FIG. 17 shows an outline of a genetic screen used to identify mutations affecting seedling pigmentation. Pl-Rh seedlings have fully colored first leaf sheaths (top right). Pl' seedlings have very weakly colored first leaf sheaths (top left). Pollen from Pl-Rh plants was treated with ethyl methanesulfonate (EMS) and brushed on the silks of Pl' plants. All Pl'/Pl-Rh M1 plants had a Pl' seedling phenotype (middle panel). M1 plants were self pollinated and M2 families were screened for Pl-Rh-like seedlings. The bottom four panels represent a M2 family segregating 3:1 for Pl' and Pl-Rh-like seedlings.

FIGS. 18A–18C show how EMS-derived mutations affect anther pigment and pl1 RNA levels. (A) Anther phenotypes of plants that are heterozygous (top three variegated anthers) and homozygous (bottom three fully colored anthers) for the ems235 (rmr1-2) allele. The difference between anther pigment phenotypes was identical for both the ems96 (rmr2-1) and ems136 (rmr1-1) alleles (not shown). (B) RNase-protection assay measuring the levels of pI1 and actin RNA found in anther tissues of plants with the indicated genotypes. (C) Histogram of RNase-protection results for pI1 RNA levels measured relative to actin RNA for the indicated genotypes. Bars represent average measurements for each genotype and crossbars above each bar indicate the standard error. The number of samples measured for each genotype is as follows: ems96/+, n=2; ems96/ems96, n=2; ems136/+, n=3; ems136/ems136, n=4; ems235/+, n=5; ems235/ems235, n=6.

FIGS. 19A–C show that PI' can change to PI-Rh in plants that are homozygous for rmr mutations. (A) Pedigree outlining two genetic crosses used to show that plants homozygous for the rmr mutations can transmit non-paramutagenic PI-Rh alleles. PI(') is used to identify a pI1 allele that should have been PI' in the first generation but is not paramutagenic; the PI(')/PI-Rh plants in the second cross have fully colored anthers. (B) Results of crosses initiated with plants that were homozygous for the rmr1-1 allele. Histogram represents the number of plants with a given anther color score that were either sm1/sm1 (salmon colored silks; closed bars) or Sm1/sm1 (yellow silks; open bars). (C) Results of crosses initiated with plants that were homozygous for the rmr2-1 allele.

FIGS. 22A–B show results of in vitro transcription reactions comparing B-I/B-I; PI/PI'; rmr2-1/rmr2-1 (closed bars) and B-I/B-I; PI'/PI'; rmr2-1/Rmr2 (indicated as rmr2-1/+) (open bars) husk tissues. (A) is one example of the primary results while (B) represents combined results from 5 independent experiments. Experimental design and representation of results are as described in Hollick et. al 2000.

FIG. 23 shows a diagram indicating the identification of a dominant mutation. The fact that paramutation always occurs when B-I and B' are heterozygous, and that this phenotype is apparent in all F1 individuals means that one can efficiently screen for dominant mutations that disrupt the establishment of paramutation. An exceptional dark plant was identified among numerous light siblings. This individual was found to carry a dominant mutation, referred to as Mop2-1. This original dark plant was outcrossed to gl2 B' wt, and progeny of this cross were crossed to gl2 B-I wt. Following the marked chromosomes in these crosses demonstrate that this mutation is loosely linked to b1, mapping to the short arm of chromsome 2.

FIG. 26 shows an RNA blot demonstrating differences in b1 transcript levels between mutants and their wild-type siblings. A) Comparison of b1 RNA levels in Mop2-1/Mop2-1 versus Mop2-1/+ husk tissue. B) Comparison of b1 RNA levels in mop3-1/mop3-1 versus mop3-1/+ husk tissue. Mop1-1/Mop1-1 versus Mop1-1/+ husk samples were also included on this blot as a control. C) Comparison of b1 RNA levels in husk tissue from CC2343 lights versus darks husk tissue. All plants were B'. RNA isolation was as described in Example 1 and preparation of the RNA blot, probe and hybridization conditions were as described in Patterson et al. 1993.

FIG. 27A shows the darkly pigmented phenotype of mop3-1/mop3-1 B'. FIG. 27B shows the phenotypes associated with Mop3/mop3-1, which has the same phenotype as plants homozygous for the wild type allele. FIG. 27C shows dark and light plants in a CC2343 family. Note how much taller the light plants are relative to the dark plants. FIG. 27D shows a medium dark plant segregating in a CC2343 family. FIGS. E and F show a dark plant without a tassel and a medium dark plant with a partially feminized tassel from cc2343 families. These phenotypes are also seen in mop3-1 families.

FIGS. 29A–D show the phenotypes associated with Mop1-1, Mop2-1, rmr1-1 or rmr2-1 activation of a previously transcriptionally silent 35S B-I genomic transgene. FIG. 29E shows rmr2-1 activation of a previously silent BBBS transgene. The phenotype was the same with Mop1-1 and rmr1-1 and the BBBS transgene. The genotypes of each plant are indicated below each panel.

FIGS. 34A–C show molecular genetic expression analyses of rmr6-1/rmr6-1 and rmr6-1/Rmr6 (indicated as rmr6-1/+) materials. (A) RNase protection results carried out as described in Example 3. B–C show results of in vitro transcription reactions comparing B-I/B'; PI'/PI'; rmr6-1/ rmr6-1 (closed bars) and B-I/B-I; PI'/PI'; rmr6-11+ (open bars) husk tissues. (B) is one example of the primary results while (C) represents combined results from 5 independent experiments.

DETAILED DESCRIPTION OF THE INVENTION

Figure 1A:
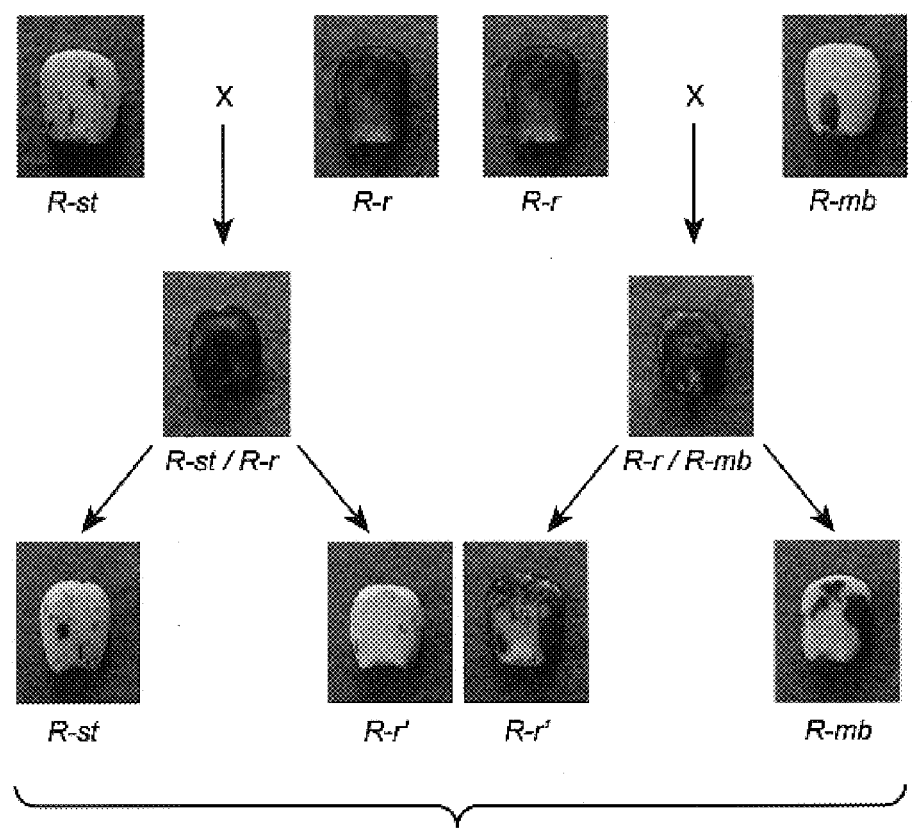
FIG. 1A shows seed phenotypes of r1 haplotypes. The top panels are the phenotypes of the parents, the paramutable, R-r haplotype or the paramutagenic R-st and R-mb haplotype. It does not matter which parent is used as male versus female. The central panel shows the phenotype of the F1 seeds. When these are planted and crossed as male to colorless recessive null r1alleles (not shown), the resulting seed phenotypes segregate (third panel). R-st and R-mb segregate unchanged. R-r is changed to a lower expressing form, R-r'. Typically R-st is more paramutagenic than R-mb, as R-r' is less pigmented when segregating from a R-st versus a R-mb F1.

In order to more fully understand the invention, the following definitions are provided:

AFLP Marker: An Amplified Restriction Fragment Length Polymorphism is a marker used in genetic mapping.

Allele: Any of one or more alternative forms of a gene locus, all of which alleles relate to one trait or characteristic. In a diploid cell or organism, the two alleles of a given gene occupy corresponding loci on a pair of homologous chromosomes.

Anther Color Score (ACS): A graded quantitative score between 1 and 7 describing relative amounts of anthocyanin pigment found in anthers of maize plants expressing PI' or PI-Rh alleles. ACS 1 describes anthers with virtually no pigment, ACS 7 describes fully-pigmented anthers, and ACS 2–6 describe intermediate levels of variegated pigment.

Backcrossing: A process in which a breeder repeatedly crosses hybrid progeny back to one of the parents, for example, a first generation hybrid (F1) with one of the parental genotypes of the F1 hybrid.

Crossing: The pollination of a female flower of a corn plant, thereby resulting in the production of seed from the flower.

Cross-Pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

Expression: The expression of a gene refers to the production of the RNA or protein encoded by the gene. For protein encoding genes, this involves transcription of the gene into RNA and translation of the RNA into protein. Gene expression can be monitored by examining RNA levels, examining transcription rates, or by measuring protein levels.

Epigenetics: Epigenetics refers to altered gene expression associated with alternative chromatin and/or methylation states superimposed upon an unchanged primary DNA sequence.

F1 Hybrid: The first generation progeny of the cross of two plants.

Gene Silencing: Repression of gene activity via inhibited transcription and/or by increased RNA degradation.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Heterosis: A synonym for "hybrid vigor" where the superiority of the offspring of a cross between two stocks to the better of the parents. Also used as a synonym for "heterozygote advantage" which is a relation between alleles in which the heterozygote, Aa, is superior to either homozygote, AA or aa. Heterosis in the latter sense is often invoked to explain hybrid vigor.

Linkage: A phenomenon wherein alleles on the same chromosome tend to segregate together more often than expected by chance if their transmission was independent.

Maize: Maize (*Zea mays* L.) is often referred to as corn in the United States. Maize can be bred by both self-pollination and cross-pollination techniques. Maize has separate male and female flowers on the same plant, located on the tassel and the ear, respectively. Natural pollination occurs in maize when the wind blows pollen from the tassels to the silks that protrude from the tops of ears. Maize and corn are used interchangeably throughout this specification.

Maize Nomenclature: Maize nomenclature is the means to identify maize genes and alleles. A gene is designated with lower case italics (b1) in maize nomenclature (See also Trends in Genetics "Genetic Nomenclature Guide" (1995) or the web site agron.missouri.edu at maize nomenclature-.html). Specific alleles are indicated with an allele designation separated from the gene designation with a hyphen. Dominant alleles are indicated by an upper case gene designation (B-Peru) and recessive alleles by a lower case gene designation (b1-K55). Gene products are indicated by all caps and are not italicized (B).

Marker: A readily detectable phenotype or molecular or biochemical characteristic, preferably inherited in codominant fashion (both alleles at a locus in a diploid heterozygote are readily detectable), preferably with no environmental variance component, i.e., heritability of 1. Examples of markers include AFLPs, SNPs and SSLP markers.

Methylation: Process by which methyl groups are added to certain nucleotides in genomic DNA. Methyl sensitive restriction enzymes, such as SacI and HinfI cannot cut sequences with certain specific methylations. Methylation of DNA is often associated with reduced gene activity.

Mutant Corn Plant: A plant that is homozygous for a recessive or dominant mutation in a particular gene or heterozygous for a dominant mutation in a particular gene. This mutation is usually associated with a change in the DNA sequence of the gene that is altered.

Paramutation: A mitotically and meiotically heritable change in the transcriptional activity of a gene that can occur spontaneously or be induced by a paramutagenic allele. Paramutation is the change in gene activity of one allele due to its exposure to another allele. For example, at the b1 locus in maize, strong activity of the B-I allele confers dark purple pigmentation throughout the plant while weak activity of the B' allele confers light pigment. In a B-I/B' heterozygote, B-I is invariably changed to B'; only B' alleles segregate from the heterozygote (FIG. 1). The sensitive allele (B-I) is described as paramutable and the inducing allele (B') is described as paramutagenic. Similarly, with paramutation at pl1, PI-Rh is paramutable and PI' is paramutagenic (see FIG. 1).

Establishment of Paramutation: The ability of a paramutagenic allele to change a paramutable allele into a paramutagenic allele. For example, when B' is crossed with B-I, B-I is always changed to B', paramutation is always established when these two alleles are combined in a heterozygote.

Maintenance of Paramutation: The ability of a paramutant state (such as B) to be maintained. For example, when plants containing B' or PI' are grown, the low transcription level and the ability to be paramutagenic is maintained in those plants.

Heritable Maintenance of the Paramutant State: The ability of a paramutant state (such as B' or PI') to be maintained in subsequent generations. When B' or PI' are sexually transmitted, the low transcription level and the ability to be paramutagenic is maintained in progeny plants.

Reduction in the Establishment of Paramutation: In wild type genetic backgrounds when B' is crossed with B-I, when Pl' is crossed with Pl-Rh, or when R-st is crossed with R-d, paramutation always occurs, it is always established. For the b1 and r1 loci over 100,000 different events at these two loci have been examined in the 50 years this has been studied. For pl1, several thousand events have been examined in the 10 years this has been studied. In the presence of certain mutations, paramutation is prevented. For example, in every plant that was homozygous for Mop1-1 (Example 1), the establishment of paramutation was completedly prevented; it was reduced by 100%.

Reduction in the Maintenance of Paramutation: When B' is in wild type genetic backgrounds, paramutation is always maintained: B' always shows reduced transcription and strong paramutagenic activity. In the presence of certain mutations, such as Mop1-1, the transcription rate and RNA levels of B' are dramatically increased (Example 1).

Reduction in the Heritable Maintenance of the Paramutant State: When Pl' is sexually transmitted from Pl' homozygotes in wild type genetic backgrounds, paramutation is always maintained: Pl' shows reduced transcription and strong paramutagenic activity. In certain mutant plants, the RNA levels from Pl' are increased, and in addition, non-paramutagenic pl1 alleles are sexually transmitted from homozygous P' genotypes.

Paramutagenic Alleles: Paramutagenic alleles induce a change in sensitive, paramutable alleles. Examples include B', Pl' and R-st.

Paramutable Alleles: Paramutable alleles are alleles that are sensitive to paramutagenic alleles. Examples include B-1, Pl-Rh, and R-d. Following paramutation, sensitive alleles are termed paramutant (or paramutated) and designated with an apostrophe (i.e., generically, B'; Pl'; R', etc.) In the examples of b1 and pl1 paramutation, once the paramutable alleles becomed paramutated they are paramutagenic.

Neutral Alleles: Neutral alleles neither induce nor respond to paramutation.

Progeny Plant: A plant produced from a parental line by crossing or selfing.

Phenotype: The detectable characteristics of a cell or organism, which characteristics are the manifestation of the genetic makeup of the organism or cell and the environment.

Regeneration: The development of a plant from tissue culture.

RFLP Genetic Marker Profile: A profile of band patterns of DNA fragment lengths typically separated by agarose gel electrophoresis after restriction endonuclease digestion of DNA.

Self-Pollination: The transfer of pollen from the anther to the stigma of the same plant.

Single Locus Converted (Conversion) Plant: Plants which are developed by a plant breeding technique called backcrossing wherein essentially all of the desired morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus).

SSLP Marker: A Short Sequence Length Polymorphism marker is a marker utilized in mapping.

SNP Marker: A Single Nucleotide Polymorphism is a marker utilized in mapping.

Tissue Culture: A composition comprising isolated cells of the same or a different type or a collection of such cells organized into parts of a plant.

Transgene: A genetic sequence that has been introduced into the nuclear, or chloroplast genome of a maize plant by a genetic transformation technique to produce a transgenic plant.

Transgene Silencing: Repression of transgene activity via inhibited transcription and/or increased RNA degradation.

Taking into account these definitions, the present invention relates to the isolation and characterization of corn mutants altered in the establishment or maintenance of paramutation, an example of gene silencing.

Screening System

Genetic and molecular studies of the *Zea mays* L. corn (maize) b1 (booster 1) and pl1 (purple plant 1) loci are utilized in this invention to isolate new corn lines with reduced gene silencing activity. The b1 gene encodes a transcriptional regulator required for anthocyanin pigment synthesis. Two particular b1 alleles show strong allelic interactions that lead to heritable changes in b1 gene activity. Paramutated and non-paramutated phenotypes can be distinguished on the basis of seedling pigment (2–3 weeks old), immature plants and mature plants. The pl1 gene encodes a different transcriptional regulator also required for anthocyanin pigment synthesis. Two particular pl1 alleles show a strong allelic interaction that leads to heritable changes in pl1 gene activity. Paramutated and non-paramutated phenotypes can be distinguished on the basis of seedling pigment (14–18 days post-imbibition), mature plants and anthers of mature plants. The visual nature of the assay at an early growth stage and throughout development, and the non-essential nature of the anthocyanin pathway make it an excellent system for studying gene silencing. Most of the genes encoding both the specific biosynthetic enzymes and the transcriptional regulators have been cloned and sequenced. Pigment levels are a simple and sensitive indicator of quantitative changes in RNA accumulation of these transcriptional regulatory loci. The b1 and r1 loci encode functionally duplicate basic-helix-loop-helix (bHLH) transcription factors and the pl1 and c1 loci encode functionally duplicate Myb-like transcription factors. Production of pigment co-requires the function of both a bHLH (b1 or r1) and a Myb (pl1 or c1) factor. Since alleles of all four loci have distinctive tissue-specific expression patterns, it is the specific combination of various alleles that determine whether or not pigment is produced in any given tissue.

Paramutation

All examples of paramutation involve an interaction between alleles that leads to a heritable reduction in the expression of one of the alleles. Alleles sensitive to altered expression are termed paramutable, and alleles inducing the change, paramutagenic. Following paramutation, sensitive alleles are termed paramutant (or paramutated) and designated with an apostrophe (i.e., generically, B', Pl', R' etc.). Many alleles at r1, b1 and pl1 do not participate in paramutation; these alleles have been referred to in the literature as either neutral or non-paramutagenic. Table 1 contains a summary of the loci, the paramutagenic and paramutable alleles and the tissues where paramutation is typically monitored at each locus.

TABLE 1

Summary of Loci Discussed

| Locus | Paramutable Form | Paramutagenic Form | (Strength) | Tissue Where Paramutation Monitored |
|---|---|---|---|---|
| r1 | R-r:std | R-r:std[a] | (weak) | aleurone of seeds |
| r1 | R-d | R-d[a] | (weak) | aleurone, coleoptile and roots of seedlings |

TABLE 1-continued

Summary of Loci Discussed

| Locus | Para-mutable Form | Para-mutagenic Form | (Strength) | Tissue Where Paramutation Monitored |
|---|---|---|---|---|
| r1 | | R-st, R-sc[b] | (strong) | aleurone of seeds |
| r1 | | R-mb, R-scm[c] | (strong) | aleurone of seeds |
| b1 | B-I | B' | (strong) | epidermal cells in most vegetative tissues, auricle in seedlings, pericarp, cob |
| pl1 | Pl-Rh | Pl' | (strong) | anthers, first leaf sheath of young seedling, epidermal cells in most vegetative tissues |

[a]The paramutable alletes, R-r:std and R-d become weakly paramutagenic after being heterozygous with strongly paramutagenic alleles.

Paramutation Phenotypes

Figure 1B:
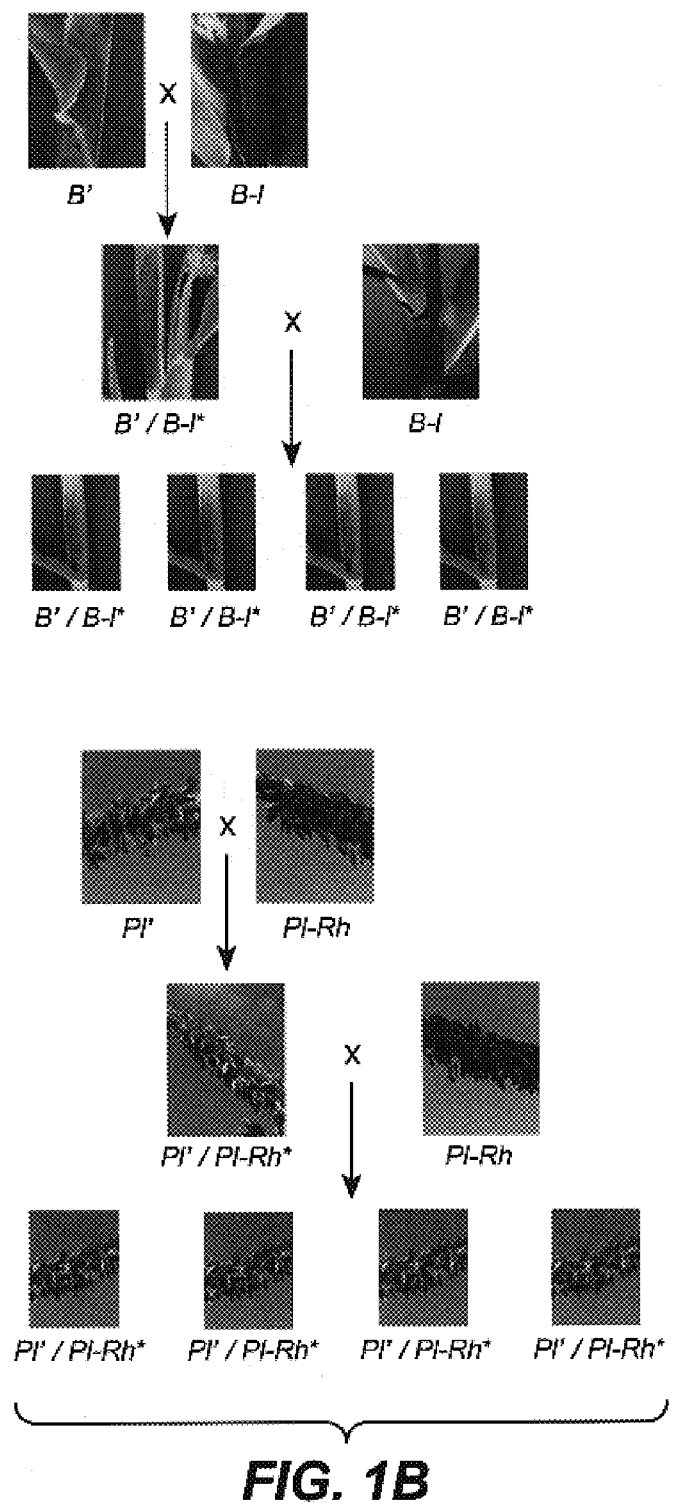
FIG. 1B shows plant and anther phenotypes of b1 and pI1 alleles, respectively. Plant phenotypes of the parents are shown in the top panels, and the F1 in the left middle panels, directly below the parents. The progeny resulting from crosses of F1plants back to paramutable alleles are shown in the bottom panels. The only genotype that segregates is B' or PI'. The asterisk is used to indicate the newly paramutagenic allele, which is fully capable of altering a paramutable allele.

Paramutation was first studied with the paramutable R-r: standard (R-r:std) haplotype, which pigments seed and plant parts. In R-r:std, seed pigmentation is considerably more sensitive to paramutation than plant pigmentation (Brink and Mikula 1958), while in another paramutable haplotype that pigments both seed and plant parts, R-d:Catspaw (R-d), both seed and plant pigmentation levels are sensitive to paramutation (Brink et al., 1970). Haplotype is used to describe the particular r1 "alleles", because all are complex containing multiple genes, resulting in the classic definition of allele being Baser inaccurate. In the most extensively studied r1 haplotypes, neither plant nor seed expression is markedly reduced in F1 plants (FIG. 1A). Consequently, silencing of paramutable r1haplotypes typically is monitored by crossing the F1 plants with null, recessive testers and analyzing kernel pigment levels in the progeny. The phenotype is strongest if the F1 is used as male. The fact that many, but not all, paramutable r1 haplotypes also undergo genomic imprinting (reflected in weaker pigment expressed in the endosperm if transmitted through the male) increases the sensitivity of this assay. Paramutagenic r1 haplotypes, R-stippled (R-st) and R-marbled (R-mb), are expressed in seeds, although both alleles also are expressed in the scutellum and coleoptile tip. Seed phenotypes of parental, F1 and testcross progeny are shown in FIG. 1A for R-st, R-mb and R-r:std. At b1 and pl1 reduced expression is always seen in the F1 and the reduced expression is always transmitted to progeny (Coe, 1966; Hollick et al., 1995). The F1 plants typically have the phenotype of the paramutagenic B' or Pl' alleles. FIG. 1B shows the phenotypes of parental, F1 and progeny plants undergoing paramutation at b1 and pl1.

Following meiosis, paramutant alleles retain the reduced expression state as discussed above and are themselves paramutagenic; they induce reduced expression of naive (not previously exposed to paramutagenic alleles) paramutable alleles in subsequent heterozygotes. At r1, a paramutable haplotype is changed into a weakly paramutagenic haplotype after it segregates from the paramutagenic haplotype. In the r1 literature, this is termed secondary paramutation to distinguish it from the stronger paramutagenicity seen with R-st and R-mb. After one generation of heterozygosity with R-st, the paramutagenicity of R-r:std' is considerably weaker than the paramutagenicity of R-st (Brown and Brink, 1960). In contrast, at the b1 and pl1 loci, newly altered paramutagenic alleles (B' or Pl') are strongly paramutagenic. They induce heritable silencing (paramutagenicity) of paramutable alleles indistinguishably from the parental paramutagenic alleles (Coe, 1966; Hollick et al., 1995). This led Coe to describe the phenomenon at b1 as a conversion event (Coe, 1959).

Two assays are routinely used to monitor paramutation: 1) the ability of a paramutagenic allele to cause a heritable reduction in the expression of a paramutable allele; and 2) the heritable alteration of the paramutant allele into a paramutagenic allele. At b1 and pl1 these two phenotypes always occur simultaneously and completely. In contrast, at r1 the extent of paramutagenicity obtained by a paramutant haplotype depends on the circumstances of the crosses, as discussed in detail in Chandler, et al., (2000).

Structures of Paramutable and Paramutagenic Alleles

Figure 2A:
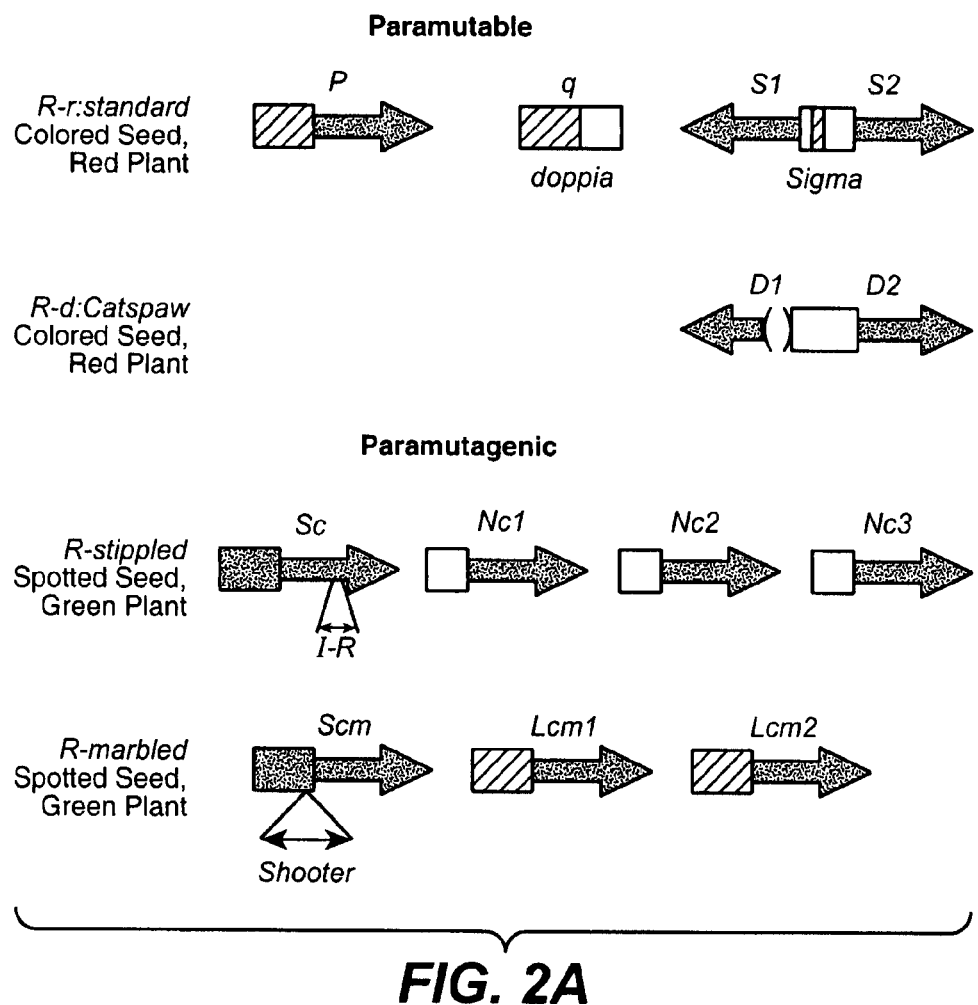
FIG. 2A shows the structure of the r1 genes within paramutable, R-r:standard and R-d:Catspaw, and paramutagenic haplotypes, R-stippled and R-marbled. The doppia sequences are indicated by the open boxes. The distance between the r1 genes is not indicated. The approximate size and location of the transposable elements in R-st and R-mb are indicated by triangles.

Paramutagenic and paramutable r1 haplotypes share r1 coding sequences and parts of the promoter regions, but these coding and promoter regions are arranged in structurally distinct ways (FIG. 2A). The paramutagenic alleles at ri are readily distinguishable from the paramutable alleles; by these structural differences and by distinct expression patterns (FIG. 1A). The paramutable alleles R-r:std and R-d each contain inverted duplications of r1 coding regions (S1/S2 and D1/D2) flanking a region called Sigma. In R-r:std, Sigma is the seed-specific promoter for the S1 (seed1) and S2 (seed2) genes in R-r:std (Walker et al., 1995). Sigma in R-r:std contains rearranged pieces of sequences that have structural features common to transposable elements (these have been named doppia, and are indicated by open boxes in FIG. 2A) together with a small amount of sequence homologous to the P (plant) promoter (indicated in FIG. 2A as hatched areas; Walker et al., 1995). In R-d, Sigma contains only doppia-related sequences (R. Okagaki and J. Kermicle, Genbank U93178). The Sigma regions are located at the same sites relative to S2 and D2 in R-r:std and R-d, respectively (FIG. 2A), but some sequences of D1 are missing relative to SI (Walker et al., 1995; R. Okagaki and J. Kermicle, Genbank U93178), suggesting that the alleles may have arisen by independent events from a common progenitor. Additionally, R-r:std contains an r1 promoter region denoted q adjacent to a second doppia-related sequence between S1 and P. Ten kbp of sequence separates q from S1 and 190 kbp of sequence separate q and P (Robbins et al, 1991, Walker et al., 1995). In R-r:std, S1/S2 are expressed only in the seed, P in vegetative parts of the plant and q not at all since it is lacking an r1 coding region (Walker et al., 1995). The q sequences are structurally very similar to the P promoter region (Walker et al., 1995), and when linked to an r1 coding region by unequal crossing over, activate expression in the same plant parts as P (Dooner, 1979; J. Kermicle, M. Alleman and W. Eggleston, unpublished data). In R-d, D1/D2 are expressed in both plant and seed (Bray and Brink, 1966; R. Okagaki and J. Kermicle, personal communication).

Both well-studied paramutagenic haplotypes contain multiple r1 genes (FIG. 2A) with distinct patterns of expression. The paramutagenic haplotype R-st contains four r1genes in direct orientation (Eggleston et al., 1995). Three distinct r1 genes were cloned from the R-mb haplotype (Panavas et al., 1999). Quantitative analysis of the products of unequal recombination of R-mb demonstrates that this haplotype contains the three cloned r1 genes organized in direct repeats (Neal, 1998; M. Alleman, personal communication) as inferred by Panavas et al., (1999).

The Sc (self color) and Scm (self color marbled) genes in R-st and R-mb, respectively (FIG. 1A), pigment the aleurone, scutellum and tip of the coleoptile in dried seeds, although Scm has much higher scutellurn and coleoptile pigment than does Sc (A. Eggleston, M. Alleman, J. Kermicle and W. Eggleston, unpublished data). Scm but not Sc also pigments the scutellar node of germinating seeds (A. Eggleston, M. Alleman and W. Eggleston, unpublished data). The I-R transposable element within Sc, and the Shooter element within Scm, cause the stippled and marbled phenotypes, respectively (Eggleston et al., 1995; Panavas et al., 1999). Full purple color is observed when the elements are lost by excision, gene conversion or unequal crossing over. The full color haplotypes are referred to as R-sc and R-scm. Neither I-R nor Shooter significantly contributes to paramutagenicity; losses of I-R from R-st and Shooter from R-mb by excision or gene conversion events that maintain the number of r1 genes have no effect on paramutagenicity (Kermicle et al., 1995; Quinn, 1999; J. Kermicle and W. Eggleston, unpublished data).

In addition to the highly expressed Sc and Scm genes, both R-st and R-mb contain additional r1 genes with distinct expression patterns. The Nc (near colorless) genes in R-st (FIG. 2A) are weakly expressed in the aleurone of seeds (Eggleston et al., 1995). The Lcm (Lc-like marbled) genes in R-mb do not contain functional promoters as they are not expressed in any tissue unless linked to a different, active promoter. Intriguingly, each Nc gene in R-st contains a doppia sequence in the promoter-proximal region in the same relative orientation and position as the doppia sequences in Sigma adjacent to S2 and D2 in R-r:std and R-d (W. Eggleston, unpublished data; Matzke et al., 1996). However, the doppia sequences are unlikely to be necessary for paramutagenicity as the Lcm genes in R-mb do not contain doppia or Sigma sequences in their promoter proximal regions (Panavas et al., 1999; J. Kermicle and W. Eggleston, unpublished data).

Figure 2B:
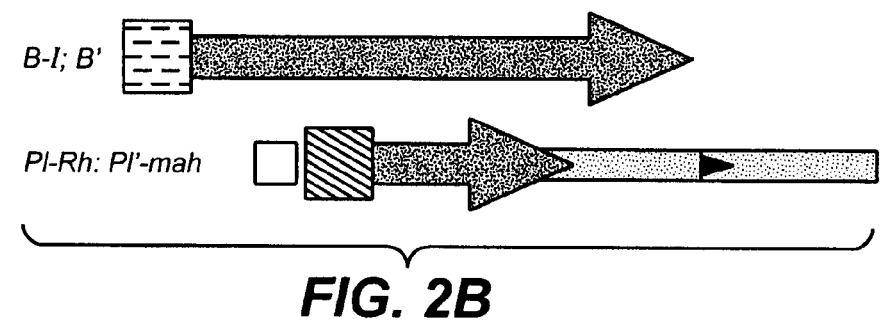
FIG. 2B shows the structure of the b1 and pI1 alleles that undergo paramutation. The 3' end of the transcribed region of pI1 is part of a repeat containing the 3' flanking region. The location of the doppia related sequences in PI' and PI-Rh is indicated by an open box.

In contrast to r1, where paramutable and strongly paramutagenic haplotypes are structurally distinct, the b1 and pl1 paramutagenic alleles arose through spontaneous changes of paramutable to paramutagenic alleles. Extensive restriction map analyses comparing the paramutable and paramutagenic forms of these alleles have identified no distinguishing differences (DNA insertions, deletions or other rearrangements) between the two types. The regions examined include ~25 kbp spanning the 4 kbp be coding region (Patterson et al., 1993) and –10 kbp spanning the 1 kbp pl1 coding region. The structures of these alleles are shown in FIG. 2B. In pl1 there is a region of 290 bp that shares sequence similarity with doppia, located upstream of the transcription initiation site. However, this sequence is not sufficient for pl1 paramutation as it is found in non-paramutagenic alleles as well (reviewed in Hollick et al., 1997). No doppia sequences have been detected in any b1 allele (V. Chandler, unpublished data).

Paramutation Can Occur Spontaneously

Paramutable alleles of all three loci, B-I, Pl-Rh, and R-r:std, are inherently unstable, as they change to lower expression states even in the absence of paramutagenic alleles. However, whether the reduced expression correlates with the simultaneous acquisition of paramutagenicity differs significantly among the loci. At b1, spontaneous changes of B-1 to B' occur at high frequencies (often 1–10%), and are readily detected as lightly colored sectors within a B-I plant or lightly pigmented B' progeny arising from homozygous B-I plants (Coe, 1966). Spontaneously derived B' alleles are as fully paramutagenic as B' alleles segregating from B'/B-I plants. Thus, the lower expression state associated with B' is invariably associated with strong paramutagenicity that results in paramutation when crossed with paramutable alleles (Coe, 1966). At pl1 spontaneous changes of Pl-Rh to Pl' also occur at high frequencies, but there is variation in the expression levels and paramutagenic strength of the spontaneous derivatives (Hollick et al., 1995). Alleles with the most reduction in expression are strongly paramutagenic, while alleles with intermediate expression are weakly paramutagenic (Hollick et al., 1995; Hollick et al., 2000). Spontaneous changes to lower gene expression states do occur with paramutable r1 alleles, but these states are not heritable nor are they associated with acquisition of strong paramutagenicity (Brink et al., 1968).

Expression Levels are Influenced by Allele Interactions

The stability of the expression states differs for the b1, pl1 and r1 loci. The paramutable B-I allele is extremely unstable when homozygous, changing into B' at very high frequencies, whereas when B-I is heterozygous with alleles that do not participate in paramutation it is much more stable (Coe, 1966; V. Chandler and K. Kubo, unpublished data). The paramutant, now paramutagenic allele, B', is very stable as it has not been found to change back to a highly expressed, paramutable form in standard maize stocks (Coe, 1966; Patterson et al., 1995), independent of whether it is carried homozygous or heterozygous with other alleles. In contrast to the stability of B', paramutant Pl' and R' are metastable. Their expression states fall within a wide continuum of levels in subsequent generations. The frequency and direction of changes depend on whether they are maintained as homozygotes or heterozygotes and the nature of the other allele, as reviewed in Chandler et al. 2000.

Paramutation Occurs in Somatic Cells

The light color phenotype and low levels of b1 or pl1 RNA in F1 individuals containing paramutagenic and paramutable alleles, combined with the spontaneous change from B-I to B' or Pl-Rh to Pl' in somatic cells, suggest b1 and pl1 paramutation occurs in somatic cells (reviewed in Chandler et al., 1996). Several lines of evidence also suggest that paramutation at r1 occurs somatically. Sastry et al. (1965) showed that individual tassel branches of a single plant transmitted distinct expression states, demonstrating somatic sectors. Treatment of F1 seeds with irradiation (Shih and Brink, 1969) or alkylating agents (Axtell and Brink, 1967; Brink et al., 1968) results in significant reductions in paramutation. Further, r1 paramutation is significantly impacted by altering the environmental conditions of young F1 seedlings at times well before meiosis (Mikula, 1995).

Genetic Strategies to Identify Trans-acting Components Required for Paramutation.

To understand the underlying mechanisms that control paramutation, an example of gene silencing, it will be essential to identify the molecular machinery responsible for the establishment and maintanence of paramutation. This invention is directed to the use of several mutational approaches to identify trans acting components required for paramutation.

Mutations were isolated from several distinct genetic screens (described below) designed to identify mutations that cause increase pigment production in B'/B' and/or Pl'/Pl' plants. Mutations identified in screens using the B'/B' system are designated mop mutations for mediator of paramutation and those identified in screens using Pl'/Pl' materials are designated rmr mutations for required to maintain repression. There are at least two putative functions for the mop and rmr gene products; 1) they could be required to establish paramutation, 2) they could be required to maintain gene repression previously established by paramutation. The genes could also be required for both establishment and maintenance of paramutation. In addition, rmr and mop gene products could either be required to maintain repressed gene expression only during somatic development or they could be required to ensure that the repressed expression state is also transferred to progeny (maintained through meiosis, gametophyte development, fertilization and embryo development). Distinctive seedling and plant pigment phenotypes facilitate genetic screens for mutations that alter either the establishment or the maintenance of paramutation. Screens have been developed using either the b1 (Example 1) or the pl1 system (Example 3). Both transposon (Example 1) and EMS mutagenesis (Example 3, 6) have been utilized. The extreme penetrance of b1 and pl1 paramutation (it always occurs) together with the stability of the paramutant state at both loci make these powerful screens. The basic approach is to mutagenize the parent containing the paramutagenic allele, cross to the paramutable allele, and then screen the resulting M1 generation for rare dominant mutants that prevent the establishment of paramutation. These are identified as rare dark seedlings or plants among lightly pigmented siblings. To screen for recessive mutations that fail to maintain the reduced expression state associated with paramutation, M1 plants are self-pollinated and the resulting M2 are screened for darkly pigmented seedlings or plants. The background for the b1 screen is extremely low, as the only two dark exceptions in the approximately 10,000 M1 B'/B-I plants screened were subsequently shown to be dominant or semi-dominant mutants. The background with the pl1 screen is higher, as the examination of approximately 50,000 M1 individuals, revealed 0.2% dark seedlings that when grown to maturity had light PI' anthers, so were not true mutants. To date 16 independent mutations have been identified that relieve the gene silencing associated with the paramutant state (described in detail in Examples below).

Phenotypes of Corn Mutants with Reduced Gene Silencing Activity

Several methods have been used to characterize the various mutant alleles isolated from these genetic screens. 1) Genetic complementation tests establish potential allelism (determines the number of unique genes identified) and reveal potential genetic interactions between different genes. 2) RNA levels of B', PI' or both, are determined in the mutants and compared to wild type siblings. 3) The relative impact each mutation has on maintaining the silenced expression state of B', PI' or both, is determined by monitoring the stability of the reduced expression state in progeny from outcrosses. 4) Genetic experiments are done to assess the ability of the mutations to prevent the establishment of paramutation at b1, r1 and pl1.5) Phenotypic analysis compares the relative impact each mutation has on normal maize plant growth and development. 6) The ability of the mutants to affect other epigenetic phenomena such as transposon methylation and transgene silencing is tested.

Plant Breeding

The goal of field crop breeding is to combine various desirable traits in a single variety/hybrid. The reduced gene silencing traits of the mutant corn lines of the present invention can be introduced into corn breeding programs in order to prevent the establishment or maintenance of gene silencing in new corn lines.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (Zea mays L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. Here, the mutant plants of the invention have been selfed and selected for the absence of gene silencing.

A cross between two homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants such as the mutant plants of this invention or various other broad-based sources into breeding pools from which new inbred plants are developed by selfing and selection of desired phenotypes. The new inbreds are crossed with other inbred plants and the hybrids from these crosses are evaluated to determine which of those have commercial potential.

Pedigree Breeding

The pedigree breeding method involves crossing two genotypes. In this invention, one genotype would be a mutant corn plant of the invention. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection.

Backcrossing can also be used to improve an inbred plant. Backcrossing transfers a specific desirable trait from one inbred or non-inbred source to an inbred that lacks that trait. In this invention, the reduced gene silencing activity trait of the corn lines of the invention can be transferred to another corn line. This can be accomplished, for example, by first crossing a superior inbred (A) (recurrent parent) to a donor inbred (non-recurrent parent), which carries the appropriate locus or loci for the trait in question. In the present invention, the mutants of the invention would serve as the donor stock either in inbred or non-inbred genetic backgrounds. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

A single cross hybrid corn variety is the cross of two inbred plants, each of which has a genotype that complements the genotype of the other. The hybrid progeny of the first generation is designated F1. Typically, F1 hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the F1 hybrid plants are typically sought. An F1 single cross hybrid is produced when two inbred plants are crossed. A double cross hybrid is produced from four inbred plants crossed in pairs (A×B and C×D) and then the two F1 hybrids are crossed again (A×B)×(C×D).

Development of F1 Lines

The development of a hybrid corn variety generally involves three steps: (1) the selection of plants from various germplasm pools such as the mutant corn plants of the invention; (2) the selfing of the selected plants for several generations to produce a series of inbred plants, which, although different from each other, each breed true and are highly uniform; and (3) crossing the selected inbred plants with unrelated inbred plants to produce the hybrid progeny (F1). During the inbreeding process in corn, the vigor of the plants decreases. Vigor is restored when two unrelated inbred plants are crossed to produce the hybrid progeny (F1). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by F1 hybrids is lost in the next generation (F2). Consequently, seed from hybrid varieties is not used for planting stock. It is not generally beneficial for farmers to save seed from F1 hybrids. Rather, farmers purchase F1 hybrid seed for planting every year.

In selecting a second plant to cross with the mutant corn plants of the invention for the purpose of developing novel inbred lines, it will typically be desired to choose those plants which either themselves exhibit one or more selected desirable characteristics or which exhibit the desired characteristic(s) when in hybrid combination. Examples of potentially desired characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size. Alternatively, the mutant corn plants of the invention may be crossed with a second, different inbred plant for the purpose of producing hybrid seed that is sold to farmers for planting in commercial production fields. In this case, a second inbred variety is selected which confers desirable characteristics when in hybrid combination with the first inbred line.

In a preferred embodiment, crossing comprises the steps of: (a) planting in pollinating proximity seeds of a first and a second parent corn plant, and preferably, seeds of a first inbred corn plant and a second, distinct inbred corn plant; (b) cultivating or growing the seeds of the first and second parent corn plants into plants that bear flowers; (c) emasculating flowers of either the first or second parent corn plant, i.e., treating the flowers so as to prevent pollen production, or alternatively, using as the female parent a male sterile plant, thereby providing an emasculated parent corn plant; (d) allowing natural cross-pollination to occur between the first and second parent corn plants; (e) harvesting seeds produced on the emasculated parent corn plant; and, (f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that the mutant plants of the invention are employed as the male parent, the tassels of the other parental plant are removed from all e plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of ROUNDUP□ herbicide in combination with glyphosate tolerant maize plants to produce male sterile corn plants is disclosed in PCT Publication WO 98/44140.

Following emasculation, the plants are then typically allowed to continue to grow and natural cross-pollination occurs as a result of the action of wind, which is normal in the pollination of grasses, including corn. As a result of the emasculation of the female parent plant, only the pollen from the male parent plant is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental inbred plants of corn may be allowed to continue to grow until maturity or the male rows may be destroyed after flowering is complete. Only the ears from the female inbred parental plants are harvested to obtain seeds of a novel F1 hybrid. The novel F1 hybrid seed produced can then be planted in a subsequent growing season in commercial fields or, alternatively, advanced in breeding protocols for purposes of developing novel inbred lines.

In the present invention, the mutant corn lines of the present invention can be used as inbred lines. It is more likely, however, that the mutant lines of this invention will be used in breeding programs to introduce the gene silencing repression traits into other lines. The gene silencing repression traits may be introduced into other lines by the use of single locus conversion.

Single Locus Conversions

When the term inbred corn plant is used in the context of the present invention, this also includes any single locus conversions of that inbred. The term single locus converted plant as used herein refers to those corn plants that are developed by a plant breeding technique called backcrossing wherein essentially all of the desired morphological and physiological characteristics of an inbred are recovered in addition to the single locus transferred into the inbred via the backcrossing technique. Backcrossing methods can be used with the present invention to improve or introduce a characteristic such as reduced gene silencing activity into the inbred. The term backcrossing as used herein refers to the repeated crossing of a hybrid progeny back to one of the parental corn plants for that inbred. The parental corn plant that contributes the locus or loci for the desired characteristic is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol. In a typical backcross protocol, the original inbred of interest (recurrent parent) is crossed to a second nonrecurrent parent stock (inbred or otherwise) that carries the single locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred locus from the nonrecurrent parent. The backcross process may be accelerated by the use of molecular markers, such as RFLP, SSLP, SNP or AFLP markers to identify plants with the greatest genetic complement from the recurrent parent, but retaining the single locus of interest.

The goal of a backcross protocol is to alter or substitute a single trait or characteristic such as repression of gene silencing or reduced gene silencing activity in the original inbred. To accomplish this, a single locus of the recurrent inbred is modified or substituted with the desired locus from the nonrecurrent parent, while retaining essentially all of the rest of the desired genetic, and therefore the desired physiological and morphological constitution of the original inbred. Here, the mutants with reduced gene silencing can be used as the nonrecurrent parent. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred. It may also be possible to follow transfer of the allele with reduced gene silencing properties using tightly linked molecular markers, such as SSLP or RFLP.

Tissue Cultures and in Vitro Regeneration of Corn Plants

A further aspect of the invention relates to tissue cultures of the mutant corn plants of the invention. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. Nos. 5,538,880; and 5,550,318, each incorporated herein by reference in their entirety). By way of example, a tissue culture comprising organs such as tassels or anthers has been used to produce regenerated plants (U.S. Pat. Nos. 5,445,961 and 5,322,789; the disclosures of which are incorporated herein by reference).

Tassel/Anther Culture

Tassels contain anthers that in turn enclose microspores. Microspores develop into pollen. For anther/microspore culture, if tassels are the plant composition, they are preferably selected at a stage when the microspores are uninucleate, that is, include only one, rather than 2 or 4 nuclei. Methods to determine the correct stage are well known to those skilled in the art and include mitramycin fluorescent staining, trypan blue and acetocarmine squashing. The mid-uninucleate microspore stage has been found to be the developmental stage most responsive to the subsequent methods disclosed to ultimately produce plants.

Lines For Crossing

The mutant corn lines of the invention may be crossed with any other suitable corn plants. Such suitable corn plants generally include commercially useful traits.

Deposit Information

Representative of, but not limiting the invention, Applicants have deposited the following seeds with the American Type Culture Collection.

Applicants have made available to the public without restriction a deposit of at least 2500 seeds of corn mop1-1 with the American Type Culture Collection (ATCC), 10801 University Blvd., Manassas. Va. 20108, which has been assigned ATCC number PTA-3828 and deposited on Nov. 6, 2001.

Applicants have made available to the public without restriction a deposit of at least 2500 seeds of corn Mop1-2EMS with the American Type Culture Collection (ATCC), 10801 University Blvd., Manassas, Va. 20108, which has been assigned ATCC number PTA-3826 and deposited on Nov. 6, 2001.

Applicants have made available to the public without restriction a deposit of at least 2500 seeds of corn Mop2-1 with the American Type Culture Collection (ATCC), 0801 University Blvd., Manassas, Va. 20108, which has been assigned ATCC number PTA-4030 and deposited on Feb. 4, 2002.

Applicants have made available to the public without restriction a deposit of at least 2500 seeds of corn mop3-1 with the American Type Culture Collection (ATCC), 10801 University Blvd., Manassas, Va. 20108, which has been assigned ATCC number PTA-3829 and deposited on Nov. 6, 2001.

Applicants have made available to the public without restriction a deposit of at least 2500 seeds of corn CC2343 with the American Type Culture Collection (ATCC), 10801 University Blvd., Manassas, Va. 20108, which has been assigned ATCC number PTA-3827 and deposited on Nov. 6, 2001.

Applicants have made available to the public without restriction a deposit of at least 2500 seeds of corn rmr1-1 with the American Type Culture Collection (ATCC), 10801 University Blvd., Manassas, Va. 20108, which has been assigned ATCC number PTA-3965 and deposited on Jan. 8, 2001.

Applicants have made available to the public without restriction a deposit of at least 2500 seeds of corn rmr1-2 with the American Type Culture Collection (ATCC), 10801 University Blvd., Manassas, Va. 20108, which has been assigned ATCC number PTA-3966 and deposited on Jan. 8, 2001.

Applicants have made available to the public without restriction a deposit of at least 2500 seeds of corn rmr2-1 with the American Type Culture Collection (ATCC), 10801 University Blvd., Manassas, Va. 20108, which has been assigned ATCC number PTA-3956 and deposited on Jan. 8, 2001.

Applicants have made available to the public without restriction a deposit of at least 2500 seeds of corn rmr7-1 with the American Type Culture Collection (ATCC), 10801 University Blvd., Manassas, Va. 20108, which has been assigned ATCC number PTA-3958 and deposited on Jan. 8, 2001.

Applicants have made available to the public without restriction a deposit of at least 2500 seeds of corn rmr6-1 with the American Type Culture Collection (ATCC), 10801 University Blvd., Manassas, Va. 20108, which has been assigned ATCC number PTA-3957 and deposited on Jan. 8, 2001.

Applicants have made available to the public without restriction a deposit of at least 2500 seeds of corn rmr8-1 with the American Type Culture Collection (ATCC), 10801 University Blvd., Manassas, Va. 20108, which has been assigned ATCC number PTA-3960 and deposited on Jan. 8, 2001.

Applicants have made available to the public without restriction a deposit of at least 2500 seeds of corn rmr9-1 with the American Type Culture Collection (ATCC), 10801 University Blvd., Manassas, Va. 20108, which has been assigned ATCC number PTA-3961 and deposited on Jan. 8, 2001.

Applicants have made available to the public without restriction a deposit of at least 2500 seeds of corn Mop1-4 with the American Type Culture Collection (ATCC), 10801 University Blvd., Manassas, Va. 20108, which has been assigned ATCC number PTA-3963 and deposited on Jan. 8, 2001.

Applicants have made available to the public without restriction a deposit of at least 2500 seeds of corn Mop1-5 with the American Type Culture Collection (ATCC), 10801 University Blvd., Manassas, Va. 20108, which has been assigned ATCC number PTA-3964 and deposited on Jan. 8, 2001.

Applicants have made available to the public without restriction a deposit of at least 2500 seeds of corn rmr7-2 with the American Type Culture Collection (ATCC), 10801 University Blvd., Manassas, Va. 20108, which has been assigned ATCC number PTA-3959 and deposited on Jan. 8, 2001.

Applicants have made available to the public without restriction a deposit of at least 2500 seeds of corn rmr11-1 with the American Type Culture Collection (ATCC), 10801 University Blvd., Manassas, Va. 20108, which has been assigned ATCC number PTA-3962 and deposited on Jan. 8, 2001.

The deposits will be maintained in the ATCC depository, which is a public depository, for a period of 30 years, or 5 years after the most recent request, or for the enforceable life of the patent, whichever is longer, and will be replaced if a deposit becomes nonviable during that period. Access to this deposit will be available during the pendency of the application to the Commissioner of Patents and Trademarks and persons determined by the Commissioner to be entitled thereto upon request. Additionally, Applicant has satisfied all the requirements of 37 C.F.R. .sctn..sctn.1.801–1.809, including testing by the ATCC upon receipt of the deposit demonstrating viability of the deposited seeds.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

EXAMPLES

Example 1

Isolation of Mop1-1 Mutant Plant

General. Paramutation is an interaction between two specific alleles, which leads to a heritable alteration in one of the alleles at a very high frequency. Paramutation was first described at the r1 locus of maize (Brink, 1956; Brink, 1958). Brink observed that aleurone pigment levels in genotypically identical kernels (triploid endosperm R-r/R-g/R-g) were significantly different, dependent upon whether R-r was previously homozygous or heterozygous with R-stippled (R-st). R-st (termed paramutagenic) induced a heritable reduction in the expression of standard R-r (termed paramutable); altered R-r is designated R-r' (reviewed in Kermicle, 1996). The paramutable b1 and pl1 alleles are B-I and PI-Rh respectively, and when heterozygous with a paramutagenic B' or Pl' allele, the paramutable allele is heritably changed into a paramutagenic allele (Coe, 1966; Hollick et al., 1995). The paramutable B-I and PI-Rh alleles are also unstable, spontaneously changing to B' and PI' (Coe, 1966; Hollick et al., 1995). Most alleles of b1, r1 and pl1 do not participate in paramutation and are termed neutral. Paramutation-like phenomena are not restricted to pigment regulatory genes; they have also been described in other plants (reviewed in Brink, 1973), and with transgenes in Petunia and tobacco (Meyer et al., 1993; Matzke et al., 1994; reviewed in Hollick et al., 1997).

Paramutation has been extensively characterized at three maize loci: r1, b1, and pl1 (For review see Chandler et al., 2000). b1 and r1 encode functionally interchangeable basic-helix-loop-helix (bHLH) factors (Styles et al., 1973; Ludwig et al., 1989; Goff et al., 1990; Radicella et al., 1991), whereas pl1 encodes a myb-related transcription factor (Cone et al., 1993). Activation of the anthocyanin biosynthesis pathway requires co-expression of a bHLH factor and a myb-related factor (Goff et al., 1992). In general, the pl1 locus is expressed in the plant, whereas its functional equivalent, c1, is expressed in the embryo and the aleurone layer of the kernel endosperm. Therefore, when functional alleles of pl1 and c1 are present, it is generally the b1 and r1 alleles present that determine the tissue-specific patterns of anthocyanin expression (Styles et al., 1973).

Plant Stocks. All plant stocks contained dominant functional alleles for all the genes encoding the anthocyanin biosynthetic enzymes required in vegetative plant tissues. Because transcription of these genes in vegetative plant tissues is controlled by pI1 in combination with b1 or r1, the specific b1, pI1 and r1 alleles are indicated for relevant stocks. One exception is the distinction between PI'-mahogany (PI') and PI-Rhoades (PI-Rh) (Hollick et al., 1995). Many stocks possess the R-g allele of r1 (no expression in the seed or plant), which precludes reliable scoring of PI' versus PI-Rh. In these stocks, we have used PI' to indicate the presence of either PI-Rh, or its spontaneous derivative PI'.

Though stocks containing various b1 alleles have been maintained in the laboratory of Vicki Chandler (now at the University of Arizona) for several years, they were originally obtained from a variety of sources: B-I PIR-g (inbred W23 background), B' PIR-g (inbred K55 background), and b1-K55 PIR-g (inbred K55 background) stocks from E. H. Coe, Jr. (University of Missouri, Columbia), B-bar from E. D. Styles (University of Victoria), and B-Peru (inbred W22 background) from G. Neuffer (University of Missouri). Jay Hollick and Vicki Chandler have maintained PI-Rh and PI'-mahogany stocks originally obtained from E. H. Coe, Jr. and additional PI-Rh stocks from the Maize Cooperation Stock Center. J. L. Kermicle has maintained the R-stippled (R-st), R-r:standard (R-r:std, a specific accession of R-r, also known as standard R-r), and R-d:Catspaw (R-d) stocks (each containing B-bar and pI-W22, inbred W22 background) established by R. A. Brink and colleagues.

Genetic Screen. A B-I PIR-g stock was used to generate a B-I PIR-g Mu stock by sequential backcrosses into active Mutator stocks (Patterson et al., 1991). The B-I PIR-g Mu stock, carrying functional alleles for all of the anthocyanin biosynthetic enzymes, was crossed to B' PIR-g (inbred W23 background). The B' allele in this stock was a spontaneous derivative of the B-I allele obtained from E. H. Coe, Jr. F1 individuals between B' and B-I Mu were self-pollinated to generate F2 families. F2 families were screened in sand benches for rare darkly-pigmented seedlings resembling B-I-like plants among siblings that were essentially green. The mediator of paramutation1-1 (Mop1-1) mutation was isolated from this screen.

Genetic Crosses. In the crosses that follow, a single allele listing indicates homozygosity, whereas heterozygous individuals are indicated with alleles separated by a slash (/). In some instances, the identity of one (dominant) allele is known, but the second allele could be either of two possibilities (e.g. B'/I–). The term "family" refers to plants grown from kernels on the same ear, all of which share a common tassel parent. To characterize homozygous Mop1-1 plants relative to heterozygous siblings, families segregating Mop1-1 were generated as follows: B' PIR-g Mop1-1 plants were crossed to B' PIR-g Mop1, and the resulting F1 plants backcrossed to B' PIR-g Mop1-1 plants. Unless otherwise noted, all comparisons between Mop1-1/Mop1-1 and Mop1/Mop1-1 siblings derive from families generated in this way. One exception is the individuals used to assay the methylation levels of repeated sequences. The sibling individuals compared in this experiment derived from a backcross of B'/b1-A188 PI/pI-sr R-r/R-g Mop1/Mop1-1 with homozygous B'PIR-g Mop1-1.

To test whether Mop1-1 affects the paramutant PI' allele, B' PIR-g Mop1-1 plants were crossed to a b1-W23 PI' R-r stock, and F1 individuals were self-pollinated. Additional segregating families were generated by intercrossing light- and dark-anthered siblings. The inheritance of PI' was assayed from four Mop1-1/Mop1-1 individuals derived directly from the self-pollinated F1 individuals. Additional tests were done using individuals from segregating families derived from PI' Mop1/Mop1-1 crossed by PI' Mop1-1/Mop1-1. Tests from these families totaled seven PI' Mop1-1/Mop1-1 and three PI' Mop1/Mop1-1 individuals. The inheritance of PI' was tested by crosses with a variety of PI-Rh tester stocks.

To test whether Mop1-1 influences the expression of other b1 alleles, B' PIR-g Mop1-1 plants were crossed to a B-Peru PIR-g Mop1 stock (inbred W22 background), and the F1 plants were self-pollinated. Purple kernels were planted (B-Peru/–), and homozygous B-Peru individuals produced ears with 100% purple kernels. All F2 individuals were testcrossed with B' PIR-g Mop1-1 to determine the Mop1 genotype. B-bar stocks were derived as follows: B-bar pI-W22 R-r Mop1 (inbred W22 background) were crossed with B' PIR-g Mop1-1; the F1 was self-pollinated; dark progeny (B'/– Mop1-1/Mop1-1) were backcrossed with B-bar pI-W22 R-r Mop1; progeny of the backcross were self-pollinated; and dark progeny were self-pollinated again. The phenotypes of progeny from the last self-pollinations were used to discern whether Mop1-1 intensifies B-bar.

To test whether Mop1-1 has an effect on the establishment of b1 paramutation, Mop1-1 was crossed to b1-K55 PIR-g to facilitate further genetic analyses in a background independent of B'. This b1-K55 Mop1 stock was used to introduce the Mop1-1 allele into B-I stocks to test for an effect of Mop1-1 on the establishment of b1 paramutation. Three B'/B-I Mop1-1/Mop1-1 individuals were tested with one cross each to B-I/B-Peru PIR-g Mop1 stocks and with crosses to b1 tester stocks (total of four families to either b1-K55/b1-K55 or b1-K55/b1-W23 PIR-g Mop1/Mop1).

To test for an effect of Mop1-1 on the establishment of pI1 paramutation, B' PI-Rh R-r/-Mop1/Mop1-1 was crossed with B'/-PI'R-r/-Mop1/Mop1-1; and darkly-pigmented progeny (B'/– PI'/PI-Rh R-r/-Mop1-1/Mop1-1) were crossed with b1-K55 PI-Rh R-r Mop1. A total of four families representing three PI'/PI-Rh Mop1-1/Mop1-1 individuals were examined.

To test effects of Mop1-1 on the establishment of r1 paramutation, B' PIR-g Mop1-1 plants were crossed to R-st and R-d. Intercrosses between the resulting R-st and R-d progenies produced paramutagenic R-d R-st and non-paramutagenic R-d R-g heterozygotes for comparison among Mop1-1/Mop1-1 and Mop1/– classes. Because Mop1-1 does not intensify B-bar pigmentation, one in 13 plants classified as Mop1/– (light plant) is expected to be B-bar/B-bar Mop1-1/Mop1-1. Reduced paramutation in this genotype would underestimate paramutation in the control population and thus underestimate the ability of Mop1-1 to inhibit r1 paramutation. Effects on r1 paramutation were assayed with testcrosses to W23 R-g stocks (null for both aleurone and plant expression of r1) followed by measurement of kernel color using a reflectometer (Alleman and Kermicle, 1993). A similar crossing scheme was used to test effects of Mop1-1 on the paramutable R-r:std haplotype. R-r:std, also known as standard R-r, indicates that this is the specific R-r accession originally tested by Brink (1956).

Analysis of RNA Levels and Transcription Rates. RNA levels were assayed by RNase protections using actin or ubiquitin as an internal control. RNA was isolated using Trizol (Gibco/BRL) according to manufacturer's directions, with the exception that tissue was ground using liquid nitrogen in a mortar and pestle. RNase protections were performed as described in Selinger and Chandler (1999). 5 µg total RNA was used per hybridization. The actin 1 probe (5' half of exon 2), the 315 bp cDNA probe from b1, and the 438 bp cDNA probe from c2 were as described previously (Selinger and Chandler, 1999). The ubiquitin probe is a 228 bp BgIII fragment from ubi2 (Christensen et al., 1992) which encompasses one of the seven ubiquitin repeats. The pI1 probe is a 505 bp cDNA fragment which includes exons 1-2 and ends at the BgII site in exon 3 of the PI-Rh allele.

Transcription rates were determined using in vitro transcription assays on isolated nuclei. Nuclei were isolated by two independent procedures. The first method, using a hexylene glycol-based buffer and percoll for differential density purification, was based primarily upon a maize nuclei isolation protocol (Cone et al., 1993) with modifications incorporated (B. J. Janssen, personal communication) after consulting several additional sources (Spiker et al., 1983; Watson and Thompson, 1986; Paul et al., 1987; Lund et al., 1995). Leaf sheath tissue, harvested from plants approximately two weeks prior to tassel emergence, was ground with a mortar and pestle in liquid nitrogen and suspended in 160 ml nuclear extraction buffer at 4° C. (Cone et al., 1993). After filtration through two layers of cheesecloth, 1.6 ml of 25% Triton X-100 was slowly added to each sample, followed by filtration through a 53 µm nylon sheet. After filtering, samples were centrifuged in a swinging bucket rotor (10 min 4° C. 1000 g). Nuclei were resuspended in 20 ml working buffer (Cone et al., 1993) modified to contain 0.25% Triton X-100 and layered on top of 90% percoll (Cone et al., 1993) modified to contain 0.25% Triton X-100 and 10 mM MgCl2. Samples were centrifuged in a swinging bucket rotor (20 min. 4° C. 4000 g). Nuclei were recovered from the top of the 90% percoll, diluted 3-fold in nuclei wash buffer (10 mM PIPES (Piperazine-N,N'-bis[2-ethanesulfonic acid]) pH 7.0, 10 mM MgCl2, 5 mM beta-mercaptoethanol, 20% glycerol) and pelleted (15 min 4° C. 2000 g). Supernatant was decanted and nuclei were resuspended in resuspension buffer modified to contain 20% glycerol (Hollick and Gordon, 1993).

In the second method, nuclei from 7–10 grams of sheath and husk tissue from plants at anthesis was prepared using a chromatin isolation protocol (Steinmuller and Apel, 1986) with the following changes: Ground material was suspended in 15 ml isolation buffer (Steinmuller and Apel, 1986) filtered through two layers of cheesecloth followed by a 53 µm nylon sheet. Three centrifugations were performed (15 min −10° C. 6000 g). Following the first two centrifugations, crude nuclei pellets were resuspended in 15 ml isolation buffer. After the last centrifugation, crude nuclei were resuspended in 2 ml of the resuspension buffer described above.

Nuclei isolated by either method were repelleted (30 sec RT 5000 rpm using Eppendorf micro-centrifuge) and resuspended in 0.1 ml of resuspension buffer (described above). Reactions and RNA isolations were carried out as described in Hollick and Gordon (1993) with the exception that 100 µCi alpha-32p-CTP (800 Ci/mmole) was used and incubation was at 30° C. for 25 minutes. Comparable amounts of labelled RNA for each genotype were used for filter hybridization.

Slot-blots were prepared with a Minifold II slot-blot system according to manufacturer's directions (Schleicher & Schuell, Keene, N.H.) using BA85 nitrocellulose filter membrane and 100 ng per slot of purified gene fragments or equivalent amount of linearized plasmid. Ubiquitin, ~975 bp PstI fragment of ubi2 from plasmid ca210 (Christensen et al., 1992), b1, ~1970 bp from plasmid pBcDNA (Radicella et al., 1991), and c2, 1450 bp cDNA from plasmid cLC46E (Wienand et al., 1986). Strips of nitrocellulose with the slot-blotted gene fragments were pre-hybridized for 3 hours in 4 ml hybridization solution at 42° C. [5×SSPE (1×SSPE=0.15M NaCl, 0.01M Sodium phosphate, 0.001M EDTA), 0.1% polyvinyl pyrrolidine, 0.1% Ficoll, 50% formamide, 12.5 µg/ml tRNA]. Pre-hybridization solution was replaced with labelled RNA heat-denatured in 2.5 ml hybridization solution. After 60–72 hours at 42° C., strips were briefly rinsed, washed twice for 15 minutes each at 42° C. (1×SSPE, 0.1% SDS (Sodium Dodecyl Sulfate)) and once for 15 minutes at 42° C. (0.1×SSPE, 0.1% SDS).

The in vitro transcription assay filters and RNase protections were visualized using a Storm 860 PhosphorImager (Molecular Dynamics, Sunnyvale, Calif.) and signals were quantified using ImageQuaNT software. Background was subtracted from each signal prior to normalizing b1 and pI1 signals to ubiquitin or actin signals.

Analysis of Global DNA Methylation Levels. Global DNA methylation levels were assayed using methylation sensitive restriction enzymes and DNA blots. DNA was isolated from leaves (Dellaporta et al., 1983). DNA (~4 µg) was digested according to manufacturer specifications (New England Biolabs, Bethesda Research Laboratories and Pharmacia), and size-fractionated by electrophoresis in 0.8% agarose gels with 0.5×TBE (0.045M Tris-borate, 0.001 M EDTA). The DNA was transferred to charged Hybond N+ (Amersham) membrane with alkaline transfer buffer (0.4M NaOH, 0.6M NaCl). The 45S ribosomal repeat (McMullen et al., 1986; McMullen et al., 1991) and the centromere repeat from sorghum (pSau3a9; Jiang et al., 1996) were radioactively labelled using random hexamer priming (Feinberg and Vogelstein, 1983). Hybridization was performed in a rotating hybridization oven at 65° C. with 5% SDS, 50 mM PIPES pH 6.5, 50 mM NaHPO4 pH 7, 1 mM EDTA, 100 mM NaCl and 100 µg/ml salmon sperm DNA. Washes were 2 min 65□C 1×SSC/0.1% SDS, 30 min 65° C. 0.5×SSC/ 0.1% SDS, 10 min RT 0.1×SSC/0.1% SDS (1×SSC=0.15 M NaCl, 0.015 M Sodium Citrate). Blots were exposed to a phoshor-imaging screen and visualized with a Storm 860 PhosphorImager (Molecular Dynamics).

Identification and Genetic Characterization of mop1. Paramutation always occurs when B' and B-I are heterozygous, and B' is extremely stable in subsequent generations (reviewed in Chandler et al., 2000). These characteristics enable a simple genetic screen to isolate mutations affecting paramutation. Furthermore, the phenotypes of B-I and B' are readily distinguishable even in young seedlings; B-I seedlings have intense anthocyanin pigmentation, and B' seedlings have little or no anthocyanin pigmentation. A screening population was generated by crossing B' plants by B-I plants carrying active Mutator (Mu) transposable elements. F1 plants were screened for darkly pigmented (B-I-like) individuals, which could represent dominant mutations preventing the establishment of paramutation. All F1 individuals (>3500) were lightly pigmented (B'), indicating that paramutation had occurred without exception. To identify recessive mutations that may represent failure to maintain the repressed B' transcription state, F1 individuals were self-pollinated and F2 families were screened for darkly pigmented (B-I-like) seedlings segregating at ¼ frequency. Darkly anthocyanin pigmented B-I-like individuals are referred herein as dark and lightly anthocyanin pigmented B'-like individuals are referred herein as light. Several F2 families yielded dark seedlings (25 of 510 families screened). Segregation in subsequent crosses confirmed the presence of a recessive mutation at a single locus in each of these families (data not shown). The high frequency of families segregating dark seedlings was not observed in a similar screen resulting from the cross of a B' Mu stock with B-I; none of the F2 families yielded dark seedlings (zero of 427 families screened). The high frequency in one set of stocks, but not in the other, suggested that a recessive mutation had been present in some of the B-I Mu stocks used in these experiments. Consistent with this hypothesis, genetic complementation tests among plants from the 25 families yielded dark seedlings, confirming that each of these families carried a mutation in the same gene (data not shown). Pedigree analyses demonstrated that this mutation was segregating in the B-I Mu stocks. Based on subsequent analyses described below, we have designated the locus identified by this mutation mediator of paramutation1 (Mop1), and the mutant allele Mop1-1. Recessive Mop1-1 likely represents a reduced or loss of function allele; individuals heterozygous for Mop1-1 have B' pigment levels, which is defined as wild-type for this genetic background. As these individuals possess the Mop1 allele normally present in most maize stocks, we will refer to the Mop1 allele as wild-type.

Mop1-1 Alters the Phenotype of Both B' and Pl'. The fact that Mop1-1 was isolated as dark, B-I-resembling seedlings among light B' siblings indicated that Mop1-1 modified the phenotype of B' seedlings to resemble a B-I phenotype. A similar modification of the B' phenotype is observed in mature plants. FIGS. 3A and 3B show the adult phenotypes of B' Mop1/Mop1-1 and B' Mop1-1/Mop1-1 plants. FIGS. 3B and 3C illustrate the very similar phenotype of B' Mop1-1/Mop1-1 and B-I Mop1/Mop1 plants. These results are consistent with the Mop1 gene having a role in the maintenance of the paramutant B' state. Though B' Mop1-1 plants resemble B-I plants, they occasionally show somatic instability, manifest as sectors of B'-like pigmentation similar to that seen in FIG. 3D. This observation suggests that the Mop1-1 mutation is unstable and may be caused by a transposable element.

Does Mop1-1 also alter the phenotype of the paramutant Pl' allele? To address this question, it is necessary to assay the pl1 expression phenotype independent of changes in b1 expression, yet to activate the anthocyanin pathway, pl1 must be co-expressed with a bHLH factor (b1 or r1). The anthers represent a reliable tissue in which to assay pl1 expression because r1, but no b1 allele, is expressed in the anthers. Fortunately, the r1 gene expressed in the anthers does not undergo spontaneous paramutation, thus changes in anther pigment reflect changes in pl1 expression. Our homozygous B' Mop1-1 stocks lacked r1 expression in the anthers (homozygous for the null R-g allele), therefore we introduced R-r, which is expressed in both seeds and anthers. In the presence of R-r, Pl' gives variegated (light) anthers, whereas Pl-Rh gives fully-pigmented (dark) anthers. Light-anthered B'/b1-W23 Pl'/Pl' Mop1/Mop1-1 R-r/R-g individuals were self-pollinated, and purple kernels (inheriting dominant R-r) were planted. Recessive b1-W23 produces a green plant when homozygous, but b1 segregation will not affect anther pigmentation. If Mop1-1 intensifies Pl', then ¼ dark-anthered progeny are expected to segregate. Light-anthered individuals, as seen in FIG. 3E, and dark-anthered individuals, as seen in FIG. 3F, were observed among the F2 progeny at the expected frequency (9 of 47 dark; chi-squared=0.858, P=0.35). Three-quarters of these plants were B'/- (either B/B' or B'/b1-W23), and intensification of the B' phenotype in the dark-anthered individuals confirmed they were Mop1-1/Mop1-1. This result demonstrated that Mop1-1 is not specific to B' but also affects the paramutant Pl' allele.

Figure 4A:
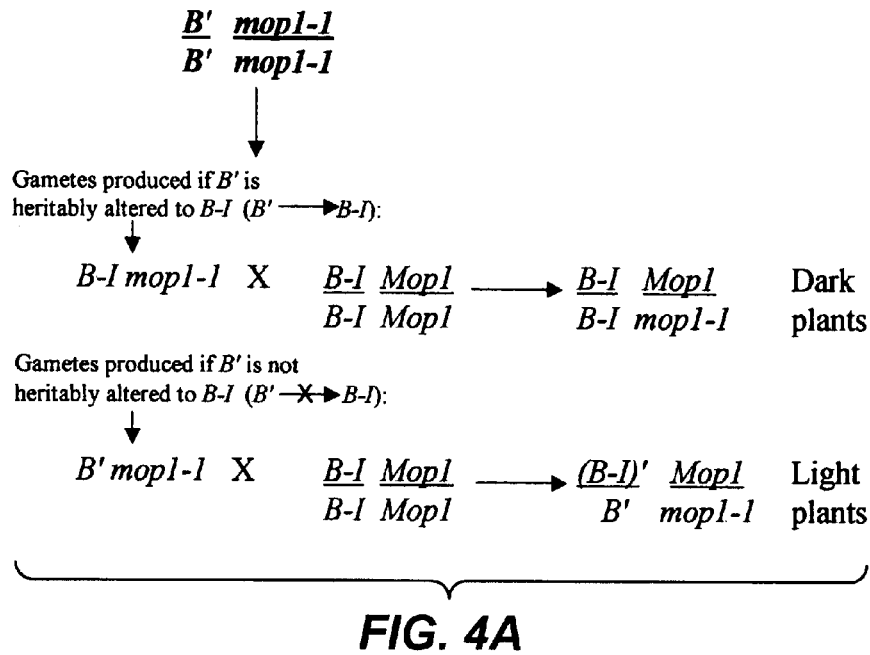
FIGS. 4A and 4B show diagrams outlining tests for heritability of B' and PI' from homozygous Mop1-1 individuals.(A) If Mop1-1 heritably alters B' to B-I, then B' Mop1-1/Mop1-1 individuals would generate B-I Mop1-1 gametes and progeny would be dark plants. Alternatively, if B' is still B', then all gametes would be B' Mop1-1, B' would paramutate B-I [indicated by (B-I)'] in the next generation and all progeny would be light. (B) If Mop1-1heritably alters PI' to Pl-Rh, then PI' Mop1-1/Mop1-1 individuals would generate PI-Rh Mop1-1 gametes and progeny would have dark anthers. Alternatively, if PI' is still PI', then all gametes would be PI' Mop1-1, PI' would paramutate PI-Rh [indicated by (Pl-Rh)'] in the next generation and all progeny would have light anthers.

Mop1-1 Does Not Heritably Alter B', but Can Heritably Alter Pl'. Under some conditions, paramutant alleles can return to the higher expression state characteristic of the paramutable allele. This has been observed for paramutant alleles of pl1 and r1, though not for b1 (reviewed in Chandler et al., 2000). Genetic crosses were performed to test whether Mop1-1 heritably alters B' to B-I or Pl' to Pl-Rh as diagrammed in FIG. 4. When B' Mop1-1 individuals are crossed with plants null for b1 and wild-type for Mop1 (Mop1), all progeny are light (B'/b Mop1/Mop1-1; >400 plants from >20 families) demonstrating the light pigment phenotype of B' is not heritably altered by Mop1-1. Furthermore, crosses between B' Mop1-1 and B-I Mop1 individuals, both of which are dark, also generate all light progeny [B'/(B-I)', Mop1/Mop1-1; >100 plants from 6 families] indicating the B' allele transmitted from homozygous Mop1-1 plants is fully capable of causing paramutation (FIG. 4A) in a Mop1/Mop1-1 nucleus. Thus, Mop1-1 does not disrupt the inheritance of the B' state.

Figure 4B:
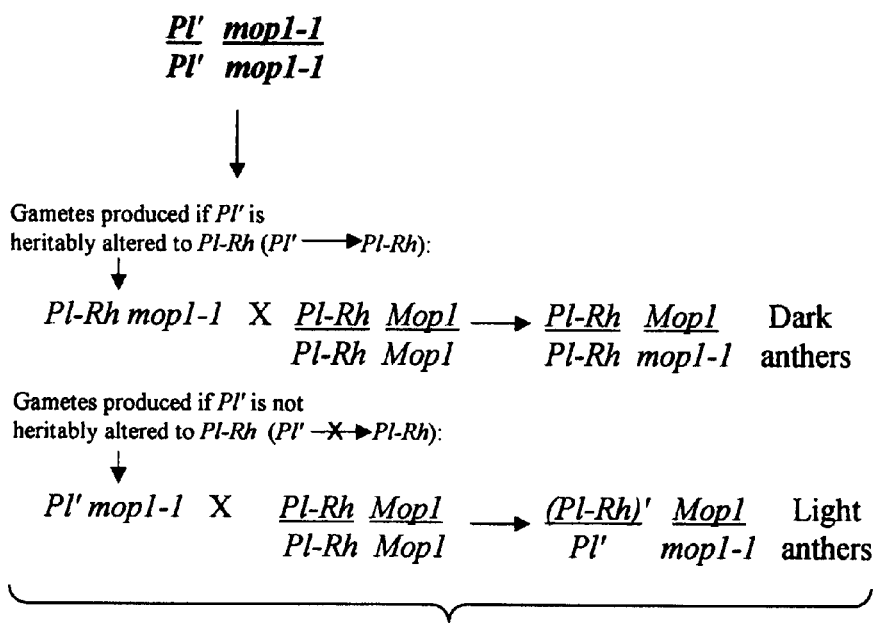
Figure 5:
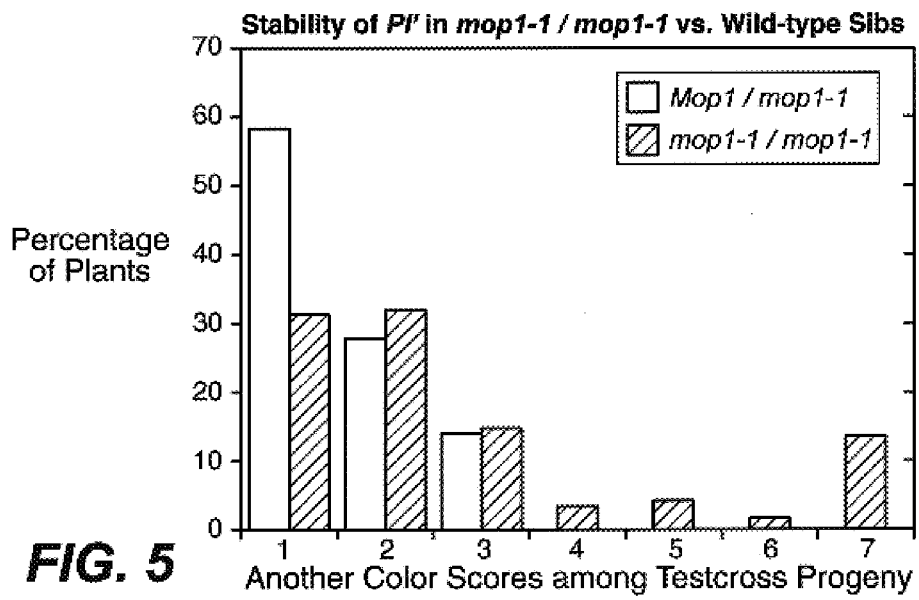
FIG. 5 shows anther color scores (ACSs) of PI' Mop1-1/Mop1-1 outcrosses vs. PI' Mop1/Mop1-1 outcrosses. PI' Mop1-1/Mop1-1 individuals versus PI' Mop1/Mop1-1 individuals were outcrossed to PI-Rh (Mop1/Mop1) testers. Individual progeny plants were scored for amount of anther pigment.

To test whether the Pl' allele in homozygous Pl' Mop1-1 plants can be heritably altered to Pl-Rh, dark-anthered Pl' Mop1-1/Mop1-1 individuals were crossed with Pl-Rh Mop1/Mop1 testers (FIG. 4B). Progeny of this cross were scored with respect to anther pigmentation, using the anther color scale previously described (Hollick et al., 1995). In this scale, individuals with an Anther Color Score (ACS) of 7 are Pl-Rh. Most progeny (~75%) had lightly pigmented anthers, indicating Pl' could be transmitted from homozygous Mop1-1 plants. However, dark-anthered individuals (Pl-Rh-like, ACS 7) were sometimes observed as shown in FIG. 5. This is in contrast to control crosses in which sibling Pl' Mop1/Mop1-1 plants were crossed to Pl-Rh testers and all progeny had lightly pigmented anthers (FIG. 5). Not all Pl' Mop1-1/Mop1-1 individuals produced dark-anthered progeny. In a total of 12 progeny families, representing testcrosses from 11 different individuals, only six families had some dark-anthered progeny. All six of these families were from homozygous Pl'/Pl' Mop1/Mop1-1 individuals in which one of the Pl' alleles was exposed to homozygous Mop1-1 for two consecutive generations. In contrast, no ACS 7 progeny were observed from any of the four Pl' Mop1-1/Mop1-1 individuals in which the Pl' alleles were exposed to homozygous Mop1-1 for a single generation. Thus, Mop1-1 can, but does not always, heritably alter Pl' to Pl-Rh.

Figure 6A:
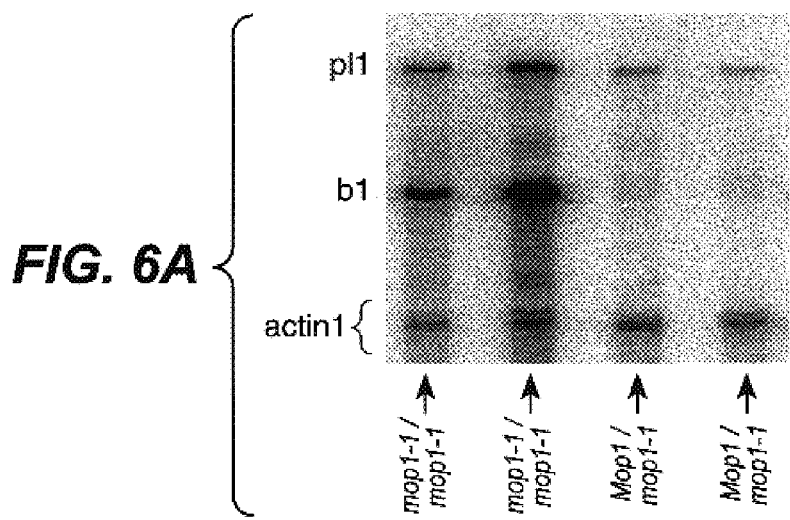
FIGS. 6A–B shows the amounts of transcripts in Mop1-1 versus Wild-Type Siblings. (A) An example of RNase protections for b1,pI1 and actin on four sibling individuals is shown. All individuals are homozygous B' and P1', and segregating for Mop1-1 as indicated. (B) The bar graph shows the normalized amounts of b1 (open bars) and pI1 (closed bars) RNA levels from the RNase protection.
Figure 6B:
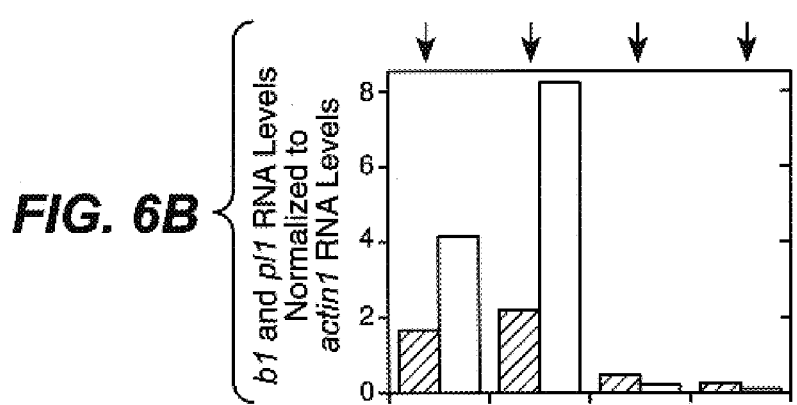

Mop1-1 Increases Transcription of B' and Amounts of Pl' Transcripts. To test whether changes in pigment are the result of changes in transcript levels and transcription, as observed with b1 and pl1 paramutation (Patterson et al., 1993; Hollick et al., 2000), RNA levels and transcription rate were determined. As depicted in FIG. 6, analysis of RNA levels in husk tissue using RNase protection assays reveal a dramatic (46 fold) increase in b1 RNA in B' Mop1-1/Mop1-1 relative to B' Mop1/Mop1-1 siblings. RNase protections also reveal a significant (5.6 fold) increase in pl1 RNA levels in Pl' Mop1-1/Mop1-1 relative to Pl' Mop1/Mop1-1 siblings (FIG. 6). These increases in b1 transcript levels are consistent with (though higher than) the 10–20 fold differences in transcript levels between B-I and B' (Patterson et al., 1993). Increases in pl1 transcript levels are also similar to (though less than) those differences seen between Pl' and Pl-Rh (Hollick et al., 2000).

Figure 7A:
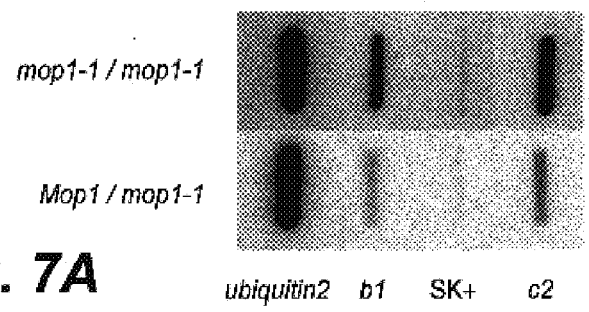
FIGS. 7A–7C show transcription rates in Mop1-1/Mop1-1 versus Mop1-11Mop1-1 siblings. (A) An example of an in vitro transcription assay showing the SK+ plasmid negative control and signal for b1, c2, and ubiquitin2 transcription in B' Mop1-1/Mop1-1 versus B' Mop1/Mop1-1 individuals. (B) Pair-wise data for b1 transcription rate from several in vitro transcription assays for several Mop1-1/Mop1-1 (closed bars) versus Mop1/Mop1-1 (open bars) individuals. The data represent three separate comparisons between pairs of sibling individuals. The n-fold (designated x) increase is given below for each pairwise comparison. (C) Pair-wise data from RNase protection assays for b1 RNA levels normalized to ubiquitin2 RNA levels for the same Mop1-1/Mop1-1 (closed bars) versus Mop1/Mop1-1 (open bars) sibling individuals as examined in (B).
Figure 7B:
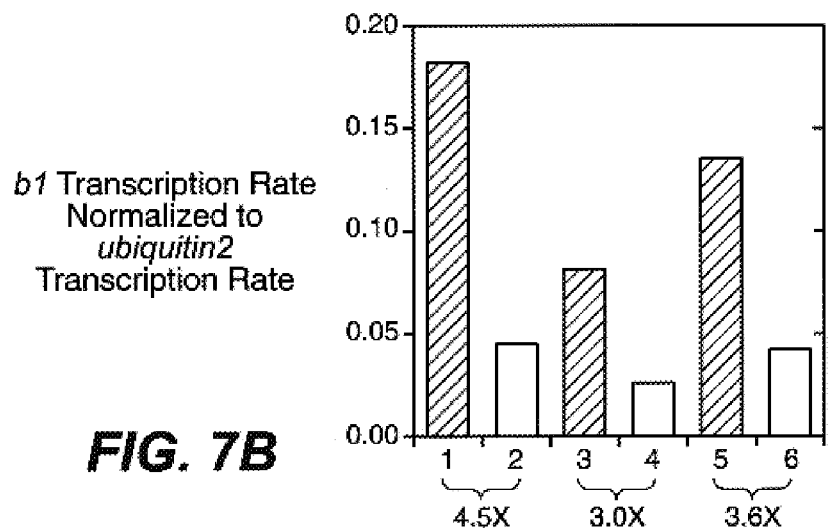
Figure 7C:
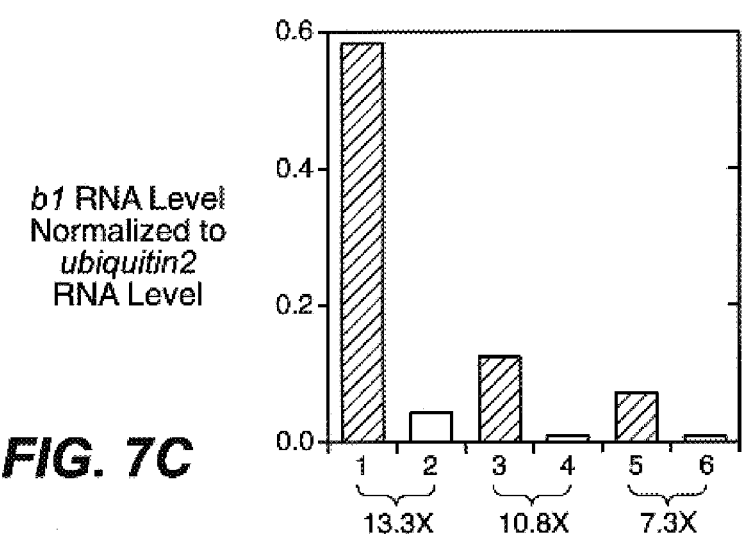

To determine if the increased transcript levels of homozygous B' Mop1-1 plants are associated with increased transcription, in vitro transcription assays were performed on nuclei isolated from sheath tissue. As shown in FIG. 7, these assays reveal that the transcription rate of b1 is increased in sheaths of B' Mop1-1/Mop1-1 plants relative to Mop1/Mop1-1 siblings. The results of three independent pairwise comparisons between sibling Mop1-1/Mop1-1 and Mop1/Mop1-1 individuals are shown graphically in FIG. 7B.

RNase protection assays were done using the same samples to determine the transcript levels in the same sheath tissues. The results of pairwise comparisons of RNA levels in the same six individuals are summarized in FIG. 7C. The in vitro transcription assays reveal a 3–4.5 fold increase in transcription rate whereas RNase protection assays reveal a 7–13 fold increase in transcript levels in the same tissues. Similar differences in fold increase (5–8 versus 13–14) of RNA levels versus transcription rate are observed at c2, a gene regulated by b1 and pI1 (FIG. 7A and data not shown). Overall, the dramatic pigmentation differences between B' Mop1-1/Mop1-1 and B' Mop1-1/Mop1-1 siblings can be explained by increased b1 transcript levels, which can be at least partially explained by an increase in b1 transcription rate.

Figure 8:
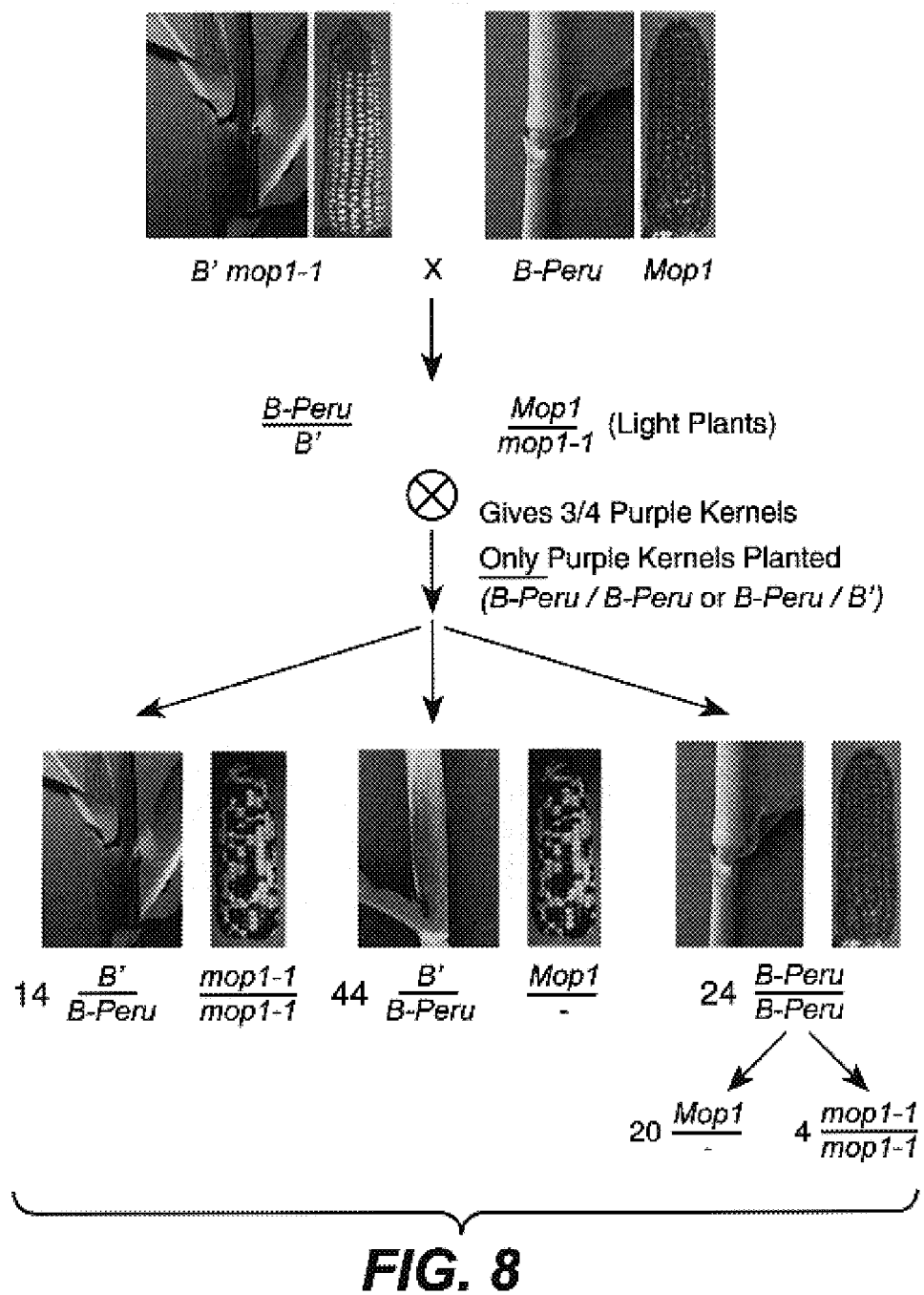
FIG. 8 shows a diagram showing three progeny classes from B'/B-Peru Mop1/Mop1-1 self-pollinations. B' Mop1-1 plants were crossed with B-Peru Mop1 plants. The light F1 B'/B-Peru Mop1/Mop1-1 plants were self-pollinated, and purple kernels (B-Peru/−) were planted. The progeny fell into three phenotypic classes; the numbers and genotypes of each phenotype are shown. The Mop1 genotype of the 24 B-Peru/B-Peru plants was determined by a testcross with B' Mop1-1.

Mop1 Does Not Affect Neutral Alleles. To determine whether Mop1-1 is a general modifier of the anthocyanin regulators, or is specific to those alleles that participate in paramutation, we tested the ability of Mop1-1 to enhance the pigment levels of b1 and pI1 alleles that do not participate in paramutation. The B-Peru allele has dark aleurone pigment, has extremely weak plant pigment that is readily distinguishable from B, and does not participate in paramutation (Patterson et al., 1995). As diagrammed in FIG. 8, B'PIR-g Mop1-1 plants were crossed with a B-Peru PIR-g Mop1 stock, and four F1 individuals were self-pollinated. Only purple F2 kernels were planted to select for homozygous or heterozygous B-Peru. Among these progeny, three classes of plant color phenotypes were observed (FIG. 8). As intensification of B' plant pigmentation would preclude any conclusions about Mop1-1 intensification of the lighter B-Peru plant pigmentation, it was essential to compare only homozygous B-Peru individuals, identified by the presence of 100% purple kernels on the ears produced by these individuals. All 24 individuals characterized as having typical B-Peru plant pigment had ears with 100% purple kernels, confirming their b1 genotype as B-Peru/B-Peru. These plants were testcrossed with B'/B' Mop1-1/Mop1-1 plants to determine their Mop1 genotype. If any of these individuals were also homozygous for Mop1-1, they would be expected to produce 100% dark progeny (plant phenotype) from the testcrosses with B' Mop1-1. Four of the homozygous B-Peru individuals met this expectation, and thus had been homozygous for Mop1-1. The fact that their pigment phenotypes were indistinguishable from their B-Peru/B-Peru Mop1/Mop1-1 or B-Peru/B-Peru Mop1/Mop1 siblings demonstrates that Mop1-1 does not intensify B-Peru pigmentation. All plants that had the B' Mop1-1 or B' Mop1/– phenotype (FIG. 8) were confirmed to be heterozygous for B'.

In the process of introducing Mop1-1 into other genetic backgrounds, a stock was generated that contained B-bar and pI-W22, weakly pigmented neutral alleles of b1 and pI1, respectively. Three dark plants, subsequently shown to be B-bar/B' Mop1-1/Mop1-1 pI-W22/pI-W22, were self-pollinated, producing ¾ dark and ¼ light progeny (76 dark vs. 25 light). PCR analyses confirmed that the light progeny were homozygous for B-bar and the darks all contained at least one B' allele. The fact that these light progeny resembled B-bar Mop1/– pI-W22 plants demonstrated that Mop1-1 did not intensify B-bar. As these plants were also homozygous for pI-W22, an allele of pI1 which does not participate in paramutation (Hollick et al., 1995), Mop1-1 effects on a neutral pI1 allele could also be examined. All plants had weak pI-W22 anther color. Together with the results described above with B-Peru, these results suggest that the Mop1-1 intensification of pigment is selective for paramutant alleles.

Mop1-1 Inhibits the Establishment of b1 Paramutation. To determine whether Mop1 is involved in the establishment of b1 paramutation, we asked whether B-I could be paramutated when it encounters B' in a homozygous Mop1-1 nucleus. To address this question, homozygous B' Mop1-1 individuals were crossed, as diagrammed in FIG. 9, with plants heterozygous for B-I/b1-K55 and Mop1/Mop1-1. The b1-K55 allele is recessive, producing a green plant when homozygous. B'/B-I and B'/b1-K55 were differentiated by restriction fragment length polymorphisms between the B-1 and b1-K55 alleles, and each class was crossed with both B-I/B-Peru testers (FIG. 9) and with b1 testers (not diagrammed). A feature of the B-I/B-Peru cross is that the B-I allele is frequently more stable (less prone to spontaneous paramutation to B') when heterozygous with a neutral allele. Furthermore, the purple aleurone pigmentation of B-Peru kernels provides a useful marker for the allele, and the weak B-Peru plant pigmentation is recessive to and readily distinguished from B-1 or B' pigmentation (Radicella et al., 1992; Patterson et al., 1995).

Among offspring of B'/B-I Mop1-1/Mop1-1 plants crossed to B-I/B-Peru (Mop1/Mop1), purple kernels (inheriting the B-Peru allele of the tester) gave rise to plants segregating 50% light (original B') and 50% dark (unaltered B-1) individuals, as shown in Table 2. A similar result was obtained among offspring of B'/B-I Mop1-1/Mop1-1 plants crossed with b1 tester stocks (b1-K55/b1-K55 Mop1/Mop1 or b1-K55/b1-W23 Mop1/Mop1). Eighteen of 43 plants were dark or medium-dark and the remaining 25 individuals were light (Table 2). Medium-dark individuals could be explained by spontaneous paramutation of B-1 to B', or PI-Rh to PI', which is often observed for these alleles (Coe, 1966; Hollick et al., 1995). Some of these individuals were crossed with appropriate tester stocks, and the phenotypes of progeny were consistent with spontaneous paramutation of PI-Rh causing the reduction in pigment. Control crosses of B'/B-1 Mop1/Mop1-1 plants to the same B-I/B-Peru and b1 tester stocks produced all light progeny. These results demonstrate that paramutation is not established in Mop1-1/Mop1-1 plants.

Surprisingly, colorless kernels from the same crosses to the B-I/B-Peru tester (inheriting the B-I allele of the tester) gave fewer than the expected 50% B-1 plants (Table 2). Many individuals were dark toward the base of the plant, but appeared to lighten progressively during development such that at anthesis, 46 plants were scored as medium or light and only three as dark (B-I). Possible reasons for the decreased frequency of B-I offspring in this experiment include spontaneous paramutation of the B-I allele from the tester, or subtle destabilization of the B-I allele transmitted from the B'/B-I Mop1-1/Mop1-1 plants. These hypotheses are considered more thoroughly in the discussion. Nevertheless, Mop1-1 is clearly able to inhibit the establishment of paramutation in B'/B-I Mop1-1/Mop1-1 plants, as dark offspring carrying B-I segregate from these individuals. This is in sharp contrast to stocks wildtype for Mop1 in which paramutation always occurs (Coe, 1966; Patterson et al., 1993; Patterson et al., 1995).

TABLE 2

Results of B'/B-I mop1-1/mop1-1 Test Crosses with several Tester Stocks

| Cross | | No. of Dark Progeny | No. of Light Progeny | $\chi^2$ (P)[a] |
|---|---|---|---|---|
| B'/B-I mop1-1/mop1-1 b/b Mop1/Mop1 | x | 18[b] | 25 | 1.139 (0.29) |
| B'/B-I mop1-1/mop1-1 B-Peru Mop 1[c] | x | 26 | 25 | 0.0196 (0.89) |

TABLE 2-continued

Results of B'/B-I mop1-1/mop1-1
Test Crosses with several Tester Stocks

| Cross | | No. of Dark Progeny | No. of Light Progeny | $\chi^2$ (P)[a] |
|---|---|---|---|---|
| B'/B-I mop1-1/mop1-1 B-I Mop1[c] | x | 3 | 46[b] | 37.7 (<0.0001) |

[a]The hypothesis tested is 1:1 segregation.
[b]Plants were scored as dark or medium-dark. Test crosses demonstrated that medium-darks were B-I Pl'.
[c]B-Peru Mop1 and B-I Mop1 represent the different gametes produced by the B-I/B-Peru tester.
[d]Plants were scored as medium (20) or light (26). Many mediums were darker at the base, consistent with spontaneous paramutation.

Mop1-1 May Inhibit the Establishment of pl1 Paramutation. We also examined whether Mop1-1 inhibits the establishment of pl1 paramutation, though this experiment is complicated by the fact that Pl' can occasionally be heritably altered to Pl-Rh in homozygous Mop1-1 plants. To ensure that the allele entering the cross was the paramutagenic Pl', light-anthered Pl'/Pl' Mop1/Mop1-1 plants (in which Pl' is stable and does not change to Pl-Rh) were crossed with dark-anthered Pl-Rh/Pl-Rh Mop1/Mop1-1 plants. Each of these stocks also carried the B' allele, which enabled an independent assay of the Mop1 genotype. Among the progeny, there was perfect cosegregation of dark plant and anther pigmentation (Mop1-1/Mop1-1). Three dark-anthered individuals (Pl'/Pl-Rh) were crossed with a b1-K55 Pl-Rh tester to determine whether paramutation occurred (all progeny should have light anthers) or whether the Pl-Rh allele could be inherited unaltered (50% dark and 50% light anthered plants). The resulting progeny segregated 39 purple-anthered Pl-Rh plants and 36 light-anthered Pl' plants. The simplest explanation for this result is that Mop1-1/Mop1-1 prevented the establishment of paramutation resulting in the segregation of the original Pl-Rh and Pl' alleles.

Figure 10A:
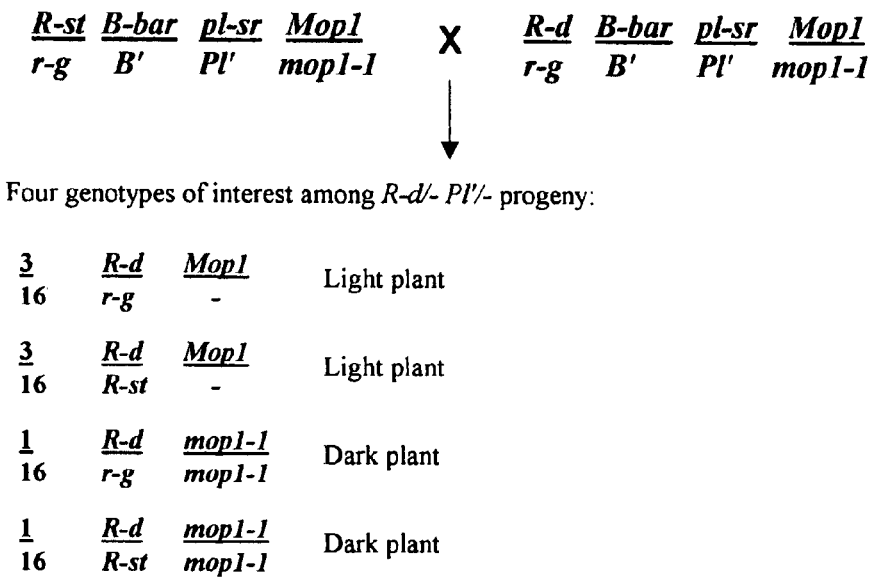
FIGS. 10A–10B show a summary of Mop1-1 effects on r1 paramutation. (A) Parental genotypes and progeny classes used to evaluate the effect of Mop1-1 on the establishment of r1 paramutation. Mop1 genotypes were determined based upon the intensity of plant pigment within the Pl/− phenotypic class. Individuals belonging to the two R-d/− genotypic classes indicated were identified by crossing to an R-g tester stock and the R-d/R-g kernel progeny were then assayed for pigment intensity. (B) The bar graph shows results of paramutation test with r1. Color scores for kernels inheriting the R-d allele are plotted from individuals having the parental genotype indicated along the x-axis. The first two columns are Mop1/− genotype controls. Color score equals 100 minus average reflectometer reading as described (Alleman and Kermicle, 1993). Error bars indicate SD.
Figure 10B:
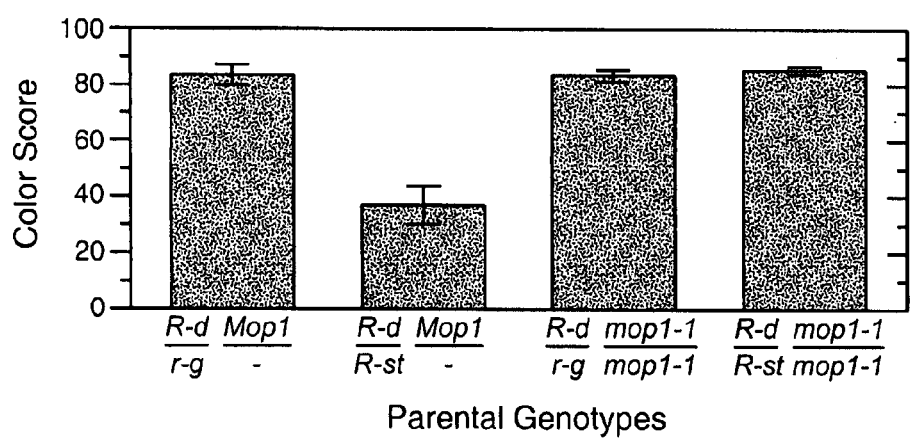

Mop1-1 Inhibits the Establishment of r1 Paramutation. As discussed above, the phenomenology of r1 paramutation is very different from that of b1. We asked whether Mop1-1 is able to affect paramutation at r1. Our B' Mop1-1 stocks contained the R-g allele of r1, which does not participate in paramutation (Kermicle et al., 1995). These Mop1-1 R-g stocks were crossed with stocks wildtype for mop1 (Mop1) and containing r1 haplotypes that participate in paramutation. The term haplotype is used for complexes composed of multiple r1 genes. The r1 haplotypes used included paramutagenic R-stippled (R-st) and two paramutable haplotypes, standard R-r and R-d:Catspaw (R-d). The F1's between R-st and Mop1-1 (R-st/R-g; Mop1/Mop1-1) were intercrossed with F1's of the paramutable haplotypes (R-d/R-g or R-r/R-g; Mop1/Mop1-1). Thus, the paramutagenic and paramutable haplotypes were combined in homozygous Mop1-1 mutant progeny, and in siblings wildtype for Mop1 (Mop1/–). Fifty percent of intercross progeny inherited the paramutable haplotype (R-d or R-r), and among these, four genotypes of interest segregate as shown for R-d in FIG. 10A. The presence of B' allows the Mop1 genotype to be easily monitored. Testcrosses of Mop1/– (either Mop1/Mop1 or Mop1/Mop1-1) individuals in which R-d was heterozygous with neutral R-g provide a baseline for wild-type kernel pigmentation. Testcrosses of R-d/R-g plants homozygous for Mop1-1 did not differ detectably from wildtype (Mop1/–), as shown in FIG. 10B. Paramutation occurred as expected in the R-st/R-d Mop1/– individuals, manifest as reduced pigment in the R-d progeny (FIG. 10B). However, siblings homozygous for Mop1-1 showed no reduction of R-d expression (FIG. 10B). Thus, in individuals homozygous for the Mop1-1 mutation, paramutable R-d exits the cross as if it had been heterozygous with a neutral allele rather than with paramutagenic R-st. Similar results were obtained with the paramutable standard R-r (not shown). This demonstrates that Mop1-1 is able to inhibit the establishment of r1 paramutation.

Mutations in Mop1 Correlate with Pleiotropic Effects. As shown in Table 3 and FIGS. 11B, 11C and 11D, plants homozygous for B' Mop1-1 can show direct or indirect developmental abnormalities. The range of effects seen include delayed flowering or reduced stature relative to wild-type siblings, spindly and sometimes barren stalks, and in some instances, aberrant development resulting in feminized tassels (such as that observed in tasselseed mutants—Irish et al., 1994). We reproducibly see differences in flowering time, whereas other abnormalities appear stochastically. There may be an environmental effect on the frequency with which these developmental abnormalities occur, as the frequency has been highest in our Hawaii nursery during the past two winters. Two alternative hypotheses could explain the correlation of these effects with Mop1-1. The effects could be caused either by other mutations that are linked to Mop1-1, or by the Mop1-1 mutation itself. Recently, a second allele of Mop1 was isolated from a similar screen looking for modification of Pl' instead of B' and using ethyl methanesulfonate (EMS) as the mutagen (Example 3). This independent allele (Mop1-2EMS) provides independent data with which to judge the two alternative hypotheses. B'/– Mop1-2EMS/Mop1-2EMS and B'/– Mop1-1/Mop1-2EMS individuals show the same suite of pleiotropic phenotypes as homozygous Mop1-1 (Table 3). This strongly suggests that these negative pleiotropic effects are the result of the mutant Mop1 locus, rather than the result of linked mutations.

TABLE 3

Developmental Phenotypes[a] Associated with Mop1 Mutants

| | | | | Phenotypes | | | | | |
|---|---|---|---|---|---|---|---|---|---|
| | | Seg | | Mop1 | | Mop1 | | | |
| Family | Exp | Obs | $\chi^2$(P) | N[b] | O | N | STS | WTS | BT | R[c] |
| Mop1-1 segregating | 1:1 | 37:39 | 0.05 (0.82) | 36 | 1[d] | 13 | 15 | 3 | 3 | 5 |
| Mop1-2EMS segregating | 3:1 | 75:15 | 3.33 (0.07) | 74 | 1[e] | 6 | 2 | 1[f] | 4 | 2 |
| Mop1-1/Mop1-2EMS segregating | 1:1 | 13:15 | 0.14 (0.71) | 13 | — | 6 | 3 | 1 | 2 | 3 |

[a]Phenotypes are as follows: Mop1, lightly pigmented plant; Mop1, darkly pigmented plant; N, normal; O, other; STS, strong tasselseed; WTS, weak tasselseed; BT, barrenized tassel; R, runty or scrawny plant.
[b]The number of individuals represent progeny from four, five, and two plants for the Mop1-1, mop 1-2EMS, and Mop1-1/Mop1-2EMS segregating crosses, respectively.
[c]One of five, one of two, and one of three plants also possessed a barrenized tassel, and one of five plants possessed a feminized tassel, which failed to emerge (see FIG. 11C).
[d]This plant was slightly deformed with a twisted stalk.
[e]This plant was diseased.
[f]This plant was shorter than were sibling plants and did not produce an ear.

Mop1-1 Does Not Affect Global Methylation Levels. Although no differences in DNA methylation are observed in comparisons of the paramutagenic and paramutable alleles of b1 and pl1 (within the coding and ~15 kb of the respective flanking regions, Patterson et al., 1993; Hollick et al., 2000), paramutation of R-r correlates with DNA methylation in the transcribed region (Walker, 1998). In other systems, changes in DNA methylation often correlate with differences in transcription, thus one model is that Mop1 encodes a protein that influences global DNA methylation levels such as a DNA methyltransferase (Finnegan et al., 1996) or ddm1 (decrease in DNA methylation, Vongs et al., 1993). Under this model, one could hypothesize that methylation differences occur at b1 and pI1, but these changes occur outside of the regions examined. We tested whether global DNA methylation levels are affected by Mop1-1. DNA blots with methylation sensitive restriction enzymes were prepared to compare homozygous B' Mop1-1 individuals, wild-type siblings (B' Mop1/Mop1-1), and B' stocks (Mop1/Mop1). These blots were hybridized with repeated sequences of the 45S ribosomal region (McMullen et al., 1986) as well as a repeated sequence found at centromeres (Jiang et al., 1996). As shown in FIGS. 12A–12B, no differences in DNA methylation were detected among the Mop1 genotypes.

Mop1 and Paramutuation. Our results demonstrate that Mop1 plays a central role in paramutation; the Mop1-1 mutation disrupts the maintenance and establishment of paramutation at multiple maize loci, but has no effect on alleles that do not participate in paramutation. The pleiotropic developmental phenotypes that stochastically occur in some families segregating Mop1 mutations suggest that Mop1 may have additional regulatory functions beyond paramutation.

Paramutation at b1, p1 and r1 Shares a Common Mechanism. There are unique aspects to the behavior of b1, pI1 and r1 alleles participating in paramutation (reviewed in Chandler et al., 2000). r1 paramutation involves structurally distinct haplotypes of a complex or repeated nature. In contrast, B' and PI' are spontaneous derivatives of B-I and PI-Rh, respectively. Furthermore, increased methylation is readily apparent in R-r' relative to R-r (Walker, 1998), whereas such differences have not been observed for b1 and pI1 (Patterson et al., 1993). We have demonstrated that Mop1-1 disrupts the maintenance of B' and PI' expression, the heritability of PI', and the establishment of b1 and r1 paramutation. These results provide compelling evidence that, despite several phenomenological differences, all three loci use a common molecular factor for paramutation, strongly suggesting that a common mechanism underlies paramutation at these three loci.

A Role for MOP1 in the Establishment and Maintenance of the Paramutant State. Our results indicate MOP1 function is clearly involved in all three phases of gene silencing; establishment, maintenance, and heritability (reviewed in Loo and Rine, 1995). When paramutable and paramutagenic alleles of b1, pI1 or r1 are heterozygous, paramutation always occurs (reviewed in Kermicle, 1996; Chandler et al., 2000), yet in nuclei homozygous for Mop1-1, paramutation was not established at b1, r1 or pI1. When PI-Rh was introduced to PI' in homozygous Mop1-1 plants, PI-Rh appeared to be transmitted unaltered as 50% dark-anthered (PI-Rh) and 50% light-anthered (PI) plants segregated. This interpretation is complicated by the fact that homozygous PI' Mop1-1 plants can sometimes produce dark-anthered PI-Rh progeny. However, it seems unlikely that the 50% dark-anthered plants resulted from full establishment of paramutation and subsequent reversion of half the PI' alleles to PI-Rh. The establishment experiment used PI' alleles exposed to homozygous Mop1-1 for a single generation, a condition in which no PI-Rh progeny were observed in other experiments. Thus, the simplest explanation for the 50% segregation observed in this experiment is that Mop1-1 inhibits the establishment of pI1 paramutation.

One possibility is that MOP1 mediates or facilitates the interaction between the paramutagenic and paramutable alleles, such that loss of function disrupts that interaction. MOP1 may be necessary for the paramutagenic properties of B', PI' or R-st, such that loss of function makes these alleles more similar to neutral or paramutable alleles. Perhaps consistent with this, the B' allele is modified by Mop1-1 such that, in homozygous Mop1-1, B' resembles B-I with respect to phenotype, transcription, and the inability to paramutate another B-I allele. The appearance of phenotypically B' sectors in B' Mop1-1 plants further suggests that MOP1 can function throughout development to reduce the expression of B' such that regaining MOP1 function in a somatic sector re-establishes the reduced expression state.

The effect of Mop1-1 on B' provides a very clear demarcation between two of the phases of gene silencing, maintenance and inheritance, as described by Loo and Rine (1995). Though functional MOP1 is required to maintain the reduced transcription state of B', loss of MOP1 function is not sufficient to disrupt the inheritance of the B' state as it is faithfully and completely restored upon recovering MOP1 function. In fact, we know of no condition in which B' is heritably changed to B-I. We have speculated this is because B' represents the default transcription state specified by the DNA sequence (Patterson et al., 1993).

Allele Interactions May Influence the Stability of Epigenetic States. Allelic interactions may account for our observation that B-I segregates at different frequencies from B-I/B' Mop1-1/Mop1-1 plants depending on what it is crossed with. In crosses to the neutral alleles B-Peru and b1 (b1-K55 or b1-W23), B'/B-I Mop1-1/Mop1-1 plants transmitted 50% dark individuals, completely consistent with the failure to establish paramutation in the B'/B-I Mop1-1/Mop1-1 plants. Interestingly, fewer than the expected 50% B-I individuals were observed segregating from B'/B-I Mop1-1/Mop1-1 plants in crosses to B-I. Observation of B-I progeny at the anticipated 50% frequency would require three conditions: inheritance of an unaltered B-I allele from the B-I/B-Peru tester parent, inheritance of an unaltered B-I allele from B'/B-I Mop1-1/Mop1-1 individuals, and stability of both B-I alleles in the homozygous B-I progeny individuals. Homozygous B-I is generally less stable than B-I/B-Peru. The developmentally progressive reduction in pigment of many (presumed B-I/B-I) progeny plants appeared similar to, and thus could be explained by, the progression sometimes observed during spontaneous paramutation of B-I to B'. This result could also be caused by a higher than usual rate of spontaneous paramutation of the B-I allele segregating from the B-I/B-Peru tester. Alternatively, the B-I allele segregating from B'/B-I Mop1-1/Mop1-1 may be subtly destabilized. This subtle destabilization could be exacerbated in the next generation by homozygosity with a second B-I allele, whereas it could be overcome in the next generation by heterozygosity with a neutral allele such as B-Peru or b1.

A Model for MOP1 Function and Paramutation. Numerous facets of b1, r1 and pI1 paramutation are consistent with chromatin structural changes, rather than DNA sequence changes, underlying paramutation. The absence of detectable DNA sequence differences between B' and B-I, the multiple levels of PI' expression, and the instability of the paramutant R-r' and PI' states fit well with a chromatin model. We propose that MOP1 functions as a chromatin remodeling protein. As observed for some chromatin related proteins, individuals mutant for Mop1 can show developmental phenotypes (Grossniklaus et al., 1998; Eshed et al., 1999; Kakutani et al., 1999; Ogas et al., 1999). We hypothesize that MOP1 is involved in the assembly of a repressive chromatin structure at b1, pl1 and r1 upon paramutation. This repressive structure could be analogous to Polycomb group (PcG) complexes assembled at Polycomb Response Elements (PRE, Pirrotta, 1998; Hollick et al., 1997).

The distinct expression states of B-I vs. B' and Pl-Rh vs. Pl', as well as the spontaneous and directed alteration of the paramutable alleles, could be explained by this model. The alleles that participate in paramutation are hypothesized to possess PRE-like elements. In the high expression state (B-I or Pl-Rh), the elements are not efficiently recognized for PcG-like assembly. We postulate that the chromatin structure can spontaneously change allowing access of PcG-like proteins for assembly, resulting in the B' and Pl' states. The fully assembled state of the B' and Pl' alleles, when together in a nucleus with the unassembled state, would induce assembly on the paramutable allele (Patterson et al., 1993; Hollick et al., 1997).

Variations on this model can explain differences in stability between the Pl' vs. the B' states, and the different effect Mop1-1 has on the heritability of this state. Once assembled in B', the PcG-like complex would remain quite stable due to multiple, strong interactions between members of the complex and DNA binding sites. When MOP1 function is lacking in B' Mop1-1 homozygotes, several remaining members of the complex stay associated with the PRE-like binding sites, such that restoration of MOP1 function quickly re-establishes the repressive structure, just as some residual proteins are thought to mark PREs for rapid reassembly in Drosophila (Pirrotta, 1998). Divergence or fewer binding sites at pl1 could result in a less stable complex relative to b1. Loss of MOP1 function in Pl' Mop1-1 homozygotes, combined with reduced or compromised binding sites, could destabilize the complex such that residual association of the complex with the PRE-like element is reduced in some nuclei resulting in the Pl-Rh state.

Mutants Affecting Epigenetic Silencing or Allelic Interactions. Active research into many trans-sensing phenomena involves identifying mutations that disrupt the interaction. As paramutation and other trans-sensing interactions share many features, these screens could identify Mop1 homologues. Our results suggest that Mop1 is unlikely to represent a DNA methyltransferase or ddm1-orthologue, because the Mop1-1 mutation does not alter methylation levels of repetitive centromeric sequences or the 45S ribosomal repeated sequences. The ddm1 locus was identified based upon its effect on methylation levels of repetitive sequences in Arabidopsis, such as the ribosomal genes and centromeric repeats (Vongs et al., 1993). The ddm1 locus has been cloned and it shares similarity with SNF2, a yeast protein involved in chromatin remodeling (Jeddeloh et al., 1999). Interestingly, a related protein in humans has also been shown to decrease global DNA methylation when mutated (Gibbons et al., 2000). Similarly, decreased activity of the DNA methyltransferase of Arabidopsis achieved by antisense expression of a MET1 transgene reduces the methylation levels of repeated sequences (Finnegan et al., 1996).

Several mutations altering the transcriptional silencing of plant transgenes have been identified (Furner et al., 1998; Mittelsten Scheid et al., 1998; Amedeo et al., 2000). Some of these mutations turn out to be allelic to ddm1 (Mittelsten Scheid et al., 1998; Jeddeloh et al., 1999), whereas one encodes a novel protein (Amedeo et al., 2000). Several mutations have been identified that disrupt cosuppression or post-transcriptional gene silencing (Elmayan et al., 1998), In is not yet clear whether transcriptional and post-transcriptional gene silencing are mechanistically related (reviewed in Meyer and Saedler, 1996). A screen for mutations affecting transvection at the yellow locus of Drosophila identified exclusively cis-acting mutations at yellow (Morris et al., 1999). Numerous mutations in Drosophila have been isolated that affect position-effect variegation, identifying proteins associated with and involved in chromatin structure (Sass and Henikoff, 1998; Wakimoto, 1998; Wallrath, 1998; Cryderman et al., 1999).

Example 2

Mutations that Affect Paramutation in Maize Also Reverse Mu Transposon Methylation Introduction. Very little is known about the mechanism of paramutation. At r1, there is a correlation between the methylation state of some parts of the gene and its expression state (Walker 1998). Also at r1, there is a relationship between the degree of paramutagenicity of an allele and the number of repeats of the coding region and flanking DNA (Kermicle et al. 1995). As a transposon (doppia) is present in the regulatory region of several paramutable alleles of r1, it has been suggested that this transposable element is causally related to paramutation. However, this relationship remains correlative, and there are paramutagenic alleles of r1, such as R-marbled, that do not carry this transposon (Panavas et al. 1999). Further, despite the fact that the promoter region of the paramutable B-I allele is littered with transposable elements, no correlation between methylation of these elements and transcription level has been observed at b1 (Patterson et al. 1993), or pl1 (Hollick et al. 2000). Thus, there is no consistent correlation to date between paramutation and transposable element methylation within or nearby a gene.

Recently, a mutation, Mop1-1, has been isolated which prevents paramutation at b1, r1, and pl1 (Dorweiler et al. 2000). When this mutation is homozygous, the normally low expressing allele of b1, B', expresses at the level of the high expressing allele, B-I. This results in the dark purple plant color characteristic of the B-I allele as opposed to the lighter and sporadic purple color characteristic of the B' allele. Further, when B' is heterozygous with B-I in a Mop1-1 homozygous background paramutation is prevented, with both the B' and B-I phenotypes transmitted upon out crossing. In the absence of the Mop1-1 mutation only the B' phenotype is transmitted.

Although in Mop1-1 homozygotes B' expresses at the level of B-I and it cannot paramutate B-I, it is not heritably altered to B-I, because when out crossed to generate a heterozygote (Mop1/Mop1-1) B' is observed. These results suggest that the Mop1 gene product is involved with the process of paramutation, but it does not alter the heritable state of B'. The Mop1-1 mutation also prevents the establishment of paramutation at the pl1 and r1 loci, indicating that the Mop1 gene product is a general regulator of paramutation (Dorweiler et al. 2000).

Herein we show that mutations in Mop1 can prevent and reverse Mu element methylation. Despite this reversal of methylation, we do not see reactivation of Mu element transposition in these genetic backgrounds, suggesting that the Mu inactive state is not reversible by Mop1 mutations. Because the Mop1 mutation affects multiple loci, each of which has very different promoter sequences, we hypothesize that this mutation is operating on chromatin configuration, rather than specific sequences.

Materials and Methods:

Genetic Crosses. In the crosses that follow, a single allele listing indicates homozygosity, whereas heterozygous individuals are indicated with alleles separated by a slash (/). Following maize genetic nomenclature, recessive alleles are indicated by lower case and dominant alleles are indicated by capitalization of the first letter. Unless indicated otherwise all stocks carry functional alleles of all the anthocyanin biosynthetic genes. The alleles of the regulatory genes r1, b1, and pl1 that are in each stock are indicated for each cross.

Generation of a Mop1-1 Homozygote. The Mop1-1 homozygous plant used in crosses with MuKiller was generated as follows: B' PIR-g (recessive allele of r1 with no pigment and no paramutation activity) Mop1-1 plants were crossed to B' PIR-g Mop1, and the resulting F1 plants were back crossed to B' PIR-g Mop1-1 plants. Homozygous Mop1-1 mutants are darkly pigmented in leaf sheaths, husks and tassel branches and glumes, while the Mop1/Mop1-1 heterozygotes are lightly pigmented in the same tissues (Dorweiler et al. 2000). As this stock was derived from an active Mutator stock, it carried multiple MuDR elements and hypomethylated MuDR and Mu1 elements as evidenced by DNA blotting (not shown).

Generation of a plant carrying MuKiller. To detect MuDR activity we used a1-mum2. This mutation contains a Mu1 insertion in the 5' promoter region of the a1 anthocyanin biosynthesis gene (O'Reilly et al. 1985). In the presence of active MuDR elements excisions of Mu1 can be scored as somatic purple sectors in the kernels. MuKiller, a dominant factor present in some lines but not in our minimal Mutator line, is competent to silence a single MuDR element (Lisch and Freeling 1994). A plant carrying a single MuDR element on chromosome 2 L (Chomet et al. 1991) with the genotype B' pl-sr (allele of pl1 that confers sun-red anthers and husks) R-g (r1 allele that confers purple seed) a1-mum2 MuDR/– was crossed to a line carrying MuKiller (MuK) and no active MuDR elements (B' pl-sr R-g a1-mum2 MuK/+). The resulting plants were scored for the presence of newly silenced MuDR elements as indicated by the reduced excision frequency of the Mu1 element from a1-mum2 and methylation of Mu1 elements in the presence of MuDR. Of nine individuals examined in this family, three carried at least one full-length MuDR element and several methylated Mu1 elements, consistent with the epigenetic silencing of MuDR elements by the MuK activity segregating in this family. The first ear of one such plant was used in the cross with a Mop1-1/Mop1-1 homozygote as described below. The second ear was crossed to a plant lacking MuDR elements and homozygous for the a1-mum2 reporter (Chomet et al. 1991). None of the kernels resulting from this test cross showed evidence of excisions of Mu1 from a1-mum2, confirming the silencing of MuDR in this family.

Crossing Mop1-1 to MuKiller. A single B' PIR-g A1 Mop1-1 plant was crossed to a plant carrying a silenced MuDR element (as described above). The resulting progeny were self-fertilized, yielding Mop1-1 homozygotes, Mop1-1/Mop1 heterozygotes and Mop1 homozygotes. To generate a second generation of Mop1-1 homozygous plants, B' Mop1-1 homozygous plants resulting from the above cross were identified by their dark plant pigment and were crossed to Mop1-1/Mop1 siblings and the resulting plants were scored for the Mop1-1 phenotype. To test for reversals of Mu element methylation, Mop1/Mop1-1 progeny from that cross, which carried methylated Mu elements, were self fertilized to generate Mop1-1 homozygous mutants that had been heterozygous and methylated in the previous generation.

Isolation of Mop1-1 stocks lacking MuDR. Plants carrying Mop1-1 in the absence of full length MuDR were isolated from the same genetic background as those carrying full length MuDR elements by screening for the loss of MuDR using DNA blots. The absence of MuDR was determined by digestion with SacI, XbaI, and EcoRI+HindIII. Diagnostic fragments for full length MuDR elements were absent in these lines.

Isolation of Stocks Carrying Silenced MuDR Elements. Plants carrying MuDR at the original position from which it was first cloned (Chomet et al. 1991) were crossed to plants carrying MuKiller. Progeny that carried both MuDR and methylation of HinfI sites in Mu1 elements, consistent with the activity of MuKiller, were self-fertilized to generate stocks that were homozygous for silenced MuDR. The progeny kernels, all of which lacked excisions of Mu1 from the reporter a1-mum2 allele, were screened by DNA gel blot for the presence of homozygous MuDR elements. These plants were again self-fertilized to generate stocks carrying homozygous silenced MuDR elements.

Generation of seeds carrying a single silenced MuDR element that were also homozygous for Mop1-2EMS. Plants carrying homozygous silenced MuDR elements (a1-mum2; MuDR, R-g) were crossed to plants that were A1, R-g, Mop1-2EMS (an EMS-induced allele of Mop1) and that lacked full-length MuDR elements. The progeny plants were self-fertilized, and the resulting families were screened for the presence of spotted kernels. If Mop1-2EMS reactivated silenced MuDR elements, then only the resulting kernels that were homozygous for a1-mum2 (¼), carried R-g/R-g or R-g/R-g (and not r1 mottled) (½), homozygous for Mop1-2EMS (¼) and carrying MuDR* (¾) would be expected to be spotted. Thus, the expected frequency of spotted kernels was 2.34% (¼×½×¼×¾). In addition to self-fertilization, some plants were crossed to plants that were homozygous for Mop1-1, a1-mum2, and R-g. The expected frequency of spotted kernels in the families generated from these crosses was 6.5% (½ a1-mum2/a1-mum2×½ R-g/R-g or R-g/R-g× ½ MuDR×½ Mop1/Mop1).

DNA preparation and genomic blotting. DNA preparation and genomic blotting were performed as previously described (Dorweiler et al. 2000). A plasmid of Mu1 was as previously described (Talbert et al. 1989). To generate an internal probe for Mu1, the plasmid was digested with AvaI and BstEII, and the internal fragment was gel isolated. An internal fragment of MuDR bounded by EcoRI and BamHI was as described (Chomet et al. 1991). The b1 upstream probe used to generate the data shown in FIGS. 14 and 16 was previously described in (Patterson et al. 1993) and (Patterson et al. 1995). As a control for partial digestion of DNA, blots were reprobed with a KpnI fragment of the a1 gene spanning a region of the coding sequence adjacent to (but not including) the Mu1 insertion in this gene (O'Reilly et al. 1985). As a control for the blot with the SacI digest in FIG. 13, the blot was probed with a single copy PstI fragment flanking but not including the MuDR insertion on chromosome 2 L (not shown) (Lisch et al. 1995). That same probe was used to identify individuals containing that specific MuDR insertion in MuDR reactivation experiments.

Results

The Mop1-1 mutation prevents the dominant methylation of Mu elements. The Mop1-1 mutation was originally isolated in a Mutator active line (Dorweiler et al. 2000) with multiple copies of both MuDR and Mu1, all of which were hypomethylated (data not shown). To examine the interaction between the Mop1-1 mutation and methylation of the Mutator system, it was necessary to inactivate the active MuDR elements in the Mop1-1 line. To accomplish this, a Mop1-1 homozygote was crossed to a plant from a family carrying MuKiller (MuK) a factor that dominantly inactivates the Mutator system (Lisch and Freeling 1994). Details of these crosses are provided in Materials and methods within this example.

Figure 13A:
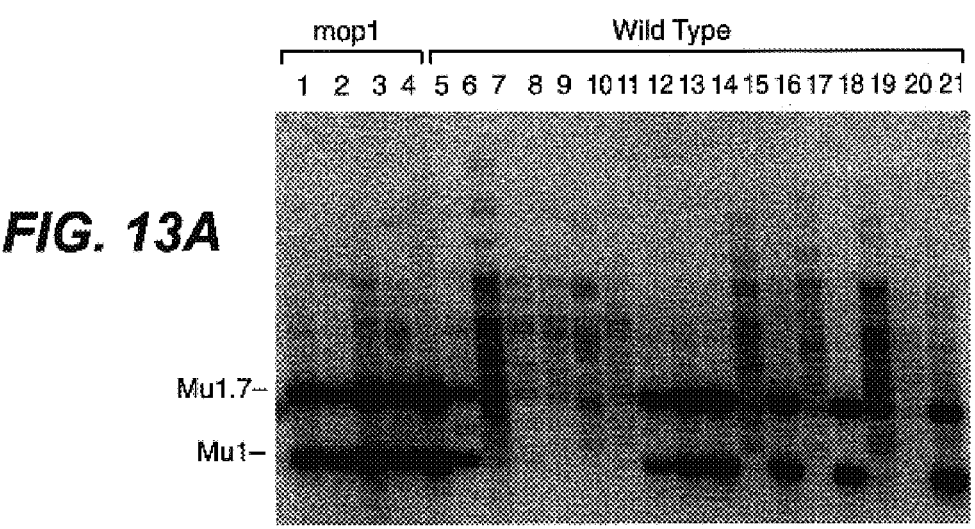
FIG. 13 shows the methylation status of MuDR and Mu1 elements in a family segregating for MuK and Mop1-1. A) A HinfI digest of DNA from this family probed with a Mu1 internal fragment. The lanes marked "Mop1" (lanes 1–4) indicate samples from plants that were homozygous for Mop1-1. The lanes marked "wild type" (lanes 5–21) indicate samples from plants that were either Mop1-1/Mop1 or Mop1/Mop1. The hypomethylated Mu1and slightly larger Mu1.7 kb fragments are indicated. B) To control for complete digestion by the restriction enzyme, the blot shown in A was stripped and rehybridized with a fragment of the a1 gene. C) A SacI digest of the same DNA samples as are shown in panel A, probed with an internal MuDR fragment. The 4.8 kb MuDR internal fragment diagnostic for the presence of hypomethylated, intact MuDR elements is indicated. The individual in lane 20 was retested and the presence of methylated Mu1 elements was confirmed.
Figure 13B:
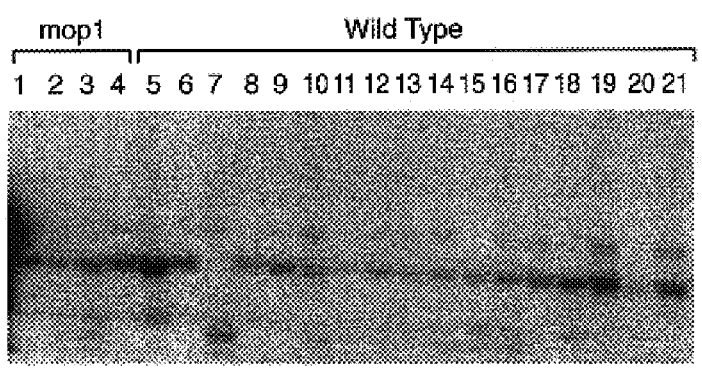
Figure 13C:
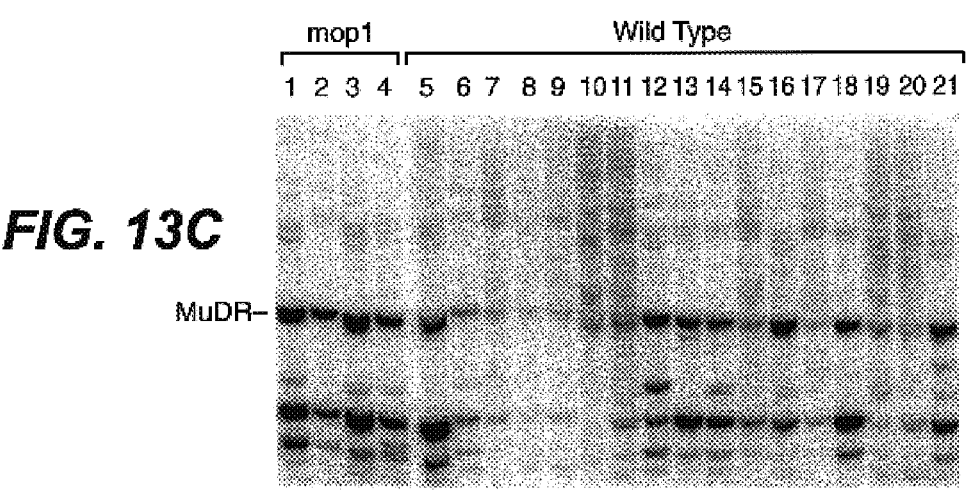
Figure 14A:
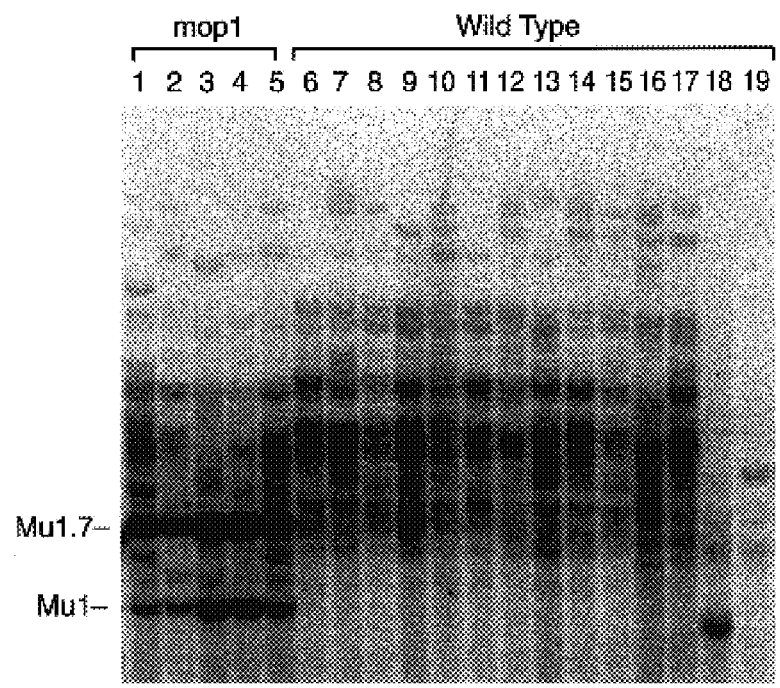
FIG. 14 shows the reversal of methylation of Mu1 elements in a family segregating for Mop1-1. A) A blot of a HinfI digest of DNA from a family segregating Mop1-1 homozygotes ("Mop1", lanes 1–5) and Mop1-1/Mop1-1 heterozygotes ("wild type", lanes 6–19) was probed with a Mu1 fragment. B) To control for complete digestion by the restriction enzyme, the blot shown in A was stripped and rehybridized with a fragment of the a1 gene. C) The same blot probed with the BglIII/SalI fragment from a region upstream of the b1 gene (see FIG. 4d). D) Gel blot analysis of DNA from progeny from the self-fertilization of the individual in lane 6 of panel A, a Mop1-1/Mop1 individual with methylated Mu1 elements. DNA from this family was digested with HinfI and probed with Mu1. Lanes marked with asterisks contain DNA from Mop1-1 homozygous individuals, as determined by pigment phenotype.
Figure 14B:
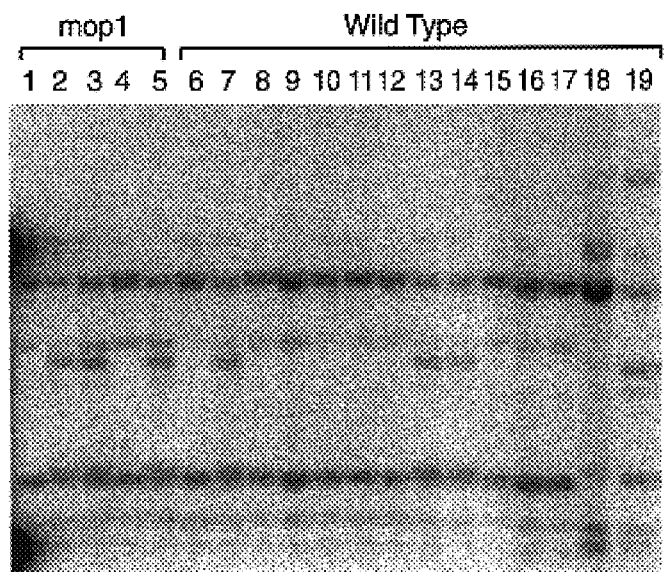
Figure 14C:
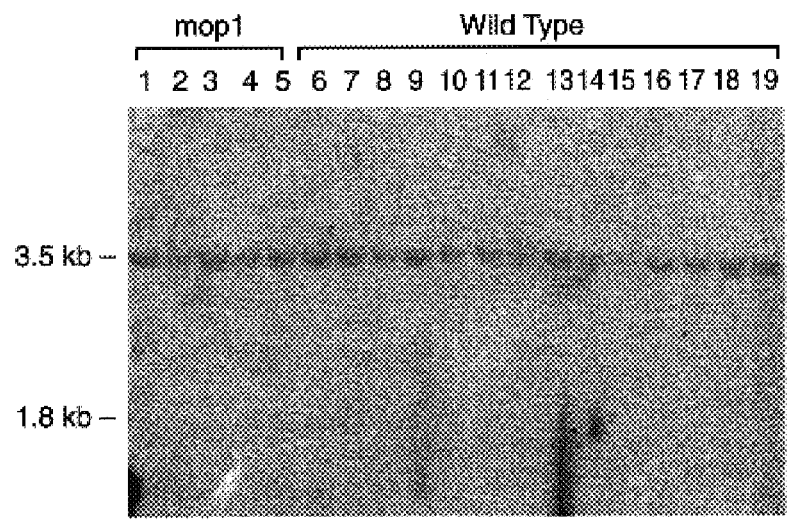
Figure 14D:
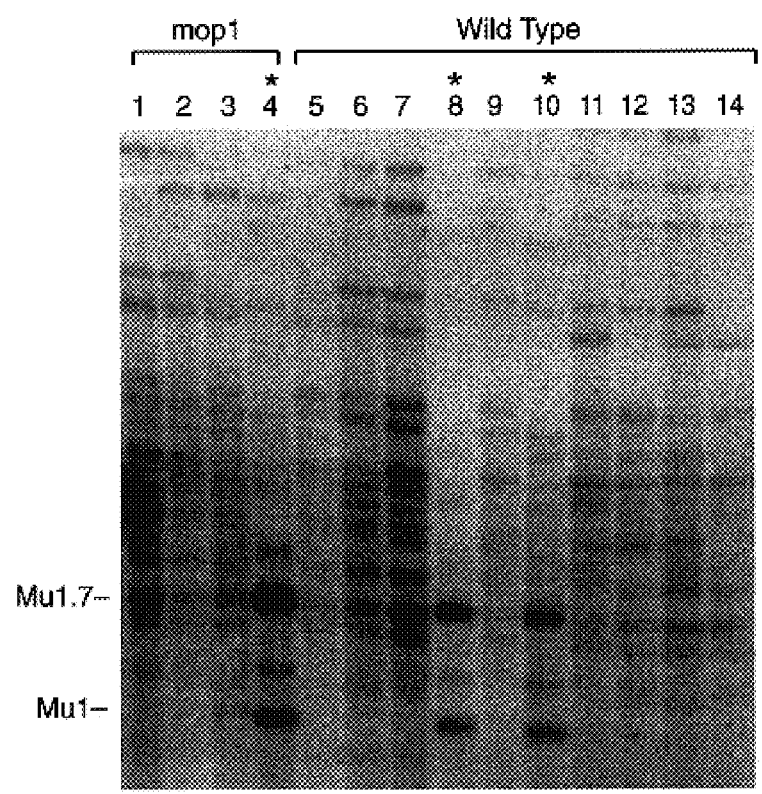

Several plants resulting from the cross between the Mop1-1 mutant and the plant carrying MuK were self-fertilized, and progeny were visually scored for the Mop1-1 phenotype (dark purple plants). The methylation status of both the autonomous MuDR elements and the non-autonomous Mu1 and related Mu1.7 elements was determined using DNA blots. One such family is shown in FIG. 13. In this family, 21 progeny were examined (Table 4, family 1162-3x). Four of the 21 plants exhibited a strong Mop1-1/Mop1-1 phenotype (lanes 1–4). As the parent of this family was B', the dark purple color of these plants was diagnostic for the presence of the Mop1-1 mutation. In addition to their dark pigment these plants were significantly shorter than their wild-type siblings, and none of them produced ears, consistent with previous observations of pleiotropic effects of this mutation (Dorweiler et al. 2000). To determine the effect of Mop1-1 on methylation of Mu1 elements due to MuK, DNA from these plants was digested with HinfI and probed with an internal Mu1 fragment (FIG. 13A). As a digestion control, the blot of the HinfI digest was probed with a fragment of the a1 gene flanked by HinfI sites that are not normally methylated (FIG. 13B). To assay for changes in methylation of MuDR termini, the same samples were digested with SacI and probed with an internal MuDR fragment (FIG. 13C). Because both of these enzymes are methylation sensitive, a reduction or elimination of the expected internal fragment is indicative of methylation of these sites.

Of the Mop1-1/Mop1 or Mop1/Mop1 siblings (lanes 5–21), half (9/17) had methylated Mu1 elements (FIG. 13A). The SacI digest revealed that although these particular plants did have the fragment diagnostic for at least one full length MuDR element, it was reduced in intensity and that reduction was accompanied by the appearance of additional, larger fragments (FIG. 13C). This observation is consistent with the methylation of sites within both MuDR and Mu1 TIRs seen previously in plants undergoing epigenetic silencing (Chandler and Walbot 1986, Martienssen and Baron 1994, Lisch and Freeling 1994), and is presumably due to the activity of MuK in this family. In contrast, none of the four Mop1-1 homozygotes had methylated Mu1 or MuDR elements.

Additional individuals from two other similarly derived families (Table 4, families 1181-1x and 1162-2x) were examined. A total of 41 progeny from self fertilizations of Mop1-1/Mop1 heterozygotes from this first generation were examined by both phenotype and DNA gel blot, including 10 Mop1-1 homozygotes and 31 of their wild-type siblings. The frequency of methylation of Mop1/Mop1 and Mop1/Mop1-1 individuals depended on the methylation status of the parent. In the two families generated from the self-fertilization of plants that had hypomethylated Mu1 elements (1162-3x and 1181-1x), a total of 13 of the 24 plants with the wild-type phenotype (Mop1/Mop1 or Mop1-1/Mop1) had methylated Mu1 elements. In the family generated from a parent that already had methylated Mu1 elements (1162-2x), all seven of seven wild-type progeny had methylated Mu1 elements. In contrast, the Mu1 elements in all 10 of the Mop1-1/Mop1-1 homozygotes from the three families carried hypomethylated Mu1 elements. Given the frequency of methylated Mu elements in their wild-type siblings, we can expect with 99.9% confidence that at least one of the mutants would have had methylated Mu1 elements if Mop1-1 were not affecting methylation.

To test the heritability of this phenomenon, Mop1-1 homozygotes from the family shown in FIG. 13 were crossed to three different Mu inactive hypermethylated wild-type siblings. One family produced no Mop1-1 plants, suggesting that the inactive parent lacked the Mop1-1 mutation. Two other families (1510 and 1511) segregated for the Mop1-1 phenotype in the expected ratio (14/29 and 5/17 dark progeny, respectively). An analysis of family 1511 is shown in FIG. 14. Family 1511 was derived from a cross between the two siblings shown in FIG. 13 (that in lane 4 by that in lane 15). In both of these families, all of the resulting Mop1-1/Mop1-1 plants carried hypomethylated Mu1 elements. In contrast, none of the wild-type Mop1/Mop1-1 plants carried hypomethylated Mu1 elements (Table 4).

TABLE 4

Methylation of Mu in Families Segregating for the mop1-1 Mutation

| | male: Mu-active, mop1-1/mop1-1 | | | self: Mu-active; mop1-1/Mop1 | | |
|---|---|---|---|---|---|---|
| | female: Mu-inactive, mop1-1/Mop 1 | | | | | |
| | Male 1511 | Female 1510 | Total | Self 1162-3x | Self 1181-1x | Total |
| mop[a] | 5 | 14 | 19 | 4 | 3 | 7 |
| mop methylated | 0 | 0 | 0 | 0 | 0 | 0 |
| non-mop[b] | 12 | 15 | 27 | 17 | 7 | 24 |
| non-mop methylated | 12 | 15 | 27 | 9 | 4 | 13 |
| total plants assayed | 17 | 29 | 46 | 21 | 10 | 31 |

| | Mu-inactive; mop1-1/Mop1 | | | | |
|---|---|---|---|---|---|
| | Self | Self | Self | Self | Grand total |
| self: | 1510-9x | 1510-1x | 1162-2x | 1511-6x | total |
| Mop | 3 | 1 | 3 | 3 | 10 | 36 |
| Mop methylated | 0 | 0 | 0 | 0 | 0 | 0 |
| non-mop | 7 | 13 | 7 | 11 | 38 | 89 |
| non-mop methylated | 7 | 13 | 7 | 11 | 38 | 78 |
| total plants assayed | 10 | 14 | 10 | 14 | 48 | 125 |

[a] mop1/mop1 homozygotes showing the dark purple plant phenotype
[b] mop1/Mop1 or Mop1/Mop1, not showing the dark purple plant phenotype The Mop1-1 mutation reverses the effects of previous methylation of the Mu elements. To confirm that the Mop1-1 mutation could reverse previously established Mu1 element methylation, several plants that were heterozygous for Mop1-land that carried methylated Mu1 elements (FIG. 14) were self-fertilized. The resulting families were scored for both the Mop1-1 phenotype (dark purple pigment) and methylation of Mu1 elements (families 1510-1x, 1510-9x, and 1511-6x, Table 4). In the figure, one individual from family 1511 (Panel A, lane 6) was self-fertilized to give rise to family 1511-6x (Panel D). Consistent with the segregation of a single recessive mutation, roughly one quarter (7/38) of all of these progeny had the Mop1-1 phenotype (Table 4). All 7 of the Mop1-1/Mop1-1 homozygotes examined had hypomethylated Mu1 elements relative to their wild-type siblings, all of which carried methylated Mu1 elements. Thus, the Mop1-1 mutation reverses previously established methylation of Mu1 elements.

Figure 15A:
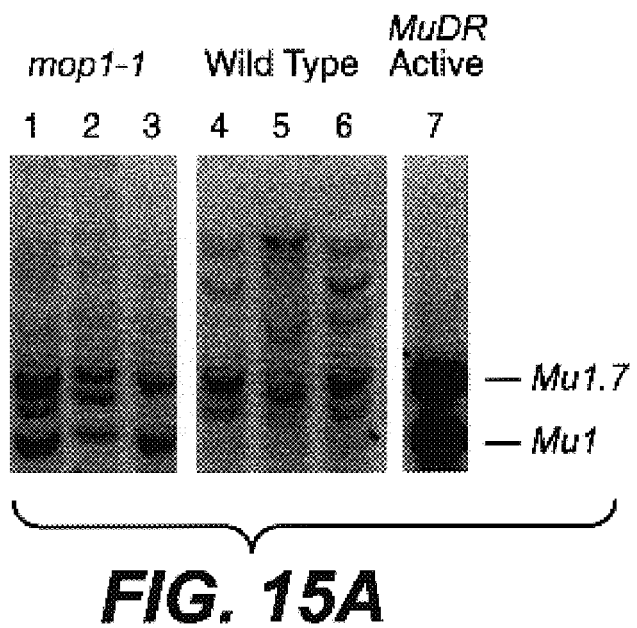
FIG. 15 shows the hypomethylation of Mu1 in the absence of MuDR. A) A HinfI digest of DNA from a family segregating for Mop1-1/Mop1-1 ("Mop1-1", lanes 1–3) and Mop1-1/Mop1 or Mop1/Mop1 ("wild type", lanes 4–6). The resulting blot was hybridized with the Mu1 internal probe. B) DNA from the same family digested with SacI and probed with an internal fragment of MuDR. The diagnostic fragment for a full length MuDR element is as indicated. Digestions with methylation insensitive enzymes confirmed no intact MuDR elements were present (data not shown). In both panels, the last lane contains DNA from a MuDR-active individual.
Figure 15B:
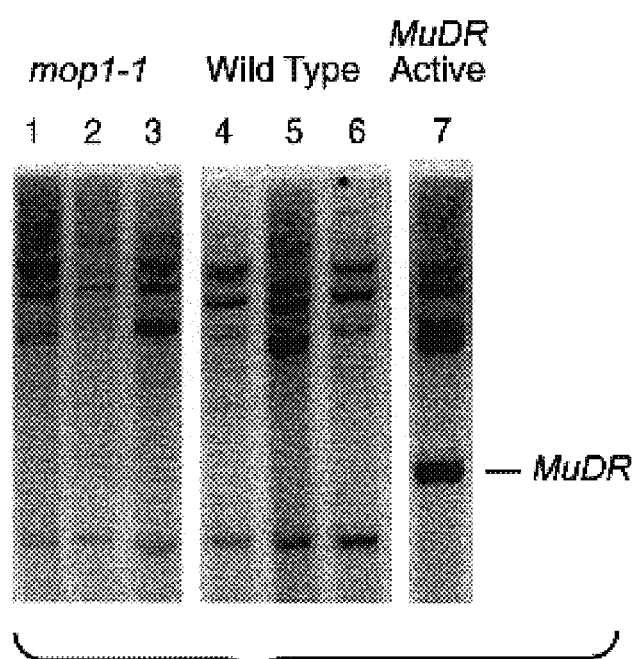

The Mop1-1 mutation reverses Mu1 methylation in the absence of full-length MuDR elements. Normally, there is a very tight correlation between hypomethylation of Mu1 elements and the presence of intact, functional MuDR elements, suggesting that the MuDR transposase is required to prevent a default methylation pathway that targets Mu elements (Chandler and Hardeman 1992). The Mop1-1 homozygous plants provide the first exception to this rule. Although Mop1-1 was derived from a Mutator line, we have identified several lineages that lack intact, functional MuDR elements. That is, they lack diagnostic fragments when digested with SacI (FIG. 15), XbaI, or with an EcoRI, HindIII double-digest (data not shown). Based on this observation, we conclude that these lines do not carry intact, functional MuDR elements. Despite this, we find that the Mop1-1 plants in these lines still carry hypomethylated Mu1 elements. We examined two families in more detail, one of which is shown in FIG. 15. In these families, which were the products of the self-fertilization of plants heterozygous for Mop1-1, hypomethylation of Mu1 cosegregated with the Mop1-1 phenotype. Including the individuals shown in FIG. 15, a total of eight Mop1-1 mutant and eight wild-type siblings were examined. The Mu1 elements of all of the Mop1-1 plants were hypomethylated relative to the Mu1 elements of their wild type siblings.

A Second allele of Mop1 also hypomethylates Mu1. To eliminate the possibility that there was a factor modifying Mu1 methylation that was only coincidentally linked to Mop1-1, we also examined a family segregating a different allele of Mop1, Mop1-2EMS. This family was derived from a non-Mutator stock that had been EMS mutagenized (Hollick and Chandler 2001). DNA from six Mop1-2EMS mutants and six Mop1/Mop1-2EMS siblings were digested with HinfI and probed with Mu1. As with Mop1-1, the Mu1 elements in the mutant plants were significantly less methylated than their wild-type siblings (data not shown).

Figure 16D:
FIG. 16 shows gel blots of digests of DNA from mutant ("Mop1") and wild type ("w.t.") individuals using several methyl-sensitive enzymes. A) ApaI/BamHI. Lanes 1–7 are Mop1-1 homozygotes. Lanes 8–14 are heterozygous siblings. Lanes 15 and 16 are Mop1-1 homozygous and wild type individuals digested with only BamHI. B) SalI/BamHI. Lanes 1–4 are Mop1-1 homozygotes, lanes 5–8 are wild type. C) PvuII/BamHI. Lanes 1–4 are Mop1-1 homozygotes, lanes 5–8 are wild type. D) Restriction map of the region upstream of the start of transcription of B' and B-1 (the sequence of these alleles are identical in this region). Sites marked with an asterisk are partially or completely methylated in plants carrying B' Mop1/Mop1; B-1 Mop1/Mop1, or Mop1/Mop1-1; or B' Mop1/Mop1-1. The other sites are unmethylated in all genotypes tested. A=ApaI, B=BamHI, Pv=PvuII, H=HinfI, Sa=SalI. The bar above the map indicates the probe.

The Mop1-1 mutation does not reverse methylation of sites immediately upstream of the b1 locus. Given that the Mop1-1 mutation reverses Mu1 methylation, we wanted to determine whether or not it affects methylation of sequences elsewhere in the genome. We were particularly interested in examining sequences around B', as mutations in Mop1 increase transcription of B' (Dorweiler et al. 2000). There are a number of sites upstream of the B' and B-I transcription unit (these alleles share identical restriction maps) that have been previously assayed for methylation status (Patterson et al. 1993, Patterson et al. 1995) (GenBank, accession no. X70790 S48060). No differences in methylation had been observed between B-I and B' plants, suggesting that, unlike the situation at the r1 locus, methylation in the promoter proximal and 5' untranslated region is not correlated with the 10–20 fold difference in transcription. The methylation status of various restriction sites upstream of B' and B-I is shown in FIG. 16. We observed no difference between B' Mop1-1, B' Mop1/Mop1-1, and B-I Mop1 plants at the HinfI site 1.8 kb upstream of the transcriptional start site (FIG. 14, panel C) or between Mop1-1 homozygotes and heterozygotes at the ApaI, SalI, or PvuII sites (FIG. 16). Each of the last three digests was performed in combination with BamHI. The complete absence of the expected 12 kb BamHI fragment in each of the double digests suggests that at least one of the sites recognized by the methyl-sensitive enzyme in each double digest was digested to completion. Thus, partial digestion of any specific site was due to methylation, rather than incomplete digestion. Interestingly, these sites are all within transposable elements, suggesting that methylation of transposons in the promoter proximal region of B' is not affected by Mop1-1. These elements include a MITE element immediately upstream of the start of transcription and the Muse element (a distant relative of MuDR; V. Chandler, D. Selinger and M. Stam, personal observation). Together, these data suggest that Mop1-1 is not a global regulator of transposon methylation.

Progeny of plants homozygous for the mop1-1 mutation for multiple generations can show Mu element somatic excision: To determine if reactivation could occur in subsequent generations, one family segregating for both the Mop1-2EMS mutation and a single silenced MuDR element was planted, subjected to DNA gel blot analysis, and out-crossed. Nine plants from this family were examined. Four of the nine plants contained hypomethylated Mu1 elements, consistent with good penetrance of this aspect of the mop1-2EMS phenotype. Using a probe flanking the single MuDR element in this family, the presence of MuDR was confirmed in five of the nine plants. Two plants carried both hypomethylated Mu1 elements (Mop1-2EMS homozygotes) and the silent MuDR element. One of these plants died. The other was self-fertilized and out crossed to a plant that was Mop1-1/Mop1 and a1-mum2. None of the 288 progeny kernels from the self-fertilization or the 241 kernels from the outcross showed excision of Mu1 from a1-mum2.

To explore this issue further, we used a more sensitive assay, reactivation of somatic excision of a reporter Mu1 element. Plants that lacked full-length MuDR elements and that were homozygous for Mop1-2EMS (the EMS-induced allele of Mop1) were crossed to plants homozygous for a single MuDR element that had been silenced using MuKiller (see Materials and Methods within this Example for details of the cross). The resulting plants were either self-fertilized, or crossed to plants homozygous for a1-mum2, and Mop1-2EMS. The resulting ears were screened for the appearance of spotted kernels. If Mop1-2EMS could activate the silenced MuDR elements, 2.34% of the progeny kernels from the self fertilizations, or 6.25% of the test cross progeny kernels would be expected to have excisions. Twenty-two families consisting of a total of 6,324 progeny kernels resulting from self-fertilization were examined. The expected number of spotted kernels in these families was 148 (see Materials and Methods within this Example for calculation). Three families with a total of 710 kernels generated from out crosses to a1-mum2 testers were also examined. If MuDR elements were reactivated by Mop1-2EMS, we would have expected to see 45 spotted kernels in these families. None were observed in any of these families, indicating no reactivation of the silenced MuDR element.

To determine if reactivation could occur in a subsequent generation, one family segregating for both the Mop1-2EMS mutation and a single silenced MuDR element was planted, subjected to DNA gel blot analysis, and out-crossed. Nine plants from this family were examined. Four of the nine plants contained hypomethylated Mu1 elements, consistent with good penetrance of this aspect of the Mop1-2EMS phenotype. Using a probe flanking the single MuDR element in this family, the presence of MuDR was confirmed in five of the nine plants (data not shown). Two plants carried both hypomethylated Mu1 elements (Mop1-2EMS homozygotes) and the previously silent MuDR element. One of these plants died. The other was self-fertilized and out crossed to a plant that was Mop1-1/Mop1 and a1-mum2. None of the 288 progeny kernels from the self-fertilization or the 241 kernels from the outcross showed excision of Mu1 from a1-mum2.

These results indicate that even two generations of exposure to Mop1 mutations is insufficient to reactivate the silenced, but hypomethylated MuDR element in this genetic background.

To determine whether or not MuK, which may have been in this lineage, was contributing to the continued repression of Mu1 somatic excision, despite the presence of Mop1-2EMS, an additional generation was examined. Even if MuK had been homozygous in the original plant, two generations of out crossing would result in half of the progeny lacking MuK. Therefore, fifty pale seeds of the 241 seeds from the first outcross described above were planted. DNA from the resulting 45 plants was isolated and subjected to DNA gel blot analysis, which confirmed that half of the plants (23) carried the MuDR element at position p1 MuDR (p1). Slightly less than one half (18) were homozygous for Mop1-2EMS mutant. DNA blot analyses demonstrated that the Mu1 elements in all of the mop 1-2EMS homozygous plants were hypomethylated relative to their wild type siblings. None of the wild type plants carried any hypomethylated Mu1 elements. One fifth of the plants (8) were homozygous for both Mop1-2EMS and had MuDR at the p1 position. These plants were outcrossed again to plants that were heterozygous for Mop1-2EMS and homozygous for a1-mum2 and R-g. Importantly, some of the progeny kernels of the plants that had been homozygous Mop1-2EMS homozygous and that carried MuDR(p1) showed Mu1 excision from the a1-mum2 allele. Of six ears from plants with this genotype, four ears had some spotted kernels (a total of 29 of 642 kernels were spotted). The excision frequency in these kernels was variable, ranging from only a few excisions per kernel to a frequency typical for a single active MuDR element. In contrast, in 13 ears generated from plants that were heterozygous for Mop1-2EMS and that carried MuDR(p1) there were no spotted kernels out of a total of 3309 pale kernels. Similarly, in 9 ears generated from plants that were homozygous for Mop1-2EMS but which lacked MuDR(p1) there were no spotted kernels out of 1900 pale kernels, and in five ears generated from plants that were heterozygous for Mop1-2EMS and that lacked MuDR(p1), there were no spotted kernels out of 989 pale kernels. The presence of spotted kernels only in the plants homozygous for Mop1-2EMS and carrying MuDR(p1), strongly suggests that contamination by pollen carrying active MuDR is an unlikely explanation for the spotted kernels. Based on these data, we conclude that in the absence of MuK, and after two generations of exposure of Mop1-2EMS, this mutation can cause reactivation of silenced MuDR elements.

Example 3

Isolation of Mop1-2EMS, rmr1-1, rmr1-2 and rmr2-1 Mutants

Genetic Stocks. All stocks contain dominant, functional alleles for all genes required for the production of anthocyanin pigments in seedling and anther tissues unless otherwise noted. Pistillate parents used for the mutagenesis experiment had the following pl1 and r1 genotypes: Pl'; R-r or R-r/R-g. Staminate parents for the mutagenesis experiment were originally obtained from the Maize Cooperation Stock Center (Urbana, Ill.; accession no. 611A: Pl-Rh sm1; R-r). The salmon silks 1 locus is 10 cM distal to pl1. The recessive sm1 allele confers salmon colored silks when homozygous and thus provides a linked morphological marker to Pl-Rh. The Pl' testers used for initial crosses with putative mutants were obtained via spontaneous paramutation of Pl-Rh (Hollick et al. 1995). A632 (pl-A632; R-r), A619 (pl-A619; R-g) and W22 (pl-W22; R-g) inbred material was obtained from the USDA North Central Plant Introduction Station, (Ames, Iowa). Additional W22 stocks (pl-W22; R-r:standard) were provided by Jerry Kermicle (Univ. of Wisconsin, Madison). Five Pl-Rh/Pl-Rh tester stocks of different genetic backgrounds were used in crosses to determine whether or not mutant plants carried paramutagenic Pl' alleles. Material for pl1 RNA measurements was produced by crossing plants homozygous for the given EMS-derived mutation by sibling plants heterozygous for the same mutations. Additional details of the specific genetic stocks used for these experiments are available upon request.

Pollen Mutagenesis. Pollen pooled from multiple tassels was treated with EMS and applied to silks according to Neuffer and Coe (1978). Pistillate parents were derived from two related Pl'/Pl' families. Both families together yielded 345 ears with an average of 49 kernels per ear. Germination frequency was approximately 77% for the first 7500 M1 seed planted. A total of 9000 M1 seedlings were screened for dominant mutations affecting pigment production. Seedlings were grown in potting flats at an approximate density of 100 per sq ft. Approximately 1000 M1 plants were grown to maturity and self-pollinations of M1 plants generated 495 M2 families.

Seedling Screens. M2 families of 30 seeds each were germinated in unheated sand benches and grown under high-intensity lighting (1660 □E/m2 sec using a 1:1 mixture of sodium vapor and metal halide lamps). Visible seedling phenotypes (Table 5) were noted between 14 and 18 days post-imbibition.

TABLE 5

EMS-derived $M_2$ seedling mutations

| Mutant Class | Number of EMS-Derived Mutations | Frequency of EMS-Derived Mutations | Frequency of EMS-Derived Mutations (Neuffer) |
| --- | --- | --- | --- |
| Chlorophyll deficient Albino | 15 | .09 | .13 |
| Lemon white | 21 | .12 | .037 |
| Yellow green | 14 | .08 | .015 |
| Pale green | 16 | .09 | .015 |
| Variable mutants | | | |
| Piebald | 1 | .006 | .03 |
| Striped | 12 | .076 | .09 |
| Premature chlorosis | 7 | .04 | NR |

TABLE 5-continued

EMS-derived M$_2$ seedling mutations

| Mutant Class | Number of EMS-Derived Mutations | Frequency of EMS-Derived Mutations | Frequency of EMS-Derived Mutations (Neuffer) |
| --- | --- | --- | --- |
| Cross-banded | 3 | .02 | NR |
| Seedling lethals | 37 | .21 | .12 |
| Glossy | 8 | .05 | .026 |
| Dwarf | 6 | .04 | NR |
| Others | 63 | .36 | .29 |

The number and frequency of visible mutations identified in the current M2 screen are compared with the frequency of similar mutations identified from an earlier EMS pollen mutagenesis (Neuffer 1978). NR: None Reported.

Genetic Crosses and Stock Syntheses. Hand pollinations were used for all genetic crosses. Material for the sm1, rmr1 cosegregation test was derived by crossing a single plant heterozygous for ems136 and homozygous sm1 to a plant homozygous for ems235 but heterozygous for the recessive sm1 allele. The following syntheses and analyses were used to generate material to test the effects of the EMS-derived mutations on neutral pl1 alleles. Plants heterozygous for a given mutation (Pl' anthers) were crossed to both the A632 inbred line and a W22 line (obtained from J. Kermicle, Univ. of Wisconsin, Madison) containing the weakly expressed pl1 alleles pl-A632 and pl-W22 respectively. The pl-A632, pl-W22, and Pl-Rh alleles are all distinct based on RFLP analyses (J. Hollick, unpublished). F1 plants were either self pollinated (A632 material) or backcrossed to plants homozygous for the given mutation (W22 material). F2 (A632 material) and BC1 (W22 material) progeny were grown to maturity. The pl1 genotypes of all plants in the F2 and BC1 families were determined using RFLP gel blot analysis as previously described (Hollick et al. 1995). Anther phenotypes of all homozygous pl-A632 F2 plants were photographed for later comparison. All homozygous pl-A632 F2 plants were crossed to plants heterozygous for the given EMS-induced mutation to determine whether the F2 plants were also homozygous for the given EMS-induced mutation. Two F2 plants were identified that were homozygous pl-A632 by RFLP analysis and homozygous for rmr1-1 by testcross analysis and five F2 plants were identified that were homozygous pl-A632 by RFLP analysis and homozygous for rmr2-1 by testcross analysis. Examination of the anther photographs did not indicate any pigment differences between A632 inbred anthers or any F2 pl-A632 plants regardless of whether or not they carried the EMS-induced mutations. The BC1 plants that were Pl'/pl-W22 were self pollinated and also crossed to plants heterozygous for a given EMS-induced mutation to identify BC1 plants that were also homozygous for EMS-induced mutations. Anther pigmentation of pl-W22/pl-W22; rmr1-1/rmr1-1 and pl-W22/pl-W22; rmr2-1/rmr2-1 plants was weak and not obviously different from the anther pigmentation of heterozygous siblings or grandparental W22 plants.

RNA Measurements. RNA isolations from anther tissues and RNase-protection assays were performed as described in Example 1.

Pollen mutagenesis generated new maize mutations. The number of mutable loci affecting paramutation-based gene silencing is unknown. To identify such loci, we performed chemical mutagenesis using ethyl methanesulfonate (EMS) to produce a high frequency of new maize mutations. M1 seed was obtained by applying EMS-treated pollen from Pl-Rh/Pl-Rh plants to the silks of receptive Pl'/Pl' ears. A total of 495 M2 families were subsequently generated by self pollination of M1 plants to screen for recessive mutations. Small M2 families (30 seeds each) were grown for 14–18 days and then visually examined for germination frequencies and unusual morphological phenotypes. Table 5 outlines the frequency of mutant phenotypes identified. Observed mutation frequencies are similar with previous EMS-pollen mutageneses (Neuffer 1978) indicating that our chemical mutagenesis was highly efficient in producing new maize mutations.

Dominant Mutations Affecting Pl' Expression Were Not Found. Because the primary leaf sheath of Pl'/Pl-Rh seedlings is normally weakly pigmented (Hollick et al. 1995), dominant EMS-induced mutations that either release Pl' from a repressed expression state or prohibit the establishment of paramutation might be expected to confer fully colored M1 seedling phenotypes. Sixteen out of 9000 M1 seedlings examined were fully colored. However, no flowering plants from these 16 fully colored seedlings had fully colored, Pl-Rh-like, anthers. This result indicates that our seedling screen for dominant mutations affecting anther pigmentation has an approximate 0.2% false-positive rate. In addition, none of the approximately 1000 M1 plants grown to maturity had a Pl-Rh phenotype. Thus, no dominant mutations affecting either the establishment of pl1 paramutation or the maintenance of Pl' repression were identified out of 10,000 M1 plants tested.

Genetic screens identified recessive mutations affecting seedling and anther pigmentation. Recessive mutations that release Pl' from a repressed expression state might also be expected to confer fully colored seedling phenotypes (FIG. 17). Our M2 screen, identified five families (nos. 60, 96, 136, 235, 240) that segregated fully colored seedlings to weakly colored seedlings in the following ratios (60, 4:23; 96, 1:29; 136, 6:24; 3847 235, 3:25; 240, 8:16). In four of five families, fully colored seedlings gave rise to mature plants with fully pigmented Pl-Rh-like anthers (FIG. 18A). Material from family 60 was dropped from further analyses because plants from fully colored seedlings in family 60 did not have fully pigmented anthers.

Genetic segregation tests indicated that the Pl-Rh-like phenotypes seen in three of the M2 families (nos. 96, 136, and 235) were heritable as single locus recessive traits. Plants with fully colored anthers derived from the three M2 families were first crossed with Pl'/Pl' plants to complement the putative recessive mutations. All F1 plants from these crosses had a clear Pl' phenotype (family 96, 35/35; family 136, 36/36; family 235, 36/36) indicating that the putative mutations affecting seedling and anther color are recessive. F1 plants from families 96, 136 and 235 were self pollinated to recover the fully colored seedling and anther trait. In all three cases, fully colored anther phenotypes were recovered at roughly a 1:3 ratio in F2 families (Table 6) consistent with the interpretation that Pl-Rh-like phenotypes are due to single locus recessive mutations. As expected, subsequent crosses between mutant plants and heterozygous siblings gave rise to families in which the mutant and normal phenotypes approximated a 1:1 ratio (family 96, 231:272; family 136, 100:88; family 235, 111:125).

TABLE 6

Inheritance of EMS-induced mutations

| EMS Allele | Pl-Rh Anthers | Pl' Anthers | Frequency of Plants with Pl-Rh Anthers |
|---|---|---|---|
| ems96 | 8 | 33 | 0.24 |
| ems136 | 9 | 52 | 0.17 |
| ems235 | 46 | 170 | 0.27 |

EMS-induced factors affecting Pl' are inherited as single gene recessive mutations. The number and frequency of plants with fully colored anthers are indicated for the following number of F2 families: ems96, 3 families; ems136, 4 families; ems235, 6 families.

Complementation Tests Define Three Loci. Genetic complementation was tested in pair-wise combinations among the four EMS-induced mutations and also with the recessive a3-Styles allele (Styles and Coe 1986) and the recessive Mop1-1 allele (Dorweiler et al. 2000). Specific EMS-induced mutations were designated according to the family in which they were identified: ems96, ems136, ems235 and ems240. For each mutation, plants heterozygous for a given mutation (Pl' anthers or lightly colored plant in the case of a3-Styles heterozygotes) were individually crossed by plants homozygous for a different allele (Pl-Rh-like anthers or darkly colored plants in the case of a3-Styles homozygotes). Anther pigment phenotypes of progeny from these crosses were quantified (Table 7) on a 1–7 graded Anther Color Score (ACS) where ACS 7 corresponds to the fully colored Pl-Rh phenotype (Hollick et al. 1995). Based on these results, mutations ems136 and ems235 fail to complement and thus define a single locus, ems240 is allelic to Mop1-1, and ems96 defines a third locus. Further description of the ems240 allele, designated Mop1-2EMS, is provided in Example 1.

TABLE 7

Complementation Tests

| Alleles Tested | Ears Examined | Number of Plants with Given Anther Color Score | | | | | | |
|---|---|---|---|---|---|---|---|---|
| | | 1 | 2 | 3 | 4 | 5 | 6 | 7 |
| ems96 | | | | | | | | |
| a3-Styles | 4 | 1 | 11 | 98 | 2 | 0 | 0 | 0 |
| mop1-1 | 1 | 6 | 6 | 1 | 0 | 0 | 0 | 0 |
| ems136 | 3 | 8 | 26 | 12 | 1 | 0 | 0 | 0 |
| ems235 | 5 | 10 | 37 | 27 | 1 | 0 | 0 | 0 |
| ems240 | 4 | 9 | 46 | 19 | 4 | 0 | 0 | 0 |
| ems136 | | | | | | | | |
| a3-Styles | 2 | 1 | 7 | 20 | 1 | 1 | 0 | 0 |
| mop1-1 | 1 | 9 | 6 | 1 | 0 | 0 | 0 | 0 |
| ems235 | 3 | 8 | 14 | 2 | 0 | 0 | 0 | 26 |
| ems235 | | | | | | | | |
| a3-Styles | 2 | 0 | 5 | 28 | 3 | 2 | 0 | 0 |
| mop1-1 | 1 | 3 | 11 | 0 | 0 | 0 | 0 | 0 |
| ems240 | 2 | 0 | 8 | 11 | 4 | 1 | 0 | 0 |
| ems240 | | | | | | | | |
| mop1-1 | 1 | 0 | 2 | 5 | 0 | 0 | 0 | 11 |

Complementation tests identify three unique loci. For each allele listed in bold text, the underlying series of alleles were tested for complementation. The number of ears sampled for each test are indicated along with the total numbers of mature plants with a given Anther Color Score derived from the seeds off those ears.

Figure 21A:
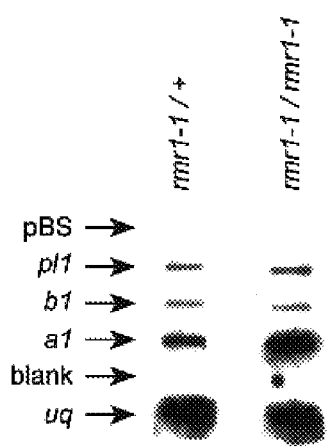
FIGS. 21A–B show results of in vitro transcription reactions comparing B-I/B-I; PI'/PI'; rmr1-1/rmr1-1 and B-I/B-I; PI'/PI', rmr1-1/rmr1 (closed bars) and B-I/B-I; PI'/PI'; rmr1-1/rmr1-1 and B-I/B-I; PI'/PI'; rmr1-1Rmr1 (open bars) husk tissues. (A) shows one example of the primary results while (B) represents combined results from 5 independent experiments. Experimental design and representation of results are as described in Hollick et. al 2000.
Figure 21B:
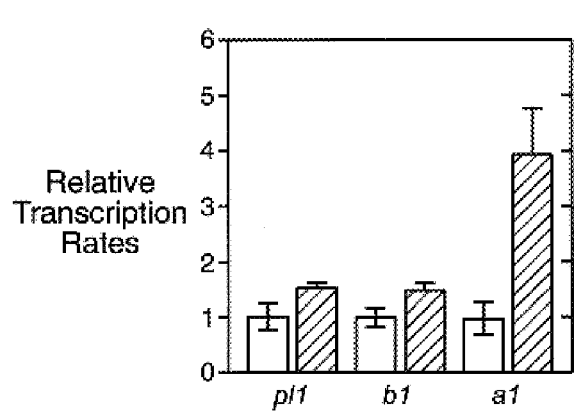
Figure 24A:
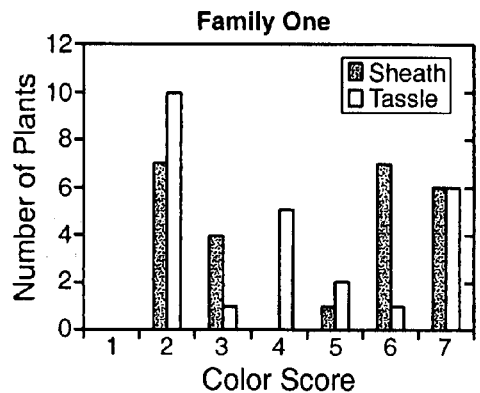
FIG. 24 (Families one through nine) shows the segregation of B-I phenotypes among progeny of gl2 B-I wt×Mop2-1 B'. B' individuals heterozygous for Mop2-1 were crossed to B-I and progeny were scored for sheath and tassel pigment levels. A color score of 1–3 is typical of a B' individual, and 6–7 is typical of a B-I individual. The distribution of color scores among progeny from nine B' individuals heterozygous for the Mop2-1 mutation crossed to B-I are shown graphically in panels 24A through 24I. Some families show a clear bimodal distribution whereas others have a higher frequency of intermediate individuals.
Figure 24B:
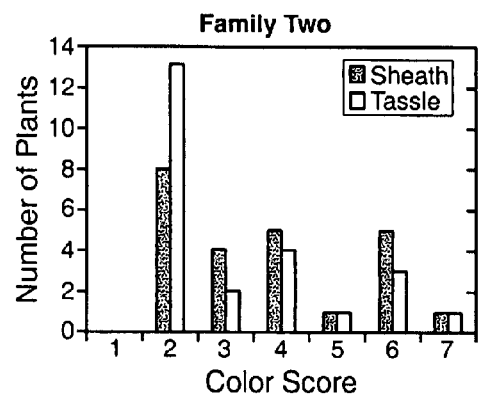
Figure 24C:
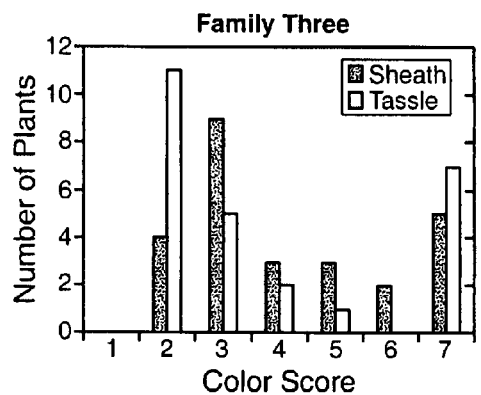
Figure 24D:
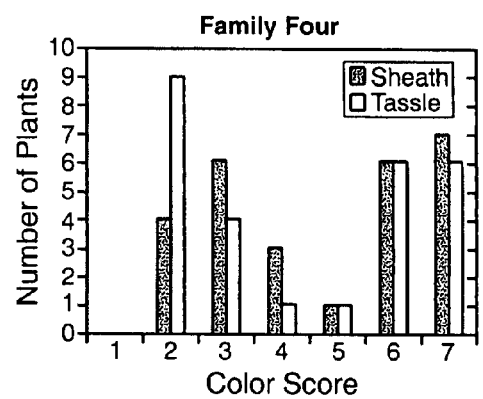
Figure 24E:
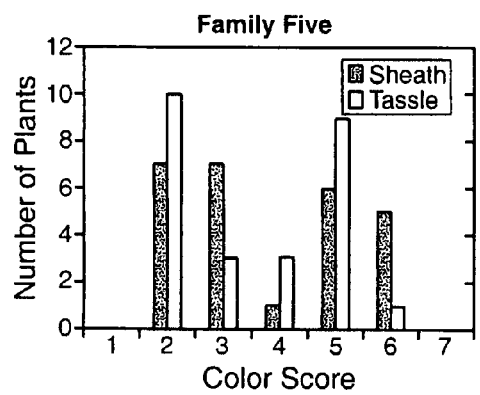
Figure 24F:
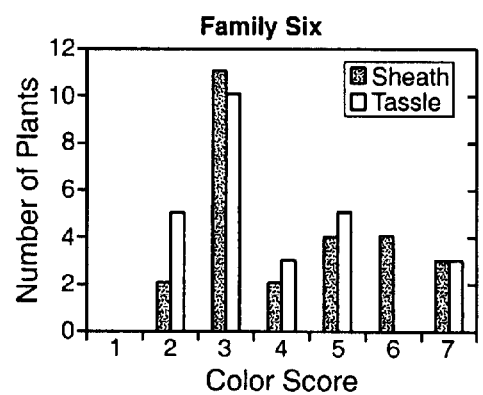
Figure 24G:
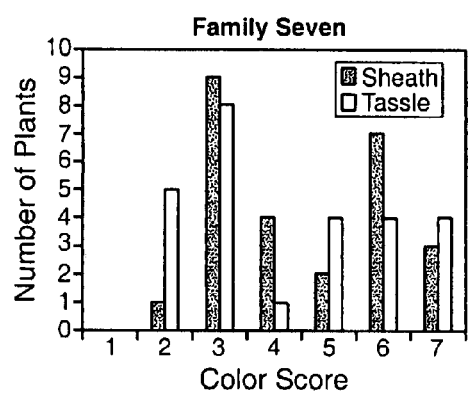
Figure 24H:
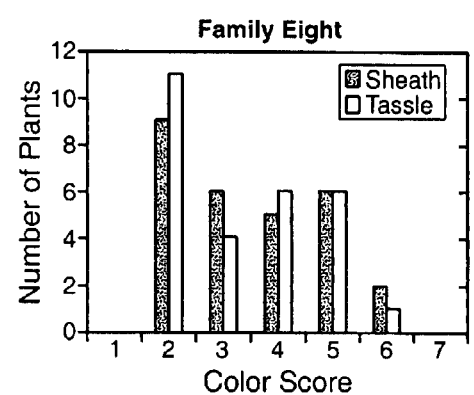
Figure 24I:
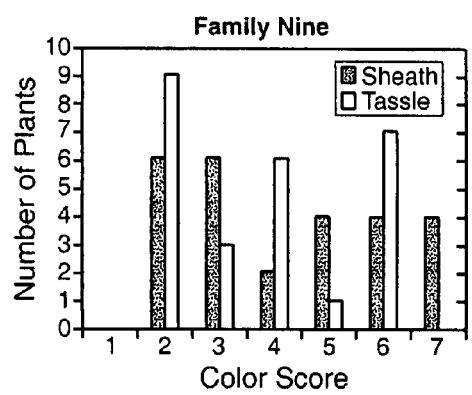

EMS-Derived Mutations Allow Increased Expression of pl1 RNA. We used RNase-protection experiments to compare pl1 RNA levels from anthers of Pl'/Pl' plants either homozygous or heterozygous for the ems136, ems235, or ems96 alleles. Using actin RNA as a control, pl1 RNA levels were 26, 14, and nine fold greater in homozygous ems136, ems235 and ems96 mutants versus heterozygous siblings, respectively (FIGS. 18B and 18C). These increases in pl1 RNA due to the ems136 mutation occur in the absence of any changes in the transcription rate of the pl1 gene. In vitro transcription reactions using isolated husk nuclei (see example 1), demonstrate that both pl1 and b1 transcription rates remain unchanged while a1 transcription is increased 4-fold in homozygous ems136 plants (5 independent experiments) (FIG. 21). However, the pl1 RNA increases due to the ems235 mutation occur with concomitant increases in pl1 transcription rates. In vitro transcription reactions using isolated husk nuclei (see example 1), demonstrate that pl1 transcription rates are increased 2.5-fold in homozygous ems235 plants (5 independent experiments) (FIG. 22). The b1 transcription rate remains unchanged and the a1 transcription rate is increased 5-fold. These results indicate that the normal functions of these genes identified by mutations are required to maintain repression of pl1 RNA accumulation. The transcription assays imply that there are both transcriptional and post-transcriptional regulatory mechanisms involved in maintaining the repression of paramutant Pl'.

Genes Affecting Repression of Pl' Encode Trans-Acting Factors. Both Mop1 and the locus defined by the ems96 allele genetically map to chromosome 2 whereas the pl1 locus is found on chromosome 6. Alleles that define the other locus (ems136 and ems235) failed to cosegregate with a genetic marker closely linked to the pl1 locus. The salmon silks 1 (sm1) locus, located 10 cM distal to pl1, normally conditions yellow maize silks but plants that are homozygous for the recessive sm1 allele (sm1) have salmon-colored silks. Genetic crosses were used to ask whether the fully-colored anther phenotype found in homozygous mutant plants cosegregated with the recessive sm1 allele. A total of 6/15 (40%) segregant plants with fully-colored anthers were sm1/sm1 and 9/21 (42%) plants with weakly-colored anthers were sm1/sm1. The lack of strong cosegregation between the fully-colored anther phenotype and recessive alleles of the sm1 locus indicates that the locus defined by the ems136 and ems235 alleles is distinct from the pl1 locus. Thus all three loci identified in our genetic screen define trans-acting genetic factors affecting pl1 RNA accumulation in Pl'/Pl' plants.

All Three Loci Identified by Mutation Encode Factors Required to Maintain Heritable Repression of Pl'. The fully-colored phenotypes of seedlings and anthers together with the increases in pl1 RNA seen when the EMS-derived mutations are homozygous suggested that Pl' may have changed to a Pl-Rh state. Plants homozygous for Mop1-1 sometimes show heritable changes of Pl' to Pl-Rh. To test mutations at the other two loci, mutant plants with fully-colored anthers were crossed to a series of Pl-Rh/Pl-Rh testers and the anther phenotypes of the progeny were quantified. If Pl' heritably changes to Pl-Rh in plants homozygous for the ems136, ems235, or ems96 alleles then fully-colored Pl-Rh phenotypes should be found in the resulting progeny. If Pl' does not heritably change to Pl-Rh, then only Pl' phenotypes would be found in the progeny (Hollick et al. 1995). Results of these crosses (Table 8) indicate that while Pl' can be transmitted, Pl' often changes to a meiotically-heritable Pl-Rh state in plants homozygous for the ems136, ems235 or ems96 alleles. We have designated these new loci "rmr" for required to maintain repression to reflect the necessity of rmr functions for maintaining Pl' in a mitotically- and meiotically-heritable repressed state. The ems136 and ems235 alleles together define the rmr1 locus and are designated rmr1-1 and rmr1-2 respectively. The ems96 allele defines the rmr2 locus and is designated rmr2-1.

Pl' most frequently changed to a non-paramutagenic (Pl-Rh) state in plants homozygous for either the rmr1-1 or rmr1-2 alleles (Table 8). Approx. 70% of crosses between Pl-Rh/Pl-Rh testers and plants homozygous for either the rmr1-1 or rmr1-2 allele produced at least one progeny plant having a Pl-Rh anther phenotype compared to only 22% of similar testcrosses with plants homozygous for the rmr2-1 allele. This difference may partially relate to observations showing that different Pl-Rh/Pl-Rh testers themselves have different frequencies of spontaneous paramutation; Pl-Rh can spontaneously change to Pl' in the absence of Pl' (Hollick et al. 1995). To control for such differences, Pl-Rh/Pl-Rh pollen collected from a single plant was used to pollinate rmr1-1 and rmr2-1 homozygous plants. Both sets of crosses produced at least one progeny plant with a Pl-Rh phenotype indicating that both rmr1-1 and rmr2-1 mutations can allow meiotically-heritable derepression of Pl'. However, proportionally more Pl-Rh-like progeny were derived from crosses made with homozygous rmr1-1 plants (Table 9). In addition, progeny plants had higher Anther Color Scores from the rmr1-1 crosses relative to the rmr2-1 crosses suggesting that Pl' alleles are, in general, less paramutagenic when transmitted through plants homozygous for rmr1-1 as compared to rmr2-1 (Tables 8 and 9).

Given that Pl' could sometimes change to a meiotically-heritable Pl-Rh state in either homozygous rmr1-1 and rmr2-1 plants, we asked whether such newly changed Pl' alleles, formally designated Pl('), were distinguishable from a naive Pl-Rh allele. It was possible that Pl(') might retain residual paramutagenic activity relative to Pl-Rh. A cosegregation test using linked sm1 markers was used to show that a Pl(') allele transmitted from a either a rmr1-1 or rmr2-1 homozygote was indistinguishable from naive Pl-Rh in terms of its paramutagenicity (FIG. 19). Thus, both RMR1 and RMR2 functions contribute to the meiotically heritable maintenance of the paramutagenic Pl' state. In the absence of RMR1 or RMR2 function, Pl' always has a somatic expression phenotype indistinguishable from Pl-Rh but this does not ensure that Pl' always changes to a meiotically-heritable Pl-Rh state.

TABLE 8

Pl' changes to Pl-Rh
Pl'/Pl'; ems/ems X Pl-Rh/Pl-Rh and Pl-Rh/Pl-Rh X Pl'/Pl'; ems/ems

| Allele Tested | Ears Examined | Number of Plants with Given Anther Color Score | | | | | | | Frequency of Pl-Rh types |
|---|---|---|---|---|---|---|---|---|---|
| | | 1 | 2 | 3 | 4 | 5 | 6 | 7 | |
| ems136 | 21 (15/21) | 40 | 113 | 100 | 38 | 26 | 22 | 61 | 0.15 |
| ems235 | 9 (6/9) | 4 | 33 | 46 | 26 | 8 | 13 | 17 | 0.12 |
| ems96 | 40 (9/40) | 267 | 390 | 84 | 46 | 13 | 0 | 80 | 0.09 |

Genetic crosses listed at the top of the table were used to determine whether or not Pl' alleles could change to a non-paramutagenic Pl-Rh state in plants that were homozygous for the given EMS-derived alleles. The total number of ears sampled is given along with the fraction of ears that gave rise to plants with fully-colored anthers. The total numbers of progeny with a given Anther Color Score are listed along with the frequency of progeny having a Pl-Rh phenotype (ACS 7).

TABLE 9

Pl' changes to Pl-Rh using a single pollen source
Pl'/Pl'; rmr/rmr X Pl-Rh/Pl-Rh

| Allele Tested | Ears Examined | Number of Plants with Given Anther Color Score | | | | | | | Frequency of Pl-Rh Types |
|---|---|---|---|---|---|---|---|---|---|
| | | 1 | 2 | 3 | 4 | 5 | 6 | 7 | |
| rmr1-1 | 4 (2/4) | 4 | 21 | 10 | 24 | 7 | 0 | 9 | 0.12 |
| rmr2-1 | 4 (1/4) | 24 | 20 | 5 | 5 | 2 | 0 | 1 | 0.02 |

Figure 20:
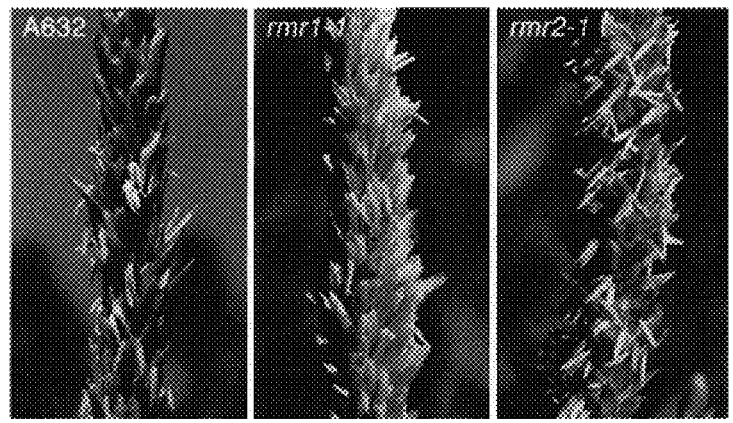
FIG. 20 shows anther phenotypes of plants that are homozygous for the pI-A632 allele. Photographs are of tassels from an A632 plant (left), a plant that is homozygous for the rmr1-1 allele (center), and a plant that is homozygous for the rmr2-1 allele (right).

The Pl' state can change to Pl-Rh in plants homozygous for mutations in rmr loci. Genetic crosses using a shared source of Pl-Rh/Pl-Rh pollen were made as indicated at the top of the table with female parents homozygous for the given rmr alleles. The total number of ears sampled is given along with the fraction of ears that gave rise to plants with fully-colored anthers. The total numbers of progeny with a given Anther Color Score are listed along with the frequency of progeny with a Pl-Rh phenotype (ACS 7).

rmr Mutations do not Affect the Expression of Other pl1 Alleles. We addressed the possibility that rmr functions generally affect all pl1 alleles by combining neutral pl1 alleles with either the rmr1-1 or rmr2-1 alleles and examining the anther phenotypes. The neutral pl-A632 and pl-W22 alleles confer weak, sunlight-dependent, pigmentation to the anthers. Anthers of plants homozygous for the pl-A632 or pl-W22 alleles had visibly identical levels of pigmentation regardless of whether or not the plants were homozygous for a rmr mutation (FIG. 20) implying that RMR1 and RMR2 functions specifically affect the expression of paramutant Pl' alleles.

Heritable Changes Of Pl' to Pl-Rh In rmr1 Mutants Are Unaffected By Mode Of Sexual Transmission. Given that male and female gametes are often differentially imprinted in plants (Kermicle and Alleman 1980; Vielle-Calzada et al. 2000) and they arise at different times and locations during development, we wondered whether meiotically-heritable changes of Pl' to Pl-Rh occurred with equal frequencies in the two separate somatic cell lineages or whether there were gametophyte-specific effects. This possibility was addressed using reciprocal crosses between Pl-Rh/Pl-Rh testers and plants homozygous for the rmr1-1 allele. Pollen from Pl-Rh/Pl-Rh testers was placed on receptive silks of Pl'/Pl'; rmr1-1/rmr1-1 plants and vice versa. Plants derived from seven reciprocal crosses were grown to maturity and the Anther Color Scores determined (Table 10). When all the data are combined, the same frequency of Pl-Rh progeny was observed when Pl' was transmitted through either female or male gametes. When each reciprocal cross was examined, three sets of families had very similar frequencies. Frequencies for the remaining four sets of families varied 1.5 to two fold but there was no sex-specific trend. The frequencies of Pl' to Pl-Rh changes observed between individual rmr1-1/rmr1-1 plants could vary as much as six fold but the frequencies observed within each pair of reciprocal crosses varied no more than two fold. Thus, the frequency of heritable Pl' to Pl-Rh changes in rmr1-1 homozygotes appears to be intrinsic to each individual sporophyte and is not differentially affected by female versus male gametophyte development.

TABLE 10

Transmission of Pl-Rh from rmr1-1 plants

| Reciprocal Parent Crosses | Number of Progeny Plants with Given Anther Color Scores | | | | | | | Frequency of Pl-Rh Types |
|---|---|---|---|---|---|---|---|---|
| | 1 | 2 | 3 | 4 | 5 | 6 | 7 | |
| 98-720-10 × 98-649-1 | 0 | 5 | 3 | 3 | 2 | 0 | 4 | 0.24 |
| 98-649-1 × 98-720-10 | 1 | 1 | 2 | 4 | 1 | 2 | 6 | 0.35 |
| 98-720-19 × 98-645-1 | 0 | 2 | 9 | 2 | 3 | 1 | 3 | 0.15 |
| 98-645-1 × 98-720-19 | 0 | 1 | 2 | 5 | 5 | 1 | 6 | 0.3 |
| 98-720-22 × 98-648-3 | 0 | 0 | 1 | 2 | 2 | 2 | 14 | 0.67 |
| 98-648-3 × 98-720-22 | 0 | 2 | 1 | 0 | 3 | 1 | 12 | 0.63 |
| 98-721-4 × 98-648-1 | 0 | 3 | 2 | 4 | 0 | 0 | 9 | 0.5 |
| 98-648-1 × 98-721-4 | 0 | 2 | 0 | 6 | 3 | 2 | 6 | 0.32 |
| 98-721-12 × 98-646-4 | 0 | 0 | 3 | 0 | 1 | 1 | 13 | 0.72 |
| 98-646-4 × 98-721-12 | 0 | 0 | 0 | 1 | 2 | 1 | 11 | 0.73 |
| 98-721-17 × 98-645-2 | 0 | 2 | 4 | 2 | 0 | 5 | 9 | 0.41 |
| 98-645-2 × 98-721-17 | 0 | 0 | 0 | 1 | 2 | 1 | 18 | 0.82 |
| 98-721-18 × 98-648-4 | 0 | 1 | 0 | 1 | 0 | 0 | 17 | 0.89 |
| 98-648-4 × 98-721-18 | 0 | 0 | 0 | 1 | 2 | 0 | 9 | 0.75 |
| Total for rmr1-1 females | 0 | 13 | 22 | 18 | 8 | 9 | 87 | 0.55 |
| Total for rmr1-1 males | 1 | 6 | 5 | 18 | 20 | 10 | 82 | 0.58 | rmr1 and rmr2 Mutants Do Not Appear To Affect Plant Development. Although mutations in Mop1 can lead to a wide range of developmentally abnormal phenotypes (Example 1) we have not observed grossly abnormal phenotypes in homozygous rmr1 and rmr2 mutant plants. We began this series of observations by first generating F1 individuals between A632 inbred plants and plants homozygous for either rmr1-1, rmr1-2 or rmr2-1 and then examining the F2 homozygous mutants derived from self pollination. This strategy was adopted to reduce the number of other unlinked EMS-induced mutations that might potentially affect plant morphology. Of the 200 rmr F2 plants segregating for each rmr mutation, all plants that had a fully-colored anther phenotype were otherwise similar in stature, morphology, and flowering time to sibling plants. F2 families generated using the rmr mutations and both the A619 and W22 inbred lines gave identical results.

Figure 32A:
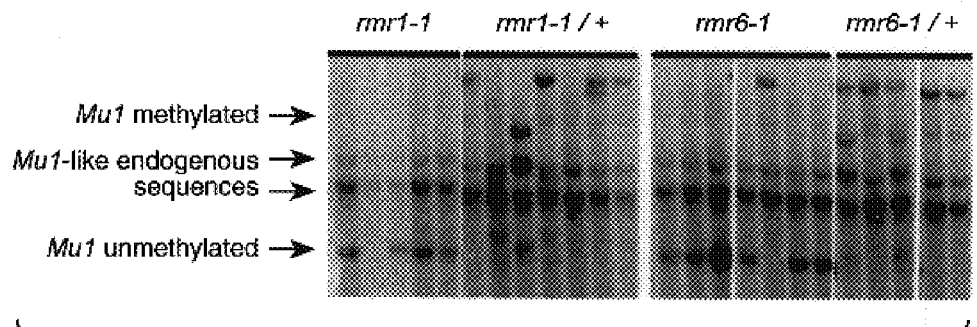
FIGS. 32A–B show methylation gel blot analyses of Mu1 sequences for (A) rmr1, rmr6, and (B) rmr2 mutants.
Figure 32B:
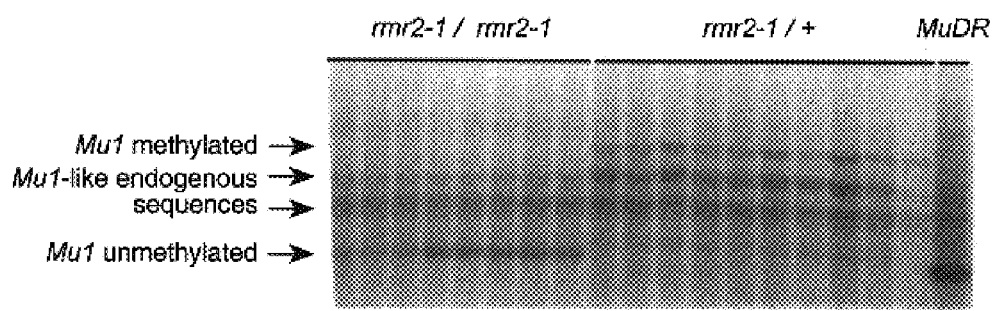
Figures 33A, 33B:
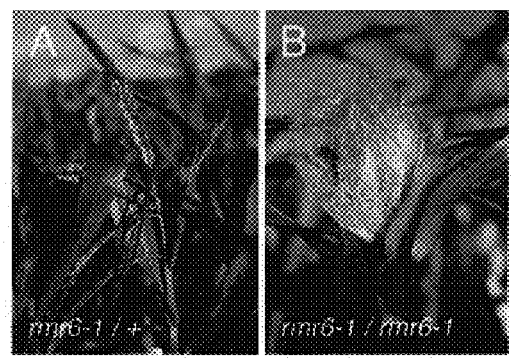
FIGS. 33A–B show comparison of (A) rmr6-1/Rmr6 (indicated as rmr6-1/+) and (B) rmr6-1/rmr6-1 mature tassel phenotypes.

Further generations of inbreeding did not produce abnormal plants. Several rmr F2 plants (A632 background) with fully-colored anthers that had a Pl-Rh/Pl-Rh RFLP genotype were self pollinated and also outcrossed to Pl-Rh/Pl-Rh testers. All F3 plants from the self pollinations had fully-colored anthers but were otherwise similar in all other respects to testcross progeny. F4 plants derived by self pollination of homozygous rmr1-1 F3 plants were also normal in appearance and similar in all respects to the previous F3 plants. A single F3 plant homozygous for rmr2-1 was crossed to a rmr2-1 heterozygote from a separate lineage to generate a family where rmr2-1 homozygotes and heterozygotes could be compared. Aside from differences in anther pigmentation, rmr2-1 homozygotes were indistinguishable from their heterozygous siblings. Although it remains possible that prolonged exposure of the genome to defects in RMR1 and RMR2 functions could have pleiotropic consequences, we currently have no indications that they are required for proper plant development, at least in the A632, A619, or W22 backgrounds.

rmr1 and rmr2 Mutations Prevent Mu Element Methylation. Given the observation that Mop1 affects both paramutation and Mu methylation (Example 2), we were curious to see if the rmr mutations did the same. Because the background in which the rmr mutations was isolated lacked full length MuDR elements (data not shown), it was possible to directly observe the effect of these mutations on endogenous Mu1 elements in the absence of the transposase. DNA from three families that were segregating 1:1 for homozygous mutant and heterozygous siblings was analyzed for the methylation status of Mu1 sequences (see Example 2 for details). Four of four rmr1-1/rmr1-1 plants had unmethylated Mu1 sequences while four of seven rmr1-1+ plants had clearly methylated Mu1 sequences (FIG. 32A). The other three rmr1-1+ plants did not have methylated Mu1 sequences (FIG. 32A). The correlation between Mu1 methylation and rmr2-1 genotypes was perfect; eight of eight rmr2-1/rmr2-1 plants had no detectable Mu1 methylation and 10/10 rmr2-11+ plants had heavily methylated Mu1 sequences (FIG. 32B). These results strongly suggest that Mu element hypomethylation is a generic effect of mutations affecting paramutation rather than a specific effect of Mop1.

Summary. Using a seedling-based genetic screen, we identified three maize loci (Mop1, rmr1 and rmr2) whose trans-acting functions are required to maintain gene silencing that occurs as the result of paramutation at the pl1 locus. In all plants homozygous for mutations in Mop1, rmr1, or rmr2, Pl' is expressed at a high level indistinguishable from Pl-Rh (Example 1). While the reduced expression state (Pl') is most frequently restored upon outcrossing to non-mutant plants, an increased expression state indistinguishable from Pl-Rh can be meiotically heritable. Because pl1 paramutation is associated with changes in pl1 transcription, our working model is that RMR1, RMR2, and MOP1 functions are involved with the maintenance of specific chromatin structures that prohibit high levels of pl1 transcription.

Additional rmr loci are clearly involved in Pl' repression. Our reported genetic screen represents only 10% theoretical saturation. This estimate is based on the apparent mutation rate of one detectable hit per gene per 1000 genomes screened and the roughly 95% probability that 5000 screened genomes would yield at least one detectable mutation in every given gene. These numbers suggest that six to ten such rmr-like loci exist in maize. Indeed, five additional rmr loci have already been identified in ongoing genetic screens (see Example 6, J. Hollick, unpublished).

Paramutation silencing at the pl1 locus not only leads to repression of Pl-Rh expression, it also affects the way in which the Pl-Rh allele is regulated (Hollick et al. 2000). Pl-Rh expression is light-insensitive while Pl' expression is light-dependent. As most pl1 alleles are regulated by light cues, the observations that rmr1 and rmr2 mutations have no effect on pl-A632 or pl-W22 suggests that RMR functions do not mediate light-induction. Rather, we hypothesize that RMR functions are used in maintaining a specific regulatory state unique to Pl'. The Pl-Rh state then must actively prevent or avoid RMR action. Two general and non-exclusive modes of action are considered: 1) rmr RNA or proteins are components of a heritable chromatin structure that affects pl1 transcription, 2) RMR functions facilitate alterations or maintenance of a heritable chromatin structure. Previous work has shown that paramutant pl1 and r1 alleles require continued allelic interactions with another paramutant or paramutagenic partner (Styles and Brink 1968; Hollick and Chandler 1998). It is possible that RMR functions actually mediate these allelic interactions through homology searching or specifying intranuclear positions.

It is not known whether the rmr mutations described represent complete loss-of-function alleles. In fact, the observation that pl1 RNA levels are significantly lower in homozygous rmr1-2 plants versus rmr1-1 plants hints that the two alleles have different levels of activity. Nonetheless, mutations at both the rmr1 and rmr2 loci are completely recessive suggesting that neither RMR1 or RMR2 functions are dosage sensitive as are many of the genes required to mediate examples of position effect variegation seen in *Drosophila* (reviewed in Weiler and Wakimoto 1995).

Despite similar effects on pI1 RNA levels, the frequency of meiotically-heritable PI' to PI-Rh changes is clearly different in the rmr1 mutants versus rmr2-1 mutants. Even in rmr1-2 homozygotes where the relative level of pI1 RNA is lower than in rmr2-1 homozygotes, PI' changes to a PI-Rh state more frequently in homozygous rmr1-2 plants. This set of results implies that derepression of PI' in somatic tissues is, by itself, insufficient to allow a meiotically-heritable change of PI' to PI-Rh. In addition to PI' heritably changing to PI-Rh more frequently in rmr1 mutant plants, those alleles that remain PI' upon transmission appear to be less paramutagenic than those transmitted from rmr2-1 mutant plants. One interpretation is that RMR1 and RMR2 functions are distinct in terms of their role(s) in maintaining meiotically-heritable repression of PI'. This idea is supported by the finding that rmr1-1 leads to loss of a post-transcriptional regulatory step while rmr2-1 leads to loss of a transcriptional-based mechanism.

Although PI' heritably changes to PI-Rh at different frequencies between individual rmr1-1/rmr1-1 plants, similar frequencies were observed independent of female versus male transmission in several reciprocal crosses (Table 10). In these families, the frequency of meiotically heritable changes of PI' to PI-Rh was established early in development prior to the point that cell lineages diverged to specify the lateral versus apical infloresence meristems. Frequencies of heritable PI' to PI-Rh changes were distinct, however, between each set of reciprocal crosses. This observation implies that different frequencies can be established and maintained through most of sporophyte development with relatively high fidelity. It remains unclear as to whether PI' actually changes to a meiotically-heritable PI-Rh state during early development or whether the probability of such changes later in development are preset early on.

RMR1 and RMR2 functions do not appear to be involved in general gene control mechanisms required for development. To date, plants homozygous for the rmr1-1, rmr1-2 or rmr2-1 alleles have been morphologically and developmentally indistinguishable from their heterozygous siblings. This absence of morphological defects, even after three generations of selfing, suggests that rmr1 and rmr2 are unlikely to be maize orthologues of the *Arabidopsis* ddm1 or met1 genes. Mutations of ddm1, a SWI2/SNF-2-like gene (Jeddeloh et al. 1999), and dominant-inhibitors of met1, a DNA methyl transferase enzyme, have broad and cumulative effects on *Arabidopsis* development (Kakutani et al. 1996; Ronemus et al. 1996; Finnegan et al. 1996). Because mutations in Mop1 also appear to have effects on plant development (Example 1), it appears that the rmr1 and rmr2 loci define a class of genetic functions distinct from MOP1. Alternatively, RMR1 and RMR2 may participate in developmental pathways similar to MOP1 but have redundant developmental functions. Double mutant combinations are currently being synthesized to test this possibility.

Several other genes required to maintain transgene silencing in *Arabidopsis* have been recently described. Some of these genes like sgs1, sgs2, sgs3 (suppressor of gene silencing) and sde1, sde2, sde3, and sde4 (silencing defective) are required for post-transcriptional silencing (Elmayan et al. 1998; Mourrain et al. 2000; Dalmay et al. 2000) while others, hog1 (homology-dependent gene silencing 1), sil1, sil2 (silencing), and mom1 (Morpheus' molecule 1) are required for transcriptional-based silencing (Furner et al. 1998; Amedeo et al. 2000). Given that paramutation at the b1 and pI1 loci affect heritable states of transcriptional control (Patterson et al 1993; Hollick et al. 2000), the rmr genes could potentially be related to this latter class of *Arabidopsis* genes. Paramutation has not been described in *Arabidopsis*.

Example 4

Isolation of a Dominant Mutation, Mop2-1, and Two Recessive Mutations, mop3-1 and CC2343, Using the B' Screen 1. Materials and Methods.

Plant Stocks. All plant stocks contained dominant functional alleles for all the genes encoding the anthocyanin biosynthetic enzymes required in vegetative plant tissues. Because transcription of these genes in vegetative plant tissues is controlled by pI1 in combination with b1 or r1, the specific b1, pI1 and r1 alleles are indicated for relevant stocks. One exception is the distinction between PI'-mahogany (PI) and PI-Rhoades (PI-Rh) (Hollick et al., 1995). Many stocks possess the R-g allele of r1 (no expression in the seed or plant), which precludes reliable scoring of PI' versus PI-Rh. In these stocks, we have used P/ to indicate the presence of either PI-Rh, or its spontaneous derivative PI'.

A gl2 b wt, PI, R-g (inbred K55 background) stock, as well as B-I PIR-g (inbred W23 background) and B' PIR-g (inbred K55 background) stock were originally obtained from E. H. Coe, Jr. (University of Missouri, Columbia). These stocks were used by V. L. Chandler to generate gl2 B' wt and gl2 B-I wt stocks. To test whether Mop2-1 affects pI1 paramutation, our Mop2-1 stocks were crossed with stocks containing the R-r allele to facilitate reliable scoring of the pI1 genotype. These included a gl2 b wt, PI-Rh, R-r stock generated by V. L. Chandler, and a y1 PI' sm, PRR stock originally obtained from the Maize Cooperation Stock center.

Genetic Screen. A screening population was generated by treating B', PI-Rh, R-g (inbred K55 background) pollen with ethyl methanesulfonate (EMS; 0.063% as described by Neuffer and Coe, 1978), and using treated pollen to pollinate gl2 B-I wt, PI-Rh, R-g (stock generated by V. L. Chandler—mix of W23/K55 inbred stocks) ears, producing M1 seed. The gl2 and wt loci flank the b1 gene. In wild-type stocks, B' will paramutate B-I, and all progeny will be light, whereas rare plants having B-q pigmentation levels may indicate the presence of a mutation preventing the establishment of paramutation. The M1 seed was planted to screen mature plants for rare individuals having B-I pigmentation levels. Presence of the recessive gl2 and wt markers in the B-I ear parent enable rapid identification of any self-pollination contaminant offspring. This is important because self-contaminants would yield the desired rare phenotype of B-I pigment levels.

Over 7300 M1 seed was planted in the summer of 1993. One exceptional darkly-pigmented individual was identified (KK1238-1). This individual was self-pollinated, and outcrossed to several tester stocks (gl2 B-I wt, gl2 B' wt, and gl2 b wt). The results of these and subsequent crosses (detailed below) demonstrated that KK1238-1 carried a heritable dominant mutation capable of inhibiting B-I paramutation. This dominant mutation has been designated Mop2-1.

Many of the M1 plants (other than KK1238-1) that showed a B' phenotype were self-pollinated, and M2 families were screened in sand benches for the presence of rare darkly-pigmented seedlings resembling B-I-like plants among siblings that were essentially green. One family (KK1191-1X) segregated ¼ darkly-pigmented plants suggesting the presence of a recessive mutation. Dark and light individuals along with appropriate testers were transplanted. Another ~100 families were screened, but no other mutations were found. Crosses were performed with the new putative mutant to test for heritability, bulk up seed and begin complementation tests with other mutants such as those described in Example 1 and Example 3.

Molecular Markers Map position of the Mop2-1 mutation was confirmed using simple sequence repeat (SSR) molecular markers. A large number of these PCR-based markers are available for maize (agron.missouri.edu at ssr.html). The SSR markers that are tightly linked to Mop2-1 and were used to follow Mop2-1 segregation are bnlg1017, bnlg1338 and umc1823.

2. Identification and Characterization of a Dominant Mutation, Mop2-1

The facts that B' is extremely stable and that paramutation always occurs when B' and B-I are brought together in a heterozygous individual enable a simple genetic screen to identify mutations involved in paramutation. B' pollen was treated with the mutagen ethyl methanesulfonate (EMS), and used to pollinate gl2 B-I wt ears. The gl2 wt recessive marker loci, which flank the b1 gene, enable the identification and elimination of any gl2 B-I wt pollen self-contaminants, and can also be used to follow chromosome 2 segregation in subsequent generations. Over 7300 M1 seed were grown to maturity and screened for dark plants that may carry a dominant mutation that disrupts the establishment of paramutation. One exceptional dark plant was recovered.

A series of crosses were done to confirm the presence of a heritable mutation and further characterize its behavior. This exceptional dark plant was crossed to a gl2 B' wt tester plant, and all 15 B' progeny were subsequently crossed to gl2 B-I wt to determine which individuals carried the dominant mutation capable of inhibiting paramutation (FIG. 23). To determine whether this dominant mutation identifies an independent locus involved in paramutation, or a mutation in the B' allele which abolishes its paramutagenic properties, we tested for co-segregation of the mutation with the B' allele. The B' allele originating from the EMS treated pollen was flanked by wild-type alleles of the gl2 and wt loci (Gl2 and Wt), whereas the B-I allele carried the recessive gl2 wt markers. These markers were used to separate progeny of the above cross with gl2 B' wt into those inheriting the Gl/2 B' Wt chromosome, and those inheriting the gl2 B-I wt chromosome (FIG. 23). One individual was recombinant in the gl2 wt interval and was therefore not informative with respect to which b1 allele had been inherited, though the presence of dark progeny in a testcross with gl2 B-I wt demonstrates that it inherited the mutation. Of six individuals inheriting the Gl2 B' Wt chromosome, all six gave rise to dark progeny when crossed to gl2 B-I wt consistent with each of them carrying the dominant mutation. If the mutation were unlinked to b1, we would expect that only half of these individuals would inherit the dominant mutation and give dark progeny in the next generation. The likelihood that all six individuals would inherit an unlinked mutation by chance is small (p=0.016), therefore it is most likely that the mutation is linked to b1.

To further determine whether this linked mutation is disrupted in the B' allele or in a linked but independent locus, the progeny of these six individuals were further examined. Given the fact that a double recombination event separating the B' allele from its flanking Gl2 and Wt markers would be quite rare, if the mutation is at B' we would expect that all Gl2 Wt progeny would be dark and all gl2 wt progeny should be light. This expectation was not met. Eleven percent of the gl2 wt progeny were dark, and 12.5% of the Gl2 Wt progeny were light. These results are most consistent with the mutation residing outside the gl2 wt interval and thus independent of the b1 locus. The fact that Gl2 wt recombinant progeny inherited the mutation (dark plants) and gl2 Wt recombinant progeny did not (light plants) demonstrates that the mutation lies distal to the gl2 locus.

As additional confirmation of this conclusion, nine progeny of the same original cross to gl2 B' wt (FIG. 23) inherited the gl2 B-I wt chromosome, though as described above, all nine were light (B' phenotype) confirming that the B-I allele was still paramutable. These nine individuals were testcrossed to additional gl2 B-I wt tester stocks to determine whether they carried the dominant mutation. Consistent with the mutation residing on the homologous chromosome, seven of these individuals did not carry the mutation and gave all light progeny, whereas two individuals gave dark progeny indicating they had inherited the linked mutation, but that it must reside outside the gl2 wt interval.

Thus, this mutation identifies a locus, distinct from b1, which appears to play a role in paramutation. Based upon subsequent analyses described below which reveal similarities with the recessive mediator of paramutation 1 mutations, we have designated this locus mediator of paramutation 2, and the mutation Mop2-1.

3. Penetrance of Mop2-1 vs. Spontaneous Paramutation of B-I.

Though segregation of the mutation could be followed by the presence of dark progeny, the frequency of dark progeny in some of the above crosses was less than predicted. In crosses of BVB' Mop2-1/mop2×B-I/B-I mop2/mop2, 50% of progeny should be dark because they inherit the Mop2-1 mutation, yet in some families the frequency of dark progeny was much lower (30–35%). One possible interpretation is that Mop2-1 is not fully penetrant in preventing paramutation. Another possibility is that the B-I allele of the tester plants is spontaneously paramutating to B' on a stochastic basis. Spontaneous changes of B-I to B' occur regularly in both standard and Mop2-1 stocks, and could easily account for the discrepancy (35% observed vs. 50% expected) observed in some families. Plants in which this occurs would be light even though they carry Mop2-1. Consistent with this interpretation is the fact that spontaneous paramutation of B-I to B' occurs in wild-type stocks, and often occurs more frequently in some families than others. The distribution of color scores among the progeny of 9 individuals that carried the Mop2-1 mutation are shown in FIG. 26. Color scores were used as many individuals did not fall into clear categories of light or dark, but rather had intermediate phenotypes. Color scores of 1–3 are typical of a B' individual, and 6–7 are typical of a B-I individual. Both sheaths and tassels were scored. Some families gave a clearly bimodal distribution of color scores with approximately 1:1 B-I to B' progeny (e.g. Families 4, 5, 7). Other families gave considerably more intermediate individuals (color scores of 4–5, e.g. Families 2, 6, 8).

The fact that B' Mop2-1/mop2×B-I individuals inheriting Mop2-1 can be light is also apparent in the fact that two light progeny of the original dark plant inherited recombinant gI2 B-I wt chromosomes carrying Mop2-1. These progeny were light upon outcross to gI2 B' wt, consistent with either incomplete penetrance of the mutation or spontaneous paramutation of the B-I allele, but the presence of Mop2-1 was established upon outcrossing each individual to gI2 B-I wt and observing dark progeny.

Mop2-1 also prevents the establishment of pI1 paramutation To determine whether mop2 can affect additional paramutable loci in trans or is restricted to the linked b1 locus, we tested whether it could inhibit the establishment of pI1 paramutation. We crossed an individual heterozygous for the Mop2-1 mutation with a stock homozygous for the PI-Rh and R-r alleles. All progeny from this cross had fully-pigmented anthers (PI-Rh) which enabled us to confirm that the PI-Rh allele in the Mop2-1 plant had not spontaneously changed to PI'. Progeny of this cross, half of which should carry the Mop2-1 mutation, were crossed with a paramutagenic PI' stock. Two of these individuals gave progeny segregating 1:1 for dark (PI-Rh) and light (PI') anthered plants suggesting they carried the Mop2-1 mutation, whereas a third individual gave all PI' progeny consistent with the parent individual lacking the Mop2-1 mutation. The presence of dark-anthered progeny demonstrates that the Mop2-1 mutation is able to inhibit the establishment of pI1 paramutation. The 1:1 segregation ratio (total for both families 17:18) observed among the progeny further suggests that the Mop2-1 mutation is fully penetrant with respect to the inhibition of pI1 paramutation. This observation, together with the fact that some crosses with B-I yield 1:1 segregation ratios, suggests that the Mop2-1 mutation is fully penetrant and that instances in which less than 50% darks are observed are more easily explained by spontaneous paramutation of B-I to B'. These results are also consistent with observations that B-I is less stable than PI-Rh, i.e. more likely to undergo spontaneous paramutation.

Phenotype of homozygous Mop2-1. To determine whether this mutation represents a true dominant or a semi-dominant allele, we have generated homozygous mutant individuals. Though the original exceptional dark individual in the M1 screening population had been self-pollinated in an effort to generate individuals homozygous for the mutation, nearly all progeny of this self-pollination were unhealthy or failed to thrive such that testcrosses for the identification of homozygous individuals were difficult to obtain. This is presumably due to the presence of additional mutations resulting from the EMS mutagenesis that become homozygous in the M2 progeny. Instead, we took advantage of the fact that Mop2-1 heterozygous individuals resulting from the pI1 experiments described above were considerably more vigorous than previously identified Mop2-1 stocks, presumably due to hybrid vigor from multiple outcrosses to distinct genetic stocks. Several of the heterozygous Mop2-1 individuals identified by the presence of dark red anthers were self-pollinated. Progeny (B') were self-pollinated and testcrossed to B-I to determine their mop2 genotype. All 13 testcross progeny of one individual possessed the B-I phenotype, indicating that the parent had been homozygous for the Mop2-1 mutation. Progeny from the self-pollination of this individual were grown in our winter nursery in Hawaii. Progeny from the self-pollinations of two sibling individuals shown to be heterozygous for the Mop2-1 mutation were also grown as a control.

Figure 25A:
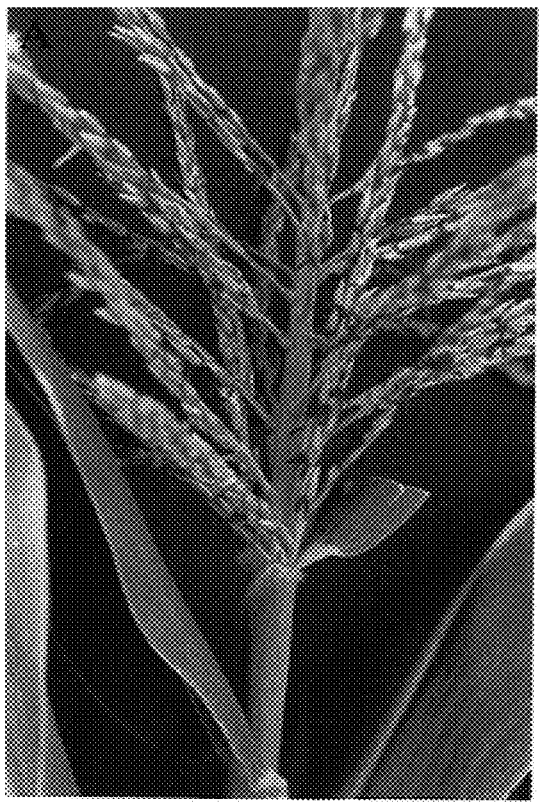
FIG. 25 shows the phenotypes associated with homozygous Mop2-1 individuals and heterozygous siblings. A) Heterozygous Mop2-1 individual showing normal B' pigmentation. B) Homozygous Mop2-1 individual showing intensification of pigment and tassel seed phenotype.
Figure 25B:

Plants of these self-pollinations were initially scored about 2 weeks prior to anthesis. No obvious phenotypic differences were noted at that time, though the progeny of the homozygous individual were somewhat less vigorous than most progeny of the heterozygous individuals. As the progeny of the homozygous Mop2-1 individual approached anthesis, they darkened. Progeny from the self-pollinations of two heterozygous Mop2-1 individuals showed two phenotypic classes: several individuals were lightly pigmented and quite vigorous, some of which were already flowering; whereas a few individuals were spindly, much later flowering, and somewhat darker than their sibs. Furthermore, some additional individuals were less than half the height of their sibs, quite spindly, and showed no hope of producing an ear. Among the slightly darker progeny of the heterozygous individuals, and the progeny of the homozygous individual, were some individuals showing a tassel-seed phenotype. Over the next week or two, some of these individuals continued to darken such that some approached a B-I-like phenotype (FIG. 25). Analysis of a linked simple sequence repeat (SSR) locus, and testcrosses for a majority of individuals in these families confirmed that the darker individuals were homozygous for the Mop2-1 mutation whereas the lighter sibs were heterozygous or homozygous for the wild-type allele. This difference in pigmentation correlates with increased b1 transcript levels in the homozygous Mop2-1 individuals relative to their heterozygous siblings (FIG. 26A).

To determine whether the darker phenotype of the homozygous Mop2-1 individuals would result in a heritable alteration of the B' allele, some of the darker homozygous individuals were also crossed to a B-Peru tester. B-Peru gives purple kernel color but extremely weak plant color such that B' or B-I plant pigment is readily apparent. All progeny of this cross had typical B' pigment levels, suggesting that the effect of homozygous Mop2-1 had not produced a heritable alteration of B'.

Mop2-1 Summary. Mop2-1 represents a novel dominant mutation able to inhibit the establishment of paramutation at b1 and pI1. In this sense, Mop2-1 is distinct from Mop1, mop3, rmr1 and rmr2. Plants homozygous for this mutation also show recessive phenotypes such as increased pigment and b1 transcript levels, and developmental abnormalities. These recessive pigment phenotypes are similar to those observed for mutations in Mop1, mop3, rmr1 and rmr2, and the developmental abnormalities similar to mutations in Mop1, mop3 and CC2343.

4. Isolation and Characterization of Recessive Mutations, mop3-1 and CC2343

Two new recessive mutants were isolated in seedling and mature plant screens using B'. Examples of the phenotypes are shown in FIG. 27. Both of these mutations appear to represent unique genes, which increase the RNA levels of B' and mop3-1 decreases the methylation of Mu1 elements. These results indicate that the two genes identified by these mutations are required for maintenance of paramutation at B' and mop3-1 and for maintenance of the hypermethylation of Mu1 elements.

Isolation of mop3-1 All but one of the M1 plants from the screen described for the isolation of Mop2-1 had a wild-type B' phenotype, yet they could carry new recessive mutations. These M1 plants (other than the plant carrying the Mop2-1 mutation) were self-pollinated to generate M2 families. M2 families were screened in sand benches for the presence of rare darkly-pigmented seedlings resembling B-I-like plants among siblings that were essentially green. One family (KK1191-1X) segregated ¼ darkly pigmented plants (example of phenotype in FIG. 27A) suggesting the presence of a recessive mutation.

The KK1191-1 family showed good penetrance of the mutant phenotype, and additional genetic tests of this mutation were performed. To bulk up the family, a plant homozygous for this mutant and homozygous for B' was crossed to a plant that was homozygous for B-1. Ninety of the resulting seed were planted. Approximately 75 plants germinated; all of them had the B' phenotype, consistent with the new mutation being recessive and that the B' state was not heritably changed to B-I in the homozygous mutant. Several of these plants were crossed to siblings to test for heritability. In one family of 15 plants, four showed the mutant phenotype, consistent with the segregation of a single recessive mutation.

Isolation of CC2343. The CC2343 mutation was isolated using a different screen as compared to that which led to the identification of the other mutations. Pollen from B' plants was treated with EMS and used to pollinate B' ears. A total of 1464 M1 seed were planted and screened for dark plants, which could represent a dominant mutation that relieved the silencing associated with the paramutant B' state. One dark plant was observed and designated CC2343. The mutant plant made no fertile ear, so it could only be crossed as male onto testers. The only cross that produced seed was to DS1630 (b R-g Pl). Thirty-four seed were obtained and planted in the spring of 2000, only 22 germinated. One of the 22 plants was dark at its base with a B' phenotype in its tassel (N182–16), while the rest of the plants had the B' phenotype. If the original dark plant had carried a dominant mutation that increased the expression of B', the expectation is that ½ the plants should have been dark. This expectation was clearly not met. Three possibilities were considered: first, the original plant did not represent a new mutation; second there was a low penetrance due to background or environmental effects; third, the original dark plant contained two unlinked mutations and both needed to be present as heterozygotes for the phenotype to be observed. A prediction of the third hypothesis is that ¼ of the plants should have been dark because they received both unlinked mutations. This was not observed. However, approximately one-third of the seeds did not germinate (12/34), which could skew the segregation ratios. Further experiments described below demonstrate that at least one new recessive mutation is segregating in these plants.

Figure 27A:
FIGS. 27A–F show phenotypes associated with the mop3-1 (A,B) and CC2343 (C–F) mutants.
Figure 27B:
Figure 27C:

To determine if recessive mutations were present in the plants, each plant was self-pollinated and progeny planted and scored for light versus dark phenotypes. Six self-pollinated plants yielded seed, which were planted in Fall 2000. If half of the original N182 plants had carried a recessive mutation, then the expectation is that half of these six families (N268, N271, N273, N275, N276, O136) would segregate dark plants in the next generation. One family (N268) segregated only green and light (B') plants. Five of the six familes (N271, N273, N275, N276, O136) each produced dark (9), medium dark (9) and lightly pigmented (16) plants, as well as green plants (17; b/b genotype). FIGS. 27C,D illustrates these phenotypes. The medium dark plants were healthy, but the very dark plants were most often short and sickly. Only one made an ear, and most had small tassels that shed poorly. The frequency of N182 plants that gave rise to mutant progeny is more consistent with the hypothesis that two independent mutations were segregating (expected frequency 0.75), rather than the hypothesis of a single mutation present in the original isolate (0.5). However, the fact that only 6/22 plants could be tested precludes a definitive conclusion.

Figure 27D:

Subsequent crosses have confirmed the presence of at least one mutation that increases B' pigment, but the poor germination and health of these plants has made it impossible to definitively conclude whether one or two mutations are segregating in these lines based simply on segregation ratios. The medium dark plants were self-pollinated, and the medium dark and dark plants were crossed to their B' siblings and outcrossed to B' testers. If the dark and medium dark plants were homozygous for a recessive mutation, then the outcrosses to B' testers should produce progeny uniformly CC2343/+B'/−. Four families that resulted from dark plants crossed to B' were planted and scored; all forty-two had the B' phenotype, consistent with a recessive mutation, not a semi-dominant mutation, in the dark plants. In the next season both the medium dark (dark sheaths and husks, but lighter, more B'-like tassel pigment; FIG. 27D) and dark plants (dark pigment in sheaths, husks and tassel; FIG. 27C) were crossed with B' CC2343/+. When possible they were also self-pollinated. In Fall 2001, the number of dark, medium dark and light plants were scored. Unfortunately, germination was very poor, such that statistically significant numbers of plants were not available for scoring in most families. Some families resulting from self-pollination of medium dark and dark plants produced all medium dark or dark plants, consistent with both phenotypic classes being homozygous for a mutation. However, some families resulting from dark or medium dark crosses with CC2343/+ produced only light plants. This could mean that there are indeed two different recessive mutations segregating in these lines, and additional experiments are underway to further explore this idea.

Complementation Tests for mop3-1 and CC2343. Complementation tests are in progress between mop3-1 and CC2343 and all of the other mutants isolated to date (Examples 1, 3, 6). The data from the initial set of experiments is summarized in Table 11. All of these crosses were between homozygous mop3-1 B' plants and heterozyotes for each of the other mutations. Thus, if mop3-1 is a mutation in the same gene as the mutation being tested, the expectation is 50% dark plants and 50% light plants when scoring for effects on B', and 50% ACS scores 1–4 and 50% ACS scores 5–7 when scoring for effects on Pl'. The mop3-1 mutation clearly defines a distinct gene from Mop1, rmr2, rmr8 and rmr9 as all the progeny are B' with low ACS. Crosses of mop3-1 with rmr11-1 mutants showed dark plants; at least 1 dark plant was observed in ¾ of the families, but the numbers were significantly lower than that expected for noncomplementation. We hypothesize that mop3-1 can interact with rmr11-1, as has been observed with other mutants (see Example 6). Crosses between rmr1-1 and mop3-1 produced a few dark anthered plants, but no increase in B' pigment. The low number of these individuals is not consistent with noncomplementation.

TABLE 11

Complementation Data for mop3-1 and CC2343

| Plant Phenotype | | # Ears Scored | Anther Color Scores* | | | | | | |
|---|---|---|---|---|---|---|---|---|---|
| B' | Dark | | 1 | 2 | 3 | 4 | 5 | 6 | 7 |
| mop3-1 | | | | | | | | | |
| rmr1-1 | 23 | | 5 | 2 | 6 | 4 | 3 | 1 | 1 | 2 |
| Mop1-1 | 48 | | 3 | Y | | | | | | |
| rmr2-1 | 27 | | 3 | 9 | 10 | 5 | 1 | 1 | | |
| rmr9-1 | 16 | | 2 | 6 | 3 | 3 | 1 | | | |
| rmr11-1 | 41 | 8 | 4 | 20 | 13 | 1 | | 1 | 2 | 2 |
| rmr8-1 | 46 | | 4 | 4 | 20 | 9 | 3 | 1 | | |

TABLE 11-continued

Complementation Data for mop3-1 and CC2343

| Plant Phenotype | | # Ears | Anther Color Scores* | | | | | | |
|---|---|---|---|---|---|---|---|---|---|
| B' | Dark | Scored | 1 | 2 | 3 | 4 | 5 | 6 | 7 |
| CC2343 | | | | | | | | | |
| rmr1-1 | 71 | 4 | 4 | 15 | 12 | 10 | 11 | 9 | 2 |
| Mop1-1 | 76 | 35 | 6 | Y | | | | | |
| rmr2-1 | 24 | | 1 | 7 | 13 | 4 | | | |
| rmr11-1 | 9 | 1 | 2 | 3 | 1 | 1 | | 1 | |

*Not all plants could be scored for anther color because in almost all families some of the tassels were destroyed prior to scoring. Therefore, more plants were scored for plant body phenotype than for ACS score.

Families noted as Y in the anther color score 1 column were R-g (yellow) and therefore it was not possible to score anther color.

The complementation tests with the CC2343 mutation suggest that CC2343 is in a gene distinct from rmr2. The experiments with the other mutations are less clear as the segregation ratios do not fit either the complementation or noncomplementation hypotheses. The simplest explanation is that CC2343 may interact with Mop1-1, rmr1-1 and rmr11-1, but further experiments will be necessary to test this hypothesis.

Mu1 Methylation Tests with mop3-1. Sibling plants segregating mop3-1 were analyzed for the methylation status of Mu1 elements, as described in detail for Mop1-1 in Example 2. DNA was extracted from light (heterozygous or homozygous wild type) and dark (homozygous for the mutation) plants, digested with HinfI and probed with Mu1. As in the case with Mop1-1 (Example 2), Mu1 elements in the mutant plants were hypomethylated relative to Mu1 elements in their wild type siblings (equivalent data was obtained as that shown in FIG. 15 for Mop1-1).

Figure 27E:
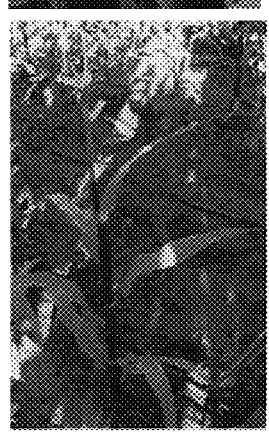
Figure 27F:
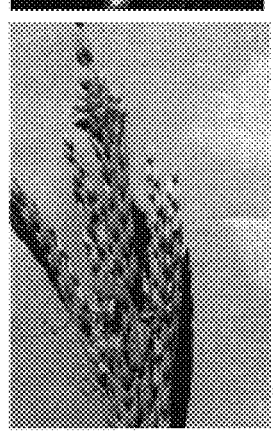

The mop3-1 and CC2343 mutations share several features with Mop1-1. Similar to Mop1-1, the dark pigment phenotype of homozygous mop3-1 and CC2343 individuals is the result of increased b1 transcript levels (FIG. 26B). Also similar to Mop1-1, mop3-1 and CC2343 occasionally show developmental effects when homozygous. Families generated from the self-fertilization of mop3-1 or CC2343 homozygotes were screened for the appearance of new phenotypes. Many of the plants showed severe developmental aberrations, including small or missing ears, runty tassels and often strongly feminized tassel structures (FIGS. 27E, F).

The plants were also very small. With mop3-1, these phenotypes occurred in essentially every plant that has been homozygous for multiple generations, but were less frequent in plants heterozygous for the mutation in the previous generation. Although fewer generations have been examined with mop3-1 and CC2343 relative to Mop1-1, the developmental defects in mop3-1 and CC2343 appear more frequently and are more severe.

Summary of mop3-1 and CC2343 Results. The complementation tests completed to date suggest that the mop3-1 and CC2343 mutations represent unique genes. Both mop3-1 and CC2343 are required to maintain the reduced expression state associated with B' paramutation. Similar to mop1 mutations, mop3-1 and CC2343 do not heritably alter the reduced expression state as B' segregates in subsequent generations in the absence of the mutation. Also similar to Mop1-1, homozygous mop3-1 and CC2343 individuals show increased b1 transcript levels and developmental abnormalities. The mop3-1 mutation is also required to retain the extensive methylation associated with silenced Mutator elements. Experiments to examine the effects of CC2343 on Mu1 methylation are in progress.

Example 5

Four Mutations Defective in Paramutation Activate Previously Silent Transgenes

Overview. Genetic studies in the 1950's revealed several examples of gene regulation that are variable, unstable, but heritable. These phenomena included paramutation and the cycling of transposable element activity in maize. Numerous models were discussed, with a common theme that global chromosomal levels of control were operating (reviewed in Chandler and Vaucheret 2001). During the past twelve years extensive studies on transgene expression in plants has revealed a wide range of gene silencing phenomena (reviewed in Fagard and Vaucheret 2000). Transgene silencing can occur either at the transcriptional (TGS) or post-transcriptional level (PTGS). It can happen in cis, affecting single transgene copies or in trans, affecting unlinked sequences (including transgenes, endogenous genes or viruses) that share high sequence similarity. TGS is often associated with sequence homology and DNA methylation in the promoter regions. PTGS correlates with homology in the transcribed regions and DNA methylation in the transcribed region and the accumulation of small RNAs (21–25 nt). It is not yet clear whether these correlations are causes or consequences of gene silencing. Paramutation at b1 is more similar to TGS rather than PTGS, because the transcription rate of paramutated alleles is decreased (Patterson et al. 1993).

Figure 28:
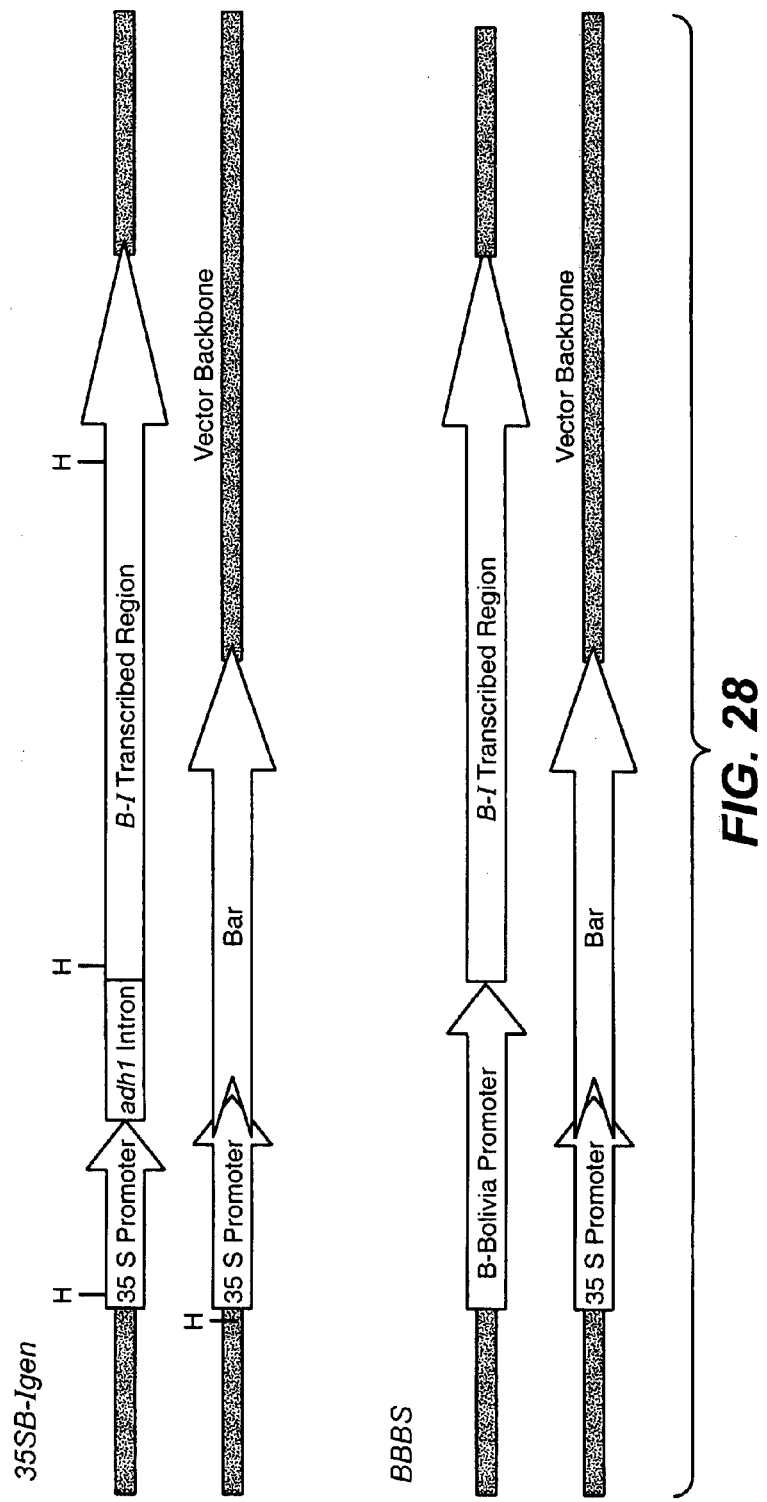
FIG. 28 shows the constructs used to generate the transgenic lines.

Given that paramutation shares some features with transgene silencing (reviewed in Chandler et al. 2000), we tested whether mutants defective in paramutation might have effects on transgene silencing. Previous work done in the Chandler lab had generated several transgenic lines, all of which contained various B transgenes that had been produced to study anthocyanin gene regulation. The B gene encodes a transcription factor that activates the biosynthetic pathway. Expression of the B gene in a particular tissue will give rise to purple pigment in that tissue. All the transgenic lines were generated by particle bombardment of immature maize embryos (C. Carey, D. Selinger and V. Chandler, unpublished data; see Selinger et al. 1999 for detailed methods). Transgenic lines that contained two different B constructs were used. In both cases the transgene was silent in vegetative and reproductive plant tissues yet it remained active in the aleurone layer of the seed. Each independent transgene segregated as a single genetic locus, but DNA blot analyses revealed multiple copies of the construct had inserted into the genome. FIG. 28 diagrams the constructs that were used to generate each of the transgenic lines. Transgenic line VLC44-27A carries a 35S promoter driving a B-I genomic construct. Expression of this transgene had never been phenotypically detectable in the plant. The BBBS transgene (VLC40-64A) carries the promoter from B-Bolivia fused to the B-I genomic region (FIG. 28; Selinger and Chandler, 2001). The original transgenic line was expressed in both the plant (leaf blade primarily) and in the aleurone layer of the seed. However, the plant pigmentation was lost in subsequent generations.

Four mutants with defects in paramutation relieve transgene silencing. For these experiments we combined each of four different mutations (Mop1-1, Mop2-1, rmr1-1 and rmr2-1) with lines containing the silent transgenes. The resulting F1 plants containing the transgene (hemizygous) were identified via PCR and DNA blots. All of these individuals were also heterozygous for a particular mutation. No activation of the transgenes was observed in this generation. These were backcrossed to plants homozygous for the particular mutation. This protocol yielded families that were segregating for the transgene and heterozygous or homozygous for the mutation being tested. For the experiments with Mop1-1, rmr-1 and Mop2-1, seeds carrying the transgene could be identified by the transgene's expression in the aleurone layer, which resulted in medium purple kernels. [It is not known why both transgenic lines were completely silent in vegetative and floral tissues, but expression was observed in the differentiated aleurone layer.] The medium purple kernels were planted and the plant and anther pigment phenotype was determined. If each of the mutations activated the transgene when homozygous, we expected ratios of 1:1 for active:inactive (presumably homozygous and heterozygous for the mutation, respectively). This expectation was met for both Mop1-1 and rmr1-1 with the two different transgenes (Table 12). Examples of the phenotype of each of the mutants and heterozygous siblings with the transgene, 35SB-/gen (VLC44–27A), are shown in FIGS. 29A–D. Examples of activation of the BBBS transgene by rmr2-1 are shown in FIG. 29E.

TABLE 12

Activation of silent transgenes

| | 35SB-Igenomic | | | BBBS | | |
|---|---|---|---|---|---|---|
| | No. Active | No. Silent | $X^2$ | No. Active | No. Silent | $X^2$ |
| Mop1-1 (1:1) | 213 | 192 | 1.1 | 27 | 26 | 0.02 |
| rmr1-1 (1:1) | 55 | 52* | 0.09 | 15 | 13 | 0.14 |
| Mop2-1 (1:1) | 16 | 32 | 5.3** | N.D. | N.D. | |
| rmr2-1 (1:3) | 26 | 95 | 0.79 | 28 | 96 | 0.39 |

Forty-four of these individuals had ACS scores between 1–4, consistent with a genotype of Rmr1/rmr1-1. Eight individuals had ACS scores of 6–7. This could be due to reversion of PI' to PI-Rh, with these individuals being Rmr1/rmr1-1 and not activating the transgene. Alternatively, the plants with ACS6–7 could have been rmr1-1 homozygotes, but the transgene was not activated. Unfortunately testcrosses of these individuals were not obtained so the rmr1 genotype could not be assessed. However, the observed segregation ratios of plants with active and inactive transgenes (in the two families where this was observed) are most consistent with the first hypothesis. **P is <0.05, significant deviation from 1:1 hypothesis; N.D.=not determined.

When active, neither of the transgenes used were ever expressed in the anthers. This enabled us to use anther color to follow the presence of heterozygous and homozygous mutants when the plants carried a-r allele and PI'. This was the case for the rmr1-1 families and for approximately ¼ of the Mop1-1 families. Crosses with Mop1-1 testers confirmed that plants that failed to activate the transgene were heterozygous for the mutation. For the experiments with rmr2-1 a dominant r1 allele was segregating, which also conferred purple aleurone pigment. Thus, planting purple kernels did not ensure that all plants would have inherited the transgene. As r1 segregated independently of the transgene and rmr2, ¼ of the plants would be expected to receive the transgene and be homozygous for rmr2-1. The numbers of plants with an active transgene were consistent with this hypothesis (Table 12). Independent of whether we could use anther color scores to assess whether the mutation was heterozygous or homozygous, every plant was crossed with appropriate mutant testers to determine or confirm the mutant genotype. Not all crosses were successful, but in all confirmed cases with Mop1-1 and rmr1-1, when the mutation was homozygous, the transgene was activated as evidenced by increased pigment in homozygous mutant plants relative to heterozygous siblings. One possible exception is indicated by the significant deviation from the expected 1:1 ratio in the Mop2-1 experiment. We have considered two possible explanations for this deviation from the expected ratios. First, it is possible that homozygous Mop2-1 individuals are not always capable of activating the transgene. It is also possible that the penetrance of the Mop2-1 phenotype in these families was low. Testcrosses are in progress to determine the genotype of plants in each class. The Mop2-1 mutation was also crossed with an independent 35SB-Igenomic transgenic line (VLC44-20). This transgene was expressed in both the plant and seed for several generations, but silenced in the generation immediately prior to crossing with Mop2-1. When this transgene was present with heterozygous Mop2-1 it was not activated, but when the F1 was crossed with a homozygous Mop2-1 plant, ⁴⁄₉ of the progeny activated the transgene (same phenotype as seen in FIG. 29A).

Figure 30:
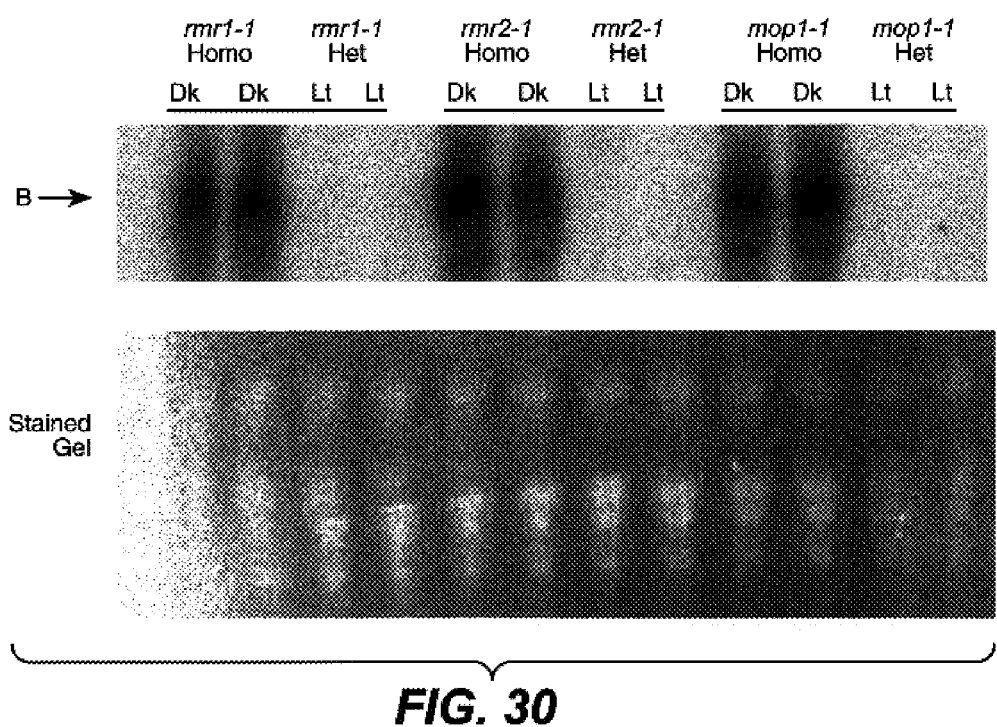
FIG. 30 shows that transgene activation by the Mop1-1, rmr1-1 and rmr2-1 mutations is associated with increased transgene transcript levels. The top panel is an RNA blot examining transgene transcript levels in individuals heterozygous for the mutation versus individuals homozygous for each of the mutations. The blot was probed with a region of the b1 gene. The bottom panel is a picture of the ethidium stained gel that was blotted, showing that similar levels of total RNA were added to each lane. See Patterson et al, 1993 for methods.

Transgene activation involves increases in the transgene RNA. Based on the effect of the mutants on B' and PI' RNA levels, we hypothesized that the increased pigment levels seen in the transgenic lines containing the homozygous mutations was due to increased levels of RNA from the transgene. To investigate this we took samples from families carrying the VLC44-27A transgene and segregating individuals heterozygous or homozygous for several mutations. RNA was prepared using the same procedure as described in Example 1, and RNA blots prepared. As shown in FIG. 30, each of the darkly pigmented plants (homozygous for either Mop1-1, rmr1-1 or rmr2-1) had dramatic increases in transgene-encoded b1 RNA.

Figure 31:
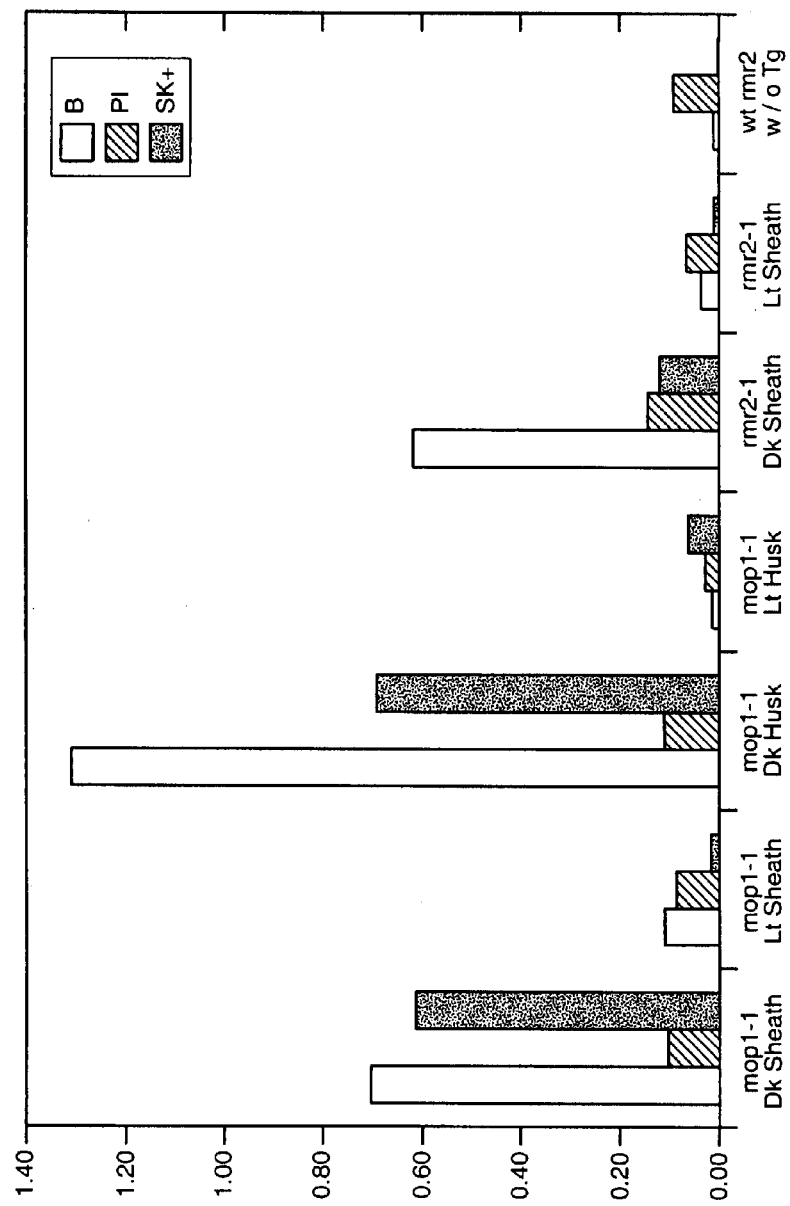
FIG. 31 summarizes data from in vitro transcription assays demonstrating that transgene activation in Mop1-1 and rmr2-1 mutants is at the transcriptional level. Methods are as described in Dorweiler et al. 2000.

The transgene is activated at the transcriptional level. To investigate whether the increased b1 RNA levels are caused by increases in transcription or increases in RNA stability we have begun to perform nuclear run-on assays (methods as described in Example 1). One set of experiments have been completed for Mop1-1 and rmr2-1 (FIG. 31). These initial results reveal that the VLC44-27A transgene (35SB-Igen) is transcribed at a low level in plants heterozygous for either Mop1-1 or rmr2-1 (light plants), and this is dramatically increased in plants homozygous for Mop1-1 or rmr2-1 (dark plants). This result was observed for both the b1 transcript and for the vector backbone (+SK) used in the original construct. The latter result indicates that the vector backbone is being transcribed. The VCL44-27A transgene contains multiple rearranged copies (Y. Lin and V. Chandler, unpublished data), which is clearly enabling transcription of the vector sequences to occur, presumably due to juxtaposition near a promoter.

The transgene can remain active when Mop1-1 and rmr2-1 are segregated away. We next tested whether the transgene could remain active in progeny plants that were again heterozygous for the mutations. For this experiment multiple individual plants that contained the active 35SB-Igen transgene and were homozygous for Mop1-1, rmr1-1 or rmr2-1 were outcrossed to b R-g P/stocks, which contained dominant functional alleles for all three genes (Mop1, rmr1 and rmr2). Purple seed, which contained the transgene were planted and the resulting plants scored for transgene pigmentation. With rmr1-1, all of the resulting plants were green, indicating that the transgene was efficiently resilenced in the presence of a functional Rmr1 allele. For Mop1-1 and rmr2-1, the transgene was resilenced in most of the progeny, but there were exceptions, indicating that in rare individuals the transgene could remain active, even in the presence of functional Mop1 or Rmr2 alleles. The number of plants that produced progeny with an active transgene and the total number tested are summarized for each mutation in Table 13.

TABLE 13

Heritability of the active transgene in heterozygous plants

|  | Mop1-1 | rmr1-1 | rmr2-1 |
|---|---|---|---|
| # homozygous plants outcrossed to wildtype | 9 | 33 | 8 |
| # with dark progeny | 4 | 0 | 5 |
| # total progeny scored | 183 | 590 | 198 |
| # dark plants | 15 | 0 | 21 |

We then tested whether the transgene that remained active in Mop1/Mop1-1 or Rmr2/rmr2-1 plants would remain active into the next generation by crossing these again to b R-g P/testers. One-half of the progeny would be expected to be heterozygous for Mop1-1 or rmr2-1 and the other half homozygous wild type. Seeds containing the transgene were identified by their seed pigmentation, planted and scored for transgene expression in the plant. A total of 6 and 12 plants from the Mop1 and rmr2 experiments were tested, respectively (Table 14). Six of the six Mop1/Mop1-1 heterozygotes and 11/12 of the Rmr2/rmr2-1 heterozygotes transmitted active transgenes to most if not all of their progeny (Table 14). Interestingly, in this last generation there was a much larger number of progeny plants that carried an active transgene, as compared to the first generation of crosses (compare Table 13 and Table 14), indicating that the transgene was heritably activated and it remains active in subsequent generations in the absence of the mutations that induced the original activation. Thus, it may be possible to use these mutations to activate other silent transgenes and then segregate the mutations from the active transgene. Additional crosses are in progress to determine the stability of the active transgenes in the absence of the mutations.

TABLE 14

Heritability of the active transgene in wildtype plants.

|  | Mop 1-1 | rmr2-1* |
|---|---|---|
| # heterozygous plants outcrossed to wildtype | 6 | 12 |
| # with dark progeny | 6 | 11 |
| # total progeny scored | 390 | 567 |
| # dark plants | 338 | 333 |

*A functional r1 allele that pigments the seed is segregating in these crosses, such that not all plants with purple seed will carry the transgene.

Summary. Our results demonstrate that four different genes that are required for paramutation (Mop1, mop2, rmr1 and rmr2) are also required to maintain the silent state of several transgene loci. Our initial results with mutations in two genes (Mop1-1 and rmr2-1) suggest that the activation is occurring at the transcriptional level. Our experiments further demonstrate that the Mop1-1 and rmr2-1 mutations can heritably activate the transgene, such that it remains active even when the mutations are segregated away. Additional experiments need to be done to determine the stability of the transcriptional activation and to determine if the other two mutations, Mop2-1 and rmr1-1 also activate the transgene at the transcriptional level. While all of the transgenes tested contain part of the b1 gene, none of the transgenes contain the sequences required for b1 paramutation (M. Stam and V. Chandler, unpublished data). Thus, we hypothesize that the activation of the b1 transgenes by these mutations will be a general effect that will occur with other transgenes as well. This is currently being tested using several transgenes that contain no b1 sequences. Additional experiments will also be required to determine if these mutations can activate transgenes that are post-transcriptionally silenced.

Example 6

Identification and Characterization of Additional Recessive Mutations that Reduce the Maintenance of pl1 Paramutation Overview. Additional maize mutations that reduce the maintenance of the Pl' paramutant state were identified from seedling screens similar to those described in Example 3 and mature plant screens using EMS-derived materials described in Example 3. Genetic complementation tests suggest that these mutations define five novel rmr loci (rmr6, rmr7, rmr8, rmr9, rmr11) and two new alleles of Mop1. RMR6 is required for transcriptional repression of Pl'. RMR6, RMR9 and RMR11 functions are required to heritably maintain the Pl' paramutant state. Phenotypic analysis indicates that RMR6, RMR8, and RMR11 functions are important for proper plant growth and development. Mutant corn plants that are homozygous for mutations in either the rmr7 and rmr9 genes have a normal developmental phenotype.

1. Materials and Methods:
See Example 3.

2. Identification and Characterization of the rmr6 Locus.
Description. Seedling screening similar to that described in Example 3 was used to identify an M2 family (96406) that segregated darkly pigmented seedlings. The genetic factor responsible for this darkly pigmented seedling phenotype is inherited as a single locus recessive factor that is not closely linked to the pl1 locus (see below). Genetic complementation test results (see below) demonstrate that this recessive factor defines a novel locus designated required to maintain repression 6 (rmr6) whose function is needed to maintain transcriptional repression of Pl' and sexual transmission of the Pl' paramutant state at a 100% frequency. The recessive rmr6 mutation identified by the seedling screen is designated rmr6-1.

rmr6-1 is inherited as a single locus recessive mutation. Homozygous rmr6-1/rmr6-1 plants having a Pl-Rh-like phenotype were outcrossed to Pl'/Pl' testers. All F1 progeny plants (32 individuals from 5 independent outcrosses) had a Pl' anther phenotype (7 ACS 1; 17 ACS 2; 8 ACS 3) indicating that the rmr6-1 allele is recessive and further that Pl' alleles transmitted from homozygous rmr6-1/rmr6-1 plants are not recalcitrant to subsequent paramutation. The Pl-Rh-like phenotype was recovered in 21/123 (17%) F2 plants derived from three independent self-pollinations of F1 plants (44 ACS 1; 46 ACS 2; 12 ACS 3; 21 ACS 7). The observed frequency of mutant phenotypes (17%) is not significantly different from the 25% expected from the segregation of a single locus recessive mutation ($\chi^2=0.32$; P>0.05).

rmr6-1 defines a trans-acting function acting upon Pl. The mutant phenotype (Pl-Rh-like anthers) did not cosegregate with alleles of salmon silks1 (sm1), a genetic locus 10 cM distal to the pl1 locus. The Pl-Rh allele subjected to EMS mutagenesis is genetically linked to the recessive sm1 allele sm1-EMS, therefore any mutations that occur close to the pl1 locus should also be genetically linked to sm1-EMS. One of the F2 families described above had individuals that were either wild type or mutant with regards to the salmon silks trait. Two of 43 (5%) of the wild type plants (Sm1/Sm1 or Sm1/sm1-EMS) had a Pl-Rh-like phenotype and 3 of 11 (27%) of the mutant (sm1-EMS/sm1-EMS) plants had a Pl-Rh-like phenotype. The absence of strong cosegregation between the Pl-Rh-like phenotypes and mutant sm1 phenotypes indicates that rmr6-1 is not tightly linked to sm1 and therefore not tightly linked to pl1. This result strongly suggests that the rmr6 locus is distinct from pl1.

rmr6-1 defines a novel rmr locus. Complementation crosses were made between homozygous mutant plants (Pl-Rh anthers) and plants heterozygous for each different mutation (Pl' anthers). All tests completed to date are summarized in Table 15. The rmr6-1 mutation clearly complemented all the mutations, except rmr11-1. If rmr6-1 and rmr11-1 were alleles of the same gene, we would expect that ½ of the complementation test progeny (~26 individuals) would have Pl-Rh-like anthers. Our observed frequency of Pl-Rh-like phenotypes (15/52) is significantly different from this expectation ($\chi^2=5$; P<0.05). Given that the rmr11-1 mutation also shows non-complementation with the rmr1-1 mutation, the most likely interpretation of these results is that rmr6-1 defines a locus distinct from rmr11. However, the observed partial non-complementation suggests that RMR6 and RMR11 functions may cooperate to achieve efficient repression of Pl'.

TABLE 15

Complementation Tests

| Alleles Tested | Ears Examined | Number of Plants with Given Anther Color Score | | | | | | |
|---|---|---|---|---|---|---|---|---|
| | | 1 | 2 | 3 | 4 | 5 | 6 | 7 |
| rmr6-1 | | | | | | | | |
| rmr1-1 | 4 | 19 | 35 | 28 | 5 | 1 | 1 | 0 |
| rmr2-1 | 4 | 14 | 38 | 35 | 1 | 0 | 0 | 0 |
| Mop1-1 | 3 | 22 | 27 | 6 | 1 | 0 | 0 | 0 |
| rmr7-1 | 2 | 13 | 10 | 2 | 0 | 0 | 0 | 0 |
| rmr7-2 | 2 | 11 | 18 | 2 | 0 | 0 | 0 | 0 |
| rmr8-1 | 2 | 4 | 22 | 3 | 0 | 0 | 0 | 0 |
| rmr9-1 | 2 | 1 | 16 | 10 | 0 | 0 | 0 | 0 |
| rmr11-1 | 3 | 1 | 13 | 17 | 6 | 1 | 0 | 15 |
| Mop1-4 | 2 | 1 | 16 | 10 | 0 | 0 | 0 | 0 |
| Mop1-5 | 2 | 7 | 15 | 2 | 1 | 0 | 0 | 0 |
| rmr7-1 | | | | | | | | |
| rmr1-1 | 3 | 16 | 16 | 3 | 0 | 0 | 0 | 0 |
| rmr2-1 | 2 | 12 | 13 | 4 | 0 | 0 | 0 | 0 |
| Mop1-1 | 3 | 23 | 10 | 2 | 0 | 0 | 0 | 0 |
| Mop1-4 | 2 | 21 | 12 | 3 | 0 | 0 | 0 | 0 |
| Mop1-5 | 1 | 10 | 11 | 0 | 1 | 0 | 0 | 0 |
| rmr7-2 | 2 | 6 | 8 | 1 | 1 | 5 | 11 | 5 |
| rmr8-1 | 1 | 20 | 28 | 0 | 0 | 0 | 0 | 0 |
| rmr9-1 | 2 | 12 | 14 | 2 | 0 | 0 | 0 | 0 |
| rmr7-2 | | | | | | | | |
| rmr1-1 | 2 | 19 | 11 | 0 | 0 | 0 | 0 | 0 |
| rmr2-1 | 2 | 11 | 23 | 1 | 1 | 0 | 0. | 0 |
| Mop1-1 | 2 | 18 | 13 | 1 | 0 | 0 | 0 | 0 |
| Mop1-4 | 2 | 13 | 19 | 5 | 0 | 0 | 0 | 0 |
| rmr8-1 | 2 | 5 | 18 | 3 | 1 | 0 | 0 | 0 |
| rmr9-1 | 2 | 3 | 33 | 1 | 0 | 0 | 0 | 0 |
| rmr8-1 | | | | | | | | |
| rmr1-1 | 3 | 6 | 11 | 5 | 7 | 5 | 1 | 0 |
| rmr2-1 | 1 | 0 | 1 | 10 | 2 | 0 | 0 | 0 |
| Mop1-2EMS | 2 | 0 | 9 | 7 | 7 | 5 | 3 | 2 |
| Mop1-4 | 1 | 2 | 7 | 5 | 5 | 1 | 1 | 1 |
| Mop1-5 | 2 | 9 | 16 | 2 | 0 | 1 | 0 | 0 |
| rmr9-1 | 3 | 6 | 11 | 4 | 10 | 13 | 20 | 6 |
| rmr9-1 | | | | | | | | |
| rmr1-1 | 3 | 4 | 12 | 13 | 0 | 0 | 0 | 0 |
| rmr2-1 | 2 | 1 | 6 | 21 | 1 | 0 | 0 | 0 |
| Mop1-2EMS | 2 | 1 | 8 | 19 | 1 | 0 | 0 | 0 |
| Mop1-4 | 1 | 4 | 21 | 1 | 0 | 0 | 0 | 0 |
| Mop1-5 | 2 | 10 | 16 | 5 | 1 | 0 | 0 | 0 |
| rmr11-1 | 1 | 1 | 3 | 6 | 0 | 0 | 0 | 0 |
| rmr11-1 | | | | | | | | |
| rmr1-1 | 3 | 11 | 20 | 2 | 2 | 0 | 1 | 37 |
| rmr2-1 | 1 | 13 | 13 | 0 | 0 | 0 | 0 | 0 |
| Mop1-4 | 1 | 10 | 7 | 4 | 0 | 0 | 0 | 0 |
| Mop1-4 | | | | | | | | |
| rmr1-1 | 2 | 4 | 19 | 17 | 0 | 0 | 0 | 0 |
| rmr2-1 | 1 | 2 | 14 | 10 | 0 | 0 | 0 | 0 |
| Mop1-1 | 2 | 8 | 8 | 5 | 0 | 0 | 0 | 8 |
| Mop1-5 | 2 | 1 | 14 | 1 | 2 | 0 | 0 | 8 |
| Mop1-5 | | | | | | | | |
| rmr1-1 | 2 | 1 | 12 | 1 | 1 | 0 | 0 | 0 |
| rmr2-1 | 2 | 10 | 11 | 2 | 4 | 0 | 0 | 0 |
| Mop1-1 | 2 | 5 | 1 | 1 | 0 | 0 | 0 | 12 |

Complementation tests identify four unique loci. For each allele listed in bold, the underlying series of alleles were tested for complementation. The number of ears sampled for each test are indicated along with the total numbers of mature plants with a given Anther Color Score derived from the seeds off those ears. Complementation should result in all plants with an ACS between 1–5. This result is consistent with the mutations being in different genes. Failure to complement would produce 50% darkly pigmented individuals (ACS 6–7). The simplest interpretation of this result is that the two mutations are in the same gene. However, it is also possible that when two genes are acting on the same pathway, double heterozygotes can show failure to complement. This is well documented and referred to as extragenic noncomplementation.

Pl' can change back to Pl-Rh in homozygous rmr6-1/rmr6-1 plantS. Crosses were made to four different homozygous Pl-Rh tester stocks to determine if all the pl1 alleles sexually transmitted from Pl'/Pl'; rmr6-1/rmr6-1 plants remained paramutagenic. Normally, crosses between Pl-Rh/Pl-Rh testers and Pl'/Pl' plants give rise exclusively to progeny with a Pl'/Pl' phenotype and genotype (Hollick et al. 1995). Twenty-five out of 36 crosses made between Pl-Rh/Pl-Rh testers and Pl'/Pl'; rmr6-1/rmr6-1 plants gave rise to plants with P1-Rh-like anthers. In total, 167/688 (24%) of the testcross progeny had ACS7 anthers (73 ACS 1; 232 ACS 2; 117 ACS 3; 50 ACS 4; 32 ACS 5; 17 ACS 6; 167 ACS 7). Thus Pl' alleles can change back to a meiotically-heritable, non-paramutagenic, Pl-Rh state in plants homozygous for rmr6-1.

The rmr6-1 mutation affects plant development. The Pl-Rh-like phenotype seen in homozygous rmr6-1 plants cosegregates with uniform alterations of normal plant development. First, homozygous rmr6-1 plants flower 5–7 days later, on average, than their heterozygous siblings. Second, homozygous rmr6-1 plants are 25% shorter, on average, than their heterozygous siblings. Third, homozygous rmr6-1 plants resemble tiller shoots in that there is frequent feminization of the apical inflorescence (FIG. 35), retardation of internode elongation for the apical leaves, and poor ear shoot development including the occurrence of disorganized rows of grains on the mature ears. Pollen grains from homozygous rmr6-1 plants appear visibly normal although no fertility tests have been conducted. These morphological phenotypes have been seen in all rmr6-1 families tested to date including introgression material using the maize elite inbred A632.

The rmr6 gene product is required for transcriptional repression of the Pl' allele. RNase protection experiments like those described in Examples 1 and 3 indicate that pI1 RNA levels are 26-fold higher in anther tissues of homozygous rmr6-1 plants relative to their heterozygous siblings (FIG. 36A). Five independent in vitro transcription assays (see Example 1 for methods) using isolated husk nuclei demonstrate that pI1 transcription is 4-fold higher in homozygous rmr6-1 plants relative to their heterozygous siblings (FIGS. 36B–C). Thus RMR6 function is required to maintain transcriptional repression of the Pl' allele.

RMR6 is required to maintain cytosine methylation at mutator terminal inverted repeats. Genomic DNA samples from a family of individuals segregating 1:1 for rmr6-1/rmr6-1 and rmr6-1/+ types was analyzed for the cytosine methylation status of Mu1 sequences as described in Example 2 above. All five of the rmr6-1/+ plants had hypermethylated Mu1 terminal inverted repeats, whereas six of the seven rmr6-1/rmr6-1 plants had hypomethylated Mu1 terminal inverted repeats (FIG. 34A). Thus RMR6 function appears to be involved in maintaining the hypermethylated state of Mu1 terminal inverted repeat sequences.

4. Identification and Characterization of the rmr7 Locus.

Description. Seedling screens similar to that described in Example 3 were used to identify two M2 families (9650 and 98939) that segregated darkly pigmented seedlings. The genetic factors responsible for these darkly pigmented seedling phenotypes are inherited as single locus recessive factors that are not genetically linked to the pI1 locus (see below). Genetic complementation test results (Table 15) demonstrate that these two recessive factors define a novel locus designated required to maintain repression 7 (rmr7). The recessive rmr7 mutations identified by the seedling screens are designated rmr7-1 (formerly 9650) and rmr7-2 (formerly 98939).

rmr7-1 is inherited as a single locus recessive mutation. Homozygous rmr7-1/rmr7-1 plants having a Pl-Rh-like phenotype were outcrossed to Pl'/Pl' testers. All the F1 progeny plants (22 individuals from 2 independent outcrosses) had a Pl' anther phenotype indicating that the rmr7-1 allele is recessive and further that Pl' alleles transmitted from homozygous rmr7-1/rmr7-1 plants are still capable of causing paramutation. The Pl-Rh-like phenotype was recovered in 34/154 (22%) F2 plants derived from seven independent self-pollinations of F1 plants (120 ACS 1-ACS 4; 34 ACS 7). The observed frequency of mutant phenotypes (22%) is not significantly different from the 25% expected from a single locus recessive mutation ($\chi^2$=0.53; P>0.05).

rmr7-2 is transmitted as a recessive mutation. Homozygous rmr7-2/rmr7-2 plants having a Pl-Rh-like phenotype were outcrossed to Pl'/Pl' testers. All F1 progeny plants (23 individuals from 2 independent outcrosses) had a clear Pl' anther phenotype indicating that the rmr7-2 allele is recessive and further that Pl' alleles transmitted from homozygous rmr7-2/rmr7-2 plants are not recalcitrant to subsequent paramutation.

rmr7-1 defines a trans-acting function acting upon Pl. The Pl-Rh-like anther phenotype conferred in rmr7-1/rmr7-1 plants did not co-segregate with the pI1 locus in a F2 mapping population. The F2 mapping population was derived by first crossing a Pl'/Pl'; rmr7-1/rmr7-1 plant to the elite inbred A632 (pI-A632/pI-A632; Rmr7-A632/Rmr7-A632) and then self-pollinating one of the resultant F1 plants. Fifty-six of 189 (30%) F2 plants were Pl/P/based on linked simple satellite repeat (SSR) polymorphisms yet only ten of these 56 Pl/P/plants (18%) had a Pl-Rh-like anther phenotype (10 ACS 7). If the rmr7-1 mutation was tightly linked to the Pl' allele then the expectation was that greater than 50% of the Pl/P/F2 plants would also have a darkanther phenotype. The absence of co-segregation between the Pl/P/genotype and the Pl-Rh-like phenotype indicates that the rmr7 locus is unlinked to the pI1 locus. All 46 pI-A632/pI-A632 plants had visibly similar levels of anther pigment suggesting that RMR7 function specifically affects expression of the Pl' allele and is not a general modifier of other pI1 alleles or of anthocyanin production in general.

rmr7-1 and rmr7-2 define a novel rmr locus. Complementation crosses were made between homozygous mutant (Pl-Rh anthers) plants and plants heterozygous for a different mutation (Pl' anthers). Results of these complementation crosses are shown in Table 15. The rmr7-1 and rmr7-2 mutations fail to complement each other indicating that these two mutations define alleles of the same gene. Other test results demonstrate that the rmr7-1 mutation complements mutations at rmr1, rmr2, Mop1, rmr6, rmr8, and rmr9. Thus the rmr7-1 and rmr7-2 mutations identify a novel rmr locus, required to maintain repression 7.

Pl' does not change back to a meiotically-heritable Pl-Rh state in homozygous rmr7-1 or rmr7-2 plants. In wild type backgrounds, crosses between Pl-Rh/Pl-Rh testers and Pl'/Pl' plants give rise exclusively to progeny with a Pl'/Pl' phenotype and genotype (Hollick et al. 1995). However, Pl' can change back to Pl-Rh at particular frequencies when carried with several of the other homozygous mutants (Mop1-1, Dorweiler et al, 2000; rmr1-1, rmr1-2, rmr2-1, Hollick and Chandler 2001; and rmr6-1, rmr9-1, rmr11-1, this document). To determine if all the pI1 alleles sexually transmitted from Pl'/Pl'; rmr7-1/rmr7-1 plants remained paramutagenic, crosses were made to seven different homozygous P1-Rh tester stocks. None of the 12 crosses made between Pl-Rh/Pl-Rh testers and Pl'/Pl'; rmr7-1/rmr7-1 plants gave rise to progeny plants with Pl-Rh-like anthers. The distribution of anther color scores among the progeny was (119/235 ACS 1; 100/235 ACS 2; 12/235 ACS 3; 4/235 ACS 4). Similarly, crosses were made to four different homozygous Pl-Rh tester stocks to determine if all the pI1 alleles sexually transmitted from Pl'/Pl', rmr7-2/rmr7-2 plants remained paramutagenic. None of the 4 crosses made between Pl-Rh/Pl-Rh testers and Pl'/Pl'; rmr7-

2/rmr7-2 plants gave rise to progeny plants with Pl-Rh-like anthers. The distribution of anther color scores among the progeny was (25/69 ACS 1; 39/69 ACS 2; 5/69 ACS 4). These anther color scores are very similar to that seen in the progenies of crosses between Pl'/Pl' (wild type for all paramutation defect loci) and Pl-Rh/Pl-Rh plants (Hollick et al. 1995). Thus, there is no evidence that lack of RMR7 function allows Pl' to change back to a meiotically-heritable Pl-Rh state.

The rmr7-1 and rmr7-2 mutations do not affect plant development. The Pl-Rh-like phenotype seen in homozygous rmr7-1 and homozygous rmr7-2 plants is not associated with any obvious developmental abnormalities. Field observations of F2 families segregating either the rmr7-1 or rmr7-2 mutations as well as comparison of rmr7-1/rmr7-1 and rmr7-1/+ individuals derived from intercrossing rmr7-1/rmr7-1 and rmr7-1/+ F2 siblings show relative uniformity of plant morphology. There are currently no observations to indicate that RMR7 functions are required for normal growth and development.

5. Identification and Characterization of the rmr8 Locus.

Description. This locus was identified from screening mature plant phenotypes of M2 families derived from the original chemical mutagenesis described in Example 3. Mature plants with full-colored anthers were found segregating in this particular M2 family (9583). This mutation does not affect the seedling pigment phenotype of Pl' plants; its effects are only manifest in the main body of the plant and in the anthers. Homozygous rmr8-1/rmr8-1, Pl'/Pl' seedlings have weak coloration indistinguishable from that of Pl'/Pl' seedlings but the anthers of rmr8-1/rmr8-1, Pl'/Pl' plants are indistinguishable from those of Pl-Rh/Pl-Rh plants. The genetic factor responsible for this darkly pigmented anther phenotype is inherited as a single locus recessive factor that is genetically unlinked to the pI1 locus (see below). Genetic complementation test results (Table 15) demonstrate that this recessive factor defines a novel locus designated required to maintain repression 8 (rmr8). The recessive rmr8 mutation identified by the mature plant screen is designated rmr8-1.

rmr8-1 is inherited as a single locus recessive mutation. Homozygous rmr8-1/rmr8-1 plants having a Pl-Rh-like phenotype were outcrossed to Pl'/Pl' testers. All F1 progeny plants (29 individuals from 2 independent outcrosses) had a clear Pl' anther phenotype indicating that the rmr8-1 allele is recessive and further that Pl' alleles transmitted from homozygous rmr8-1/rmr8-1 plants are still capable of paramutation. The dark-anther phenotype (ACS 5, 6, and 7 classes) was recovered in 7/54(13%) F2 plants derived from three independent self-pollinations of F1 plants (3 ACS 1; 18 ACS 2; 21 ACS 3; 5 ACS 4; 2 ACS 5; 2 ACS 6; 3 ACS 7). The observed frequency of non-Pl' phenotypes (13%) is significantly different from the 25% expected from a single locus recessive mutation ($\chi^2=3.13$; P<0.05) and is also significantly different from the 6.25% expected if the dark-anther trait is due to the presence of two unlinked recessive mutations ($\chi^2=3.89$; P<0.05). It is possible that the low frequency of dark-anthered plants in these F2 families was due to lethal effects of an EMS-induced mutation found closely linked to rmr8. In support of this hypothesis, segregation ratios more closely approximated 25% in subsequent F2 families derived from advanced generations of rmr8-1/rmr8-1 material. Four of 17 (24%) and 33/119 (28%) F2 plants from two independent families had dark-anther phenotypes (combination of ACS 5, 6 and 7) consistent with the hypothesis that the dark-anther phenotype is due to a single locus recessive mutation.

rmr8-1 defines a trans-acting function affecting anther pigmentation. The dark-anther phenotype conferred in rmr8-1/rmr8-1 plants did not co-segregate with the pI1 locus in a F2 mapping population. The F2 mapping population was derived by first crossing a Pl'/Pl'; rmr8-1/rmr8-1 plant to the elite inbred A632 (pI-A632/pI-A632; Rmr8-A632/Rmr8-A632) and then self-pollinating one of the resultant F1 plants. Forty-one of 169 (24%) F2 plants were Pl/P/based on linked simple satellite repeat (SSR) polymorphisms yet only six of these 41 Pl/P/plants (15%) had a dark-anther phenotype (1 ACS 5; 1 ACS 6; 4 ACS 7). If the rmr8-1 mutation was linked to the Pl' allele then the expectation was that greater than 50% of the Pl/P/F2 plants would also have a dark-anther phenotype. The absence of co-segregation between the Pl/P/genotype and the dark-anther phenotype indicates that the rmr8 locus is unlinked to the pI1 locus. Eleven of 46 pI-A632/pI-A632 plants (24%) had visibly more anther pigment than the remaining pI-A632/pI-A632 siblings. This is the frequency of individuals expected to carried be homozygous for rmr8-1 allele, suggesting that RMR8 function might increase pigment on other pI1 alleles in addition to the Pl' allele (see below).

rmr8-1 defines a novel rmr locus. Complementation crosses were made between homozygous mutant (Pl-Rh anthers) plants and plants heterozygous for a different mutation (Pl' anthers). Results shown in Table 15 indicate that the rmr8-1 mutation complements the rmr1-1, rmr2-1, rmr6-1, rmr7-1, and Mop1-5 mutations, suggesting it is at a distinct locus. However, rmr8-1 showed partial complementation with the rmr9-1, Mop1-2EMS, and Mop1-4 mutations. if the rmr8-1 mutation is an allele of Mop1 the expectation is that all alleles of Mop1 should behave similarly. This was not observed. No dark anthered individuals were observed in progeny from the Mop1-5 experiments, and much fewer than the predicted 50% were observed in progeny from the Mop1-4 experiment (Table 15). Only 1/22 progeny from this cross had a Pl-Rh-like anther phenotype (2 ACS 1; 7 ACS 2; 5 ACS 3; 5 ACS 4; 1 ACS 5; 1 ACS 6; 1 ACS 7) and only 3/22 progeny had a dark-anther phenotype (ACS 5, 6 or 7). Finally, the observed frequency of Pl-Rh-like types (ACS 7) in the Mop1-2EMS progeny is significantly different from the frequency expected for this hypothesis ($\square 2=12.25$; P<0.01), but the observed frequency of dark-anther phenotypes (ACS 5, 6 or 7) is not significantly different from 50% ($\square 2=2.25$). The most likely interpretation of these results is that rmr8-1 and several Mop1 alleles show partial non-complementation and rmr8-1 defines a locus distinct from Mop1. The observed partial non-complementation suggests that RMR8 and Mop1 functions may cooperate to achieve efficient repression of Pl'.

If the rmr8-1 mutation is an allele of rmr9, then ½ of all progeny (35 individuals) from these two crosses should have a Pl-Rh-like anther phenotype. The observed frequency of Pl-Rh-like types is significantly different from the expected frequency for this hypothesis ($\chi^2=24$; P<0.01). However, the observed frequency of dark-anther phenotypes (ACS 5, 6 or 7) is not significantly different from 50% ($\chi^2=0.71$; P>0.05). Given that the rmr9-1 mutation shows full complementation with the Mop1-2EMS and Mop1-4 mutations (Table 15), while the rmr8-1 mutation partially complements these mutations, the most likely interpretation of these results is that rmr8-1 defines a locus distinct from rmr9. The observed partial non-complementation between rmr8-1 and rmr9-1 suggests that RMR8 and RMR9 functions may cooperate to achieve efficient repression of Pl'. It is interesting that rmr8-1 interacts with both rmr9-1 and several Mop1 mutations, but there is no observed interaction in the complementation tests between rmr9-1 and the Mop1 mutations.

PI' does not change back to a meiotically-heritable PI-Rh state in homozygous rmr8-1/rmr8-1 plants. Crosses were made to four different homozygous PI-Rh tester stocks to determine if all the pI1 alleles sexually transmitted from PI'/PI'; rmr8-1/rmr8-1 plants remained paramutagenic, which occurs in wild type stocks (Hollick et al. 1995). None of the 4 crosses made between PI-Rh/PI-Rh testers and PI'/PI'; rmr8-1/rmr8-1 plants gave rise to progeny plants with PI-Rh-like anthers. The distribution of anther color scores among the progeny (9/86 ACS 1; 51/86 ACS 2; 13/86 ACS 3; 3/86 ACS 4) is very similar to that seen in the progenies of crosses between PI'/PI' in wild type stocks and PI-Rh/PI-Rh plants (Hollick et al. 1995). Thus, there is no evidence that lack of RMR8 function allows PI' to change back to a meiotically-heritable PI-Rh state.

The rmr8-1 mutation affects plant development. The PI-Rh-like phenotype seen in homozygous rmr8-1 plants co-segregates with uniform developmental abnormalities. Homozygous rmr8-1 plants have a smaller tassel with reduced numbers of tassel branches, failure of anther extrusion from the glumes, and a limited development of female reproductive structures in the tassel. The severity of this suite of traits is fairly consistent and all the plants with darkly pigmented anthers clearly have the same suite of developmental abnormalities. The severity of these abnormal phenotypes remains constant in advanced generations (3 generations of self-pollination) of a homozygous rmr8-1 background.

The rmr8 gene product is required for repression of PI' expression. A single RNase protection experiment like those described in Examples 1 and 3 indicate that pI1 RNA levels are 11-fold higher in anther tissues of homozygous rmr8-1 plants relative to their heterozygous siblings. It unknown if this effect on pI1 RNA levels is controlled at the transcriptional or post-transcriptional level. Nonetheless, RMR8 function is required to maintain repression of the PI' allele.

6. Identification and Characterization of the rmr9 Locus

Description. This locus was identified from screening mature plant phenotypes of M2 families derived from the original chemical mutagenesis described in Example 3. Mature plants with full-colored anthers were found segregating in this particular M2 family (95270). This mutation does not affect the seedling pigment phenotype of PI' plants; its effects are only manifest in the main body of the plant and in the anthers. Homozygous rmr9-1/rmr9-1, PI'/PI' seedlings have weak coloration indistinguishable from that of PI'/PI' seedlings, while the anthers of rmr9-1/rmr9-1, PI'/PI' plants are indistinguishable from those of PI-Rh/PI-Rh plants. The genetic factor responsible for this darkly pigmented anther phenotype is inherited as a single locus recessive factor that is genetically unlinked to the pI1 locus (see below). Genetic complementation test results (Table 15) suggest that this recessive factor defines a novel locus designated required to maintain repression 9 (rmr9) whose function is required to maintain sexual transmission of the PI' paramutant state at 100% frequency. The recessive rmr9 mutation identified by the mature plant screen is designated rmr9-1.

rmr9-1 is inherited as a single locus recessive mutation. Homozygous rmr9-1/rmr9-1 plants having a P1-Rh-like phenotype were outcrossed to PI'/PI' testers. All F1 progeny plants (23 individuals from a single outcross) had a PI' anther phenotype indicating that the rmr9-1 allele is recessive and further that PI' alleles transmitted from homozygous rmr9-1/rmr9-1 plants are not recalcitrant to subsequent paramutation. The PI-Rh-like anther phenotype (ACS 7) was recovered in only 2/29 (7%) F2 plants derived from three independent self-pollinations of F1 plants (3 ACS 1; 12 ACS 2; 6 ACS 3; 6 ACS 4; 2 ACS 7). The observed frequency of PI-Rh-like phenotypes (7%) is significantly different from the 25% expected from a single locus recessive mutation ($\chi^2=3.8$; P<0.05), but is not significantly different from the 6.25% expected if the dark-anther trait is due to the presence of two unlinked recessive mutations ($\chi^2=0.02$; P>0.05). It is also possible that the low frequency of dark-anther plants in these F2 families was due to lethal effects of an EMS-induced mutation found closely linked to rmr9. In support of this latter hypothesis, segregation ratios more closely approximated 25% in subsequent F2 families derived from advanced generation rmr9-1/rmr9-1 material. Three of 16 (19%) and 5/22 (23%) F2 plants from two independent families had PI-Rh-like anther phenotypes. These latter segregation ratios are more consistent with the single locus recessive hypothesis ($\chi^2=0.25$ and $\chi^2=0.045$, respectively) rather than a model in which the dark-anther trait is due to the presence of two unlinked recessive mutations ($\chi^2=4$; P<0.05 and $\chi^2=9.6$; P<0.01, respectively).

rmr9-1 defines a trans-acting function affecting anther pigmentation. The dark-anther phenotype conferred in rmr9-1/rmr9-1 plants did not co-segregate with specific pI1 alleles in a F2 segregating family. To generate this particular F2 family, a PI'/PI'; rmr9-1/rmr9-1 individual was first crossed to a PI'/PI' tester stock in which the PI' alleles are linked (<1cM) to a translocation breakpoint between the long arm of chromosome 6 and the short arm of chromosome 9. This translocation breakpoint is also tightly linked to a recessive kernel mutation at the waxy1 locus (wx1) found on chromosome 9. Thus the PI' alleles in these PI'/PI' testers are approximately 5cM from mutant wx1 alleles. Resulting F1 progeny had a clear PI' phenotype and also displayed ~25% pollen abortion, which is expected in a translocation heterozygote. Upon self-pollination, the ears of these F1 plants segregated ¼ waxy kernels as expected. Mutant wx1/wx1 kernels were selected and sowed. Three of the 16 plants grown from the wx1/wx1 kernels had a PI-Rh (ACS 7) phenotype. If the rmr9-1 mutation resides at the pI1 locus, then none of the wx1/wx1 kernels should have also been homozygous for the rmr9-1 mutation. Thus, preliminary data suggest that the rmr9 locus is distinct from pI1.

rmr9-1 defines a novel rmr locus. Complementation crosses were made between homozygous mutant (PI-Rh anthers) plants and plants heterozygous for a different mutation (PI' anthers). Results (Table 15) indicate that the rmr9-1 mutation complements mutations at rmr1, rmr2, Mop1, rmr6, rmr7 and rmr11. Thus the rmr9-1 mutation identifies a new rmr locus, rmr9. The interactions with rmr8-1 are discussed above.

PI' can change back to a meiotically-heritable PI-Rh state in homozygous rmr9-1/rmr9-1 plants. Crosses were made to five different homozygous PI-Rh tester stocks to determine if all the pI1 alleles sexually transmitted from PI'/PI'; rmr9-1/rmr9-1 plants remained paramutagenic as observed in wild type stocks (Hollick et al. 1995). One of the 5 crosses made between PI-Rh/PI-Rh testers and PI'/PI'; rmr9-1/rmr9-1 plants gave rise to one progeny plant with PI-Rh-like anthers. In addition, the distribution of Anther Color Scores among all the progeny of these 5 crosses (6/100 ACS 1; 42/100 ACS 2; 23/100 ACS 3; 18/100 ACS 4; 10/100 ACS 5; 1/100 ACS 7) is skewed towards higher Anther Color Scores than seen in the progenies of crosses between PI'/PI' and PI-Rh/PI-Rh plants wild type for RMR9 (Hollick et al.

1995). Thus, preliminary data suggest that Pl' alleles can sometimes change back to a meiotically-heritable, non-paramutagenic or weakly-paramutagenic state in plants homozygous for rmr9-1.

The rmr9-1 mutation does not affect plant development. The P1-Rh-like phenotype seen in homozygous rmr9-1 plants is not associated with any obvious developmental abnormalities. Field observations of F2 families segregating the rmr9-1 mutation as well as comparison of rmr9-1/rmr9-1 and rmr9-1/+ individuals derived from intercrossing rmr9-1/rmr9-1 and rmr9-1/+ F2 siblings show relative uniformity of plant morphology. There are currently no observations to indicate that RMR9 functions are required for normal growth and development.

7. Identification and Characterization of the rmr11 Locus.

Description. Seedling screens similar to that described in Example 3 was used to identify an M2 family (98287) that segregated darkly pigmented seedlings. The genetic factor responsible for this darkly pigmented seedling phenotype is inherited as a single locus recessive factor that is not genetically linked to the pl1 locus (see below). Genetic complementation test results (see below) suggest that this recessive factor defines a novel locus designated required to maintain repression 11 (rmr11), although this mutation appears to interact with mutations at several other loci. Further genetic tests indicate that RMR11 function is required to maintain the Pl' paramutant state at 100% frequency through sexual transmission. The recessive rmr11 mutation identified by the seedling screen is designated rmr11-1.

rmr1-1 is inherited as a single locus recessive mutation. Homozygous rmr11-1/rmr11-1 plants having a PI1-Rh-like phenotype were outcrossed to PI-Rh/PI-Rh testers. Almost ½ of all the F1 progeny plants (8 of 25 individuals from two independent outcrosses) had a PI-Rh anther phenotype (2 ACS 1; 12 ACS 2; 2 ACS 4; 1 ACS 5; 8 ACS 7) suggesting that the rmr11-1 allele might represent a dominant mutation. However, the PI-Rh-like phenotype was recovered in 12/40 (30%) F2 plants derived from two independent self-pollinations of ACS 3 F1 plants (3 ACS 1; 19 ACS 2; 5 ACS 3; 1 ACS 4; 12 ACS 7). The observed frequency of F2 mutant phenotypes (30%) is not significantly different from the 25% expected from a single locus recessive mutation ($\chi^2=0.4$) and is consistent with the hypothesis that the dark-anther phenotype, is due to a single locus recessive mutation.

rmr11-1 defines a trans-acting function acting upon Pl'. The mutant phenotype (PI-Rh-like anthers) did not co-segregate with alleles of salmon silks1 (sm1), a genetic locus 10 cM distal to the pl1 locus. The PI-Rh allele that was subjected to EMS mutagenesis is genetically linked to the recessive sm1 allele, sm1-EMS. Therefore any mutations that occur close to the pl1 locus should also be genetically linked to sm1-EMS. One of the F2 families mentioned above was segregating the salmon silks trait. Three of 17 F2 progeny had the recessive sm1-EMS/sm1-EMS phenotype yet none of these three plants had dark-colored anthers. Thus, the rmr11-1 mutation appears to be genetically unlinked to the sm1 locus indicating that rmr11-1 defines a genetic locus distinct from pl1.

rmr11-1 defines a novel rmr locus. Complementation crosses were made between homozygous mutant (PI-Rh anthers) plants and plants heterozygous for a different mutation (PI' anthers). Results (Table 15) indicate that the rmr11-1 mutation complements mutations at rmr2, rmr9 and Mop1. However, the rmr11-1 mutation shows only partial complementation with the rmr6-1 mutation and absence of complementation with the rmr1-1 mutation. If the rmr11-1 mutation was an allele of rmr1, then ½ of all progeny (37 individuals) from the three complementation crosses should have a PI-Rh-like anther phenotype. The observed frequency of PI-Rh-like types (37/83) is not significantly different from the expected frequency for this hypothesis (36.5/83), suggesting that the rmr 11-1 and rmr1-1 mutations define the same locus. However, the rmr11-1 mutation also shows partial non-complementation with the rmr6-1 mutation, which is clearly a distinct locus from that defined by rmr1-1. Fifteen of the 53 progeny from the rmr6-1 complementation crosses had a PI-Rh-like anther phenotype (1 ACS 1; 13 ACS 2; 17 ACS 3; 6 ACS 4; 1 ACS 5; 15 ACS 7) demonstrating some non-complementation between the rmr6-1 and rmr11-1 mutations. If rmr6-1 and rmr11-1 were alleles of the same gene, we would expect that ½ of the progeny (26–27 individuals) would have PI-Rh-like anthers. Our observed frequency of PI-Rh-like phenotypes is significantly different from this expectation ($\chi^2=5$; $P<0.05$) indicating only partial genetic non-complementation. Given that the rmr11-1 mutation fails to complement mutations previously shown to be non-allelic, the most likely interpretation of these results is that rmr11-1 defines a locus distinct from either rmr1 or rmr6.

Pl' can change back to a meiotically-heritable PI-Rh state in homozygous rmr11-1/rmr11-1 plants. Crosses were made to five different homozygous PI-Rh tester stocks to determine if all the pl1alleles sexually transmitted from Pl'/Pl', rmr11-1/rmr11-1 plants remained paramutagenic as observed in wild type stocks (Hollick et al. 1995). Nine of the 15 crosses made between PI-Rh/PI-Rh testers and Pl'/Pl' rmr11-1/rmr11-1 plants gave rise to at least one progeny plant with PI-Rh-like anthers (43/252 ACS 1; 105/252 ACS 2; 20/252 ACS 3; 21/252 ACS 4; 8/252 ACS 5; 3/252 ACS 6; 52/252 ACS 7). Thus, Pl' alleles can sometimes change back to a meiotically-heritable, non-paramutagenic or weakly-paramutagenic state in plants homozygous for rmr11-1.

The rmr11-1 mutation affects plant development. The PI-Rh-like phenotype seen in homozygous rmr11-1 plants co-segregates with alterations of normal plant development. Homozygous rmr11-1 plants resemble tiller shoots in that there is frequent feminization of the apical inflorescence and there is poor ear shoot development, including the occurrence of disorganized rows of grains on the mature ears.

8. Identification and Characterization of the Mop1-4 and Mop1-5 Mutations

Description. Seedling screens similar to that described in Example 3 was used to identify two M2 families (98262 and 98941) that segregated darkly pigmented seedlings. The genetic factors responsible for these darkly pigmented seedling phenotypes are inherited as single locus recessive factors (see below). Genetic complementation test results (Table 15) suggest that these two recessive factors define additional alleles of Mop1. Further genetic tests indicate that these mutations can reduce the ability to maintain the Pl' paramutant state at a 100% frequency through sexual transmission. The recessive mutations identified by these seedling screens are currently designated Mop1-4 and Mop1-5.

Mop1-4 is inherited as a single locus recessive mutation. Homozygous Mop1-4/Mop1-4 plants having a PI-Rh-like phenotype were outcrossed to Pl'/Pl' testers. All F1 progeny plants (39 individuals from 3 independent outcrosses) had a Pl' anther phenotype (5 ACS 1; 22 ACS 2; 12 ACS 3) indicating that the Mop1-4 allele is recessive and further that Pl' alleles transmitted from homozygous Mop1-4/Mop1-4 plants are capable of paramutation. The Pl-Rh-like anther phenotype (ACS 7) was recovered in 10/64 F2 plants derived from three independent self-pollinations of F1 plants (30 ACS 1; 15 ACS 2; 2 ACS 3; 10 ACS 7). The observed frequency of Pl-Rh-like phenotypes (16%) is not significantly different from the 25% expected from a single locus recessive mutation ($\chi^2=1.95$; P>0.05) but is significantly different from the 6.25% expected if the dark-anther trait is due to the presence of two unlinked recessive mutations ($\chi^2=9.7$; P<0.01). All F2 progeny with ACS 7 anthers were 213 the height of their Pl'-like siblings. Five of the 62 F2 progeny produced barren (no flowers) tassels so it was not possible to assign these to a given Anther Color Score class. However, these five anther-less progeny were short in stature and had very strong plant color similar to all other F2 plants that had ACS 7 anthers. If we include these five anther-less progeny among the "ACS 7" mutant class, then 15/62 (24%) of the F2 progeny have the mutant phenotype. These F2 segregation ratios are consistent with the hypothesis that the dark-anther phenotype, and the dark-plant phenotype, is due to a single locus recessive mutation.

Mop1-5 is transmitted as a recessive mutation. Homozygous Mop1-5/Mop1-5 plants having a Pl-Rh-like phenotype were outcrossed to Pl'/Pl' testers. All F1 progeny plants (14 individuals from 2 independent outcrosses) had a Pl' anther phenotype (2 ACS 1; 9 ACS 2; 2 ACS 3; 1 ACS 4) indicating that the Mop1-5 allele is recessive and further that Pl' alleles transmitted from homozygous Mop1-5/Mop1-5 plants are not recalcitrant to subsequent paramutation.

Mop1-4 and Mop1-5 define two new alleles of Mop1. Complementation crosses were made between homozygous mutant (Pl-Rh anthers) plants and plants heterozygous for a different mutation (Pl' anthers). Results (Table 15) indicate that the Mop1-4 and Mop1-5 mutations complement mutations at rmr1, rmr2, rmr6, rmr9 and rmr11. However, the two mutations fail to complement each other and the Mop1-1 mutation. If the Mop1-4 mutation is an allele of Mop1, then ½ of all progeny (15 individuals) from the two complementation crosses with Mop1-1 should have a Pl-Rh-like anther phenotype. The observed frequency of Pl-Rh-like types is not significantly different from the expected frequency for this hypothesis ($\chi^2=3.3$; P>0.05) suggesting that Mop1-4 defines an allele of Mop1. If the Mop1-5 mutation defines an allele of Mop1, then 50% of the complementation cross progeny made with Mop1-1 (9–10 individuals) should have a Pl-Rh-like anther phenotype. The observed frequency is not significantly different from this hypothesis ($\chi^2=0.66$; P>0.05) suggesting that Mop1-5 is an allele of Mop1.

Pl' can change back to a meiotically-heritable Pl-Rh state in homozygous Mop1-4 and Mop1-5 plants. Crosses were made to five different homozygous Pl-Rh tester stocks to determine if all the pl1 alleles sexually transmitted from Pl'/Pl'; Mop1-4/Mop1-4 plants remained paramutagenic as typically observed in wild type stocks (Hollick et al. 1995). Four of the 16 crosses made between Pl-Rh/Pl-Rh testers and Pl'/Pl'; Mop1-4/Mop1-4 plants gave rise to at least one progeny plant with Pl-Rh-like anthers (83/278 ACS 1; 117/278 ACS 2; 61/278 ACS 3; 7/278 ACS 4; 4/278 ACS 5; 6/278 ACS 7). Crosses were made to six different homozygous Pl-Rh tester stocks to determine if all the pl1 alleles sexually transmitted from Pl'/Pl'; Mop1-5/Mop1-5 plants remained paramutagenic. One of the 6 crosses made between Pl-Rh/Pl-Rh testers and Pl'/Pl'; Mop1-5/Mop1-5 plants gave rise to at least one progeny plant with Pl-Rh-like anthers (29/100 ACS 1; 55/100 ACS 2; 1/100 ACS 3; 7/100 ACS 4; 2/100 ACS 5; 0/100 ACS 6; 6/100 ACS 7).

Thus, preliminary data indicate that Pl' alleles can sometimes change back to a meiotically-heritable, non-paramutagenic or weakly-paramutagenic state in plants homozygous for Mop1-4 and Mop1F-5.

The Mop1-4 mutation affects plant development. The Pl-Rh-like phenotype seen in homozygous Mop1-4 plants co-segregates with obvious developmental abnormalities. Homozygous Mop1-4 plants are ⅓ shorter, on average than their heterozygous siblings. Measurements taken from three independent families in our 2000–2001 winter nursery in Molokai, HI., show an average height of 69 inches for Mop1-4 heterozygotes and 45 inches for homozygous siblings. In general, the Mop1-4 homozygotes also have a slightly bushier tassel with extra branches and shorter internode distances between the branches. However, dimorphic tassel phenotypes of homozygous Mop1-4 plants have been noted; tassels are smallish, thin, and sparsely adorned with florets in our Hawaii nurseries but relatively normal in our Albany, Calif. nursery. This phenotype is very similar to what has been reported for the Mop1-1 and Mop1-2EMS alleles (Dorweiler et al., 2000). In all other obvious respects, Mop1-4 homozygous plants appear to be normal.

The Mop1-5 mutation does not obviously affect plant development. The Pl-Rh-like phenotype seen in homozygous Mop1-5 plants is not associated with any obvious developmental abnormalities. Field observations of a single F2 family segregating the Mop1-5 mutation as well as comparison of Mop1-5/Mop1-5 and Mop1-5/+ individuals derived from intercrossing Mop1-5/Mop1-5 and Mop1-5/+ F2 siblings show relatively uniform plant morphology.

References

The following references are cited throughout the Specification and the Examples and each is hereby incorporated by reference in their entirety:

Alleman, M. and Kermicle, J. L. (1993). Somatic variegation and germinal mutability reflect the position of transposable element Dissociation within the maize R gene. Genetics 135: 189–203.

Amedeo, P., Habu, Y., Afsar, K., Mittelsten Scheid, O. and Paszkowski, J. (2000). Disruption of the plant gene MOM releases transcriptional silencing of methylated genes. Nature 405: 203–206.

Axtell, J. D. and Brink, R. A. (1967) Chemically induced paramutation at the R locus in maize. Proc. Natl. Acad. Sci. USA 58:181–187.

Bray and Brink (1966). Mutation and paramutation at the R locus in maize. Genetics 54:137–149.

Brink, R. A. (1956). A genetic change associated with the R locus in maize which is directed and potentially reversible. Genetics 41: 872–889.

Brink, R. A. (1958). Basis of a genetic change which invariably occurs in certain maize heterozygotes. Science 127: 1182–1183.

Brink and Mikula (1958). Plant color effects of certain anomalous forms of the Rr allele in maize. Z Ind Abst Vererb 89: 94–102.

Brink, R. A., Kermicle, J. L., and Ziebur, N. K. 1970. Derepression in the female gametophyte in relation to paramutant R expression in maize endosperms, embryos and seedlings. Genetics 66: 87–96.

Brink, R. A. (1973) Paramutation. Ann Rev Genet 7: 129–152.

Brink, R. A., Styles, E. D. and Axtell, J. D. (1968). Paramutation: Directed Genetic Change. Science 159:161–170.

Brown and Brink (1960). Paramutagenic action of paramutant Rr and Rg alleles in maize. Genetics 45:1313–1316.

Cavalli, G. and Paro, R. (1998). The *Drosophila* Fab-7 chromosomal element conveys epigenetic inheritance during mitosis and meiosis. Cell 93: 505–518.

Chandler, V. L. & Hardeman, K. J. (1992) Adv Genet 30, 77–122.

Chandler V L, Vaucheret H. Gene activation and gene silencing. Plant Physiol. 125:145–8.

Chandler, V. L. & Walbot, V. (1986) Proc Natl Acad Sci U S A 83, 1767–71.

Chandler, V. L., Eggleston, W. B. and Dorweiler, J. E. (2000). Paramutation in Maize. Plant Mol. Biol. 43: 121–145.

Chandler, V. L., Kubo, K. M. and Hollick, J. B. (1996). b and P/paramutation in maize: Heritable transcription states programmed during development. In Epigenetic Mechanisms of Gene Regulation, V. E. A. Russo, R. A. Martienssen and A. D. Riggs, eds (New York: Cold Spring Harbor Laboratory Press), 289–304.

Chomet, P., Lisch, D., Hardeman, K. J., Chandler, V. L. & Freeling, M. (1991) Genetics 129, 261–70.

Christensen, A. H., Sharrock, R. A. and Quail, P. H. (1992). Maize polyubiquitin genes: structure, thermal perturbation of expression and transcript splicing, and promoter activity following transfer to protoplasts by electroporation. Plant Mol. Biol. 18: 675–689.

Coe, E. H., Jr. (1959). A regular and continuing conversion-type phenomenon at the B locus in maize. Proc. Natl. Acad. Sci. USA 45: 828–832.

Coe, E. H., Jr. (1966). The properties, origin and mechanism of conversion-type inheritance at the b locus in maize. Genetics 53: 1035–1063.

Cogoni, C., and G. Macino, 1997 Isolation of quelling-defective (qde) mutants impaired in posttranscriptional transgene-induced gene silencing in Neurospora crassa. Proc. Natl. Acad. Sci. USA 94:10233–10238.

Colot, V., Maloisel, L. and Rossignol, J.-L. (1996). Interchromosomal transfer of epigenetic states in Ascobolus: transfer of DNA methylation is mechanistically related to homologous recombination. Cell 86: 855–864.

Cone, K. C., Cocciolone, S. M., Burr, F. A. and Burr, B. (1993). Maize anthocyanin regulatory gene P/is a duplicate of c1 that functions in the plant. Plant Cell 5: 1795–1805.

Cryderman, D. E., Morris, E. J., Biessmann, H., Elgin, S. C. R. and Wallrath, L. (1999). Silencing at *Drosophila* telomeres: nuclear organization and chromatin structure play critical roles. EMBO J 18: 3724–3735.

Csink, A. K., Linsk, R., and J. A. Birchler, 1994 The lighten up (Lip) gene of *Drosophila melanogaster,* a modifier of retroelement expression, position effect variegation and white locus insertion alleles. Genetics 138: 153–163.

Dalmay, T., Hamilton, A., Rudd, S., Angell, S., and D. C. Baulcombe, 2000 An RNA–Dependent RNA polymerase gene in *Arabidopsis* is required for posttranscriptional gene silencing mediated by a transgene but not by a virus. Cell 101: 543–553.

Dellaporta, S. L., Wood, J. and Hicks, J. B. (1983). A plant DNA mini preparation. Plant Mol. Biol. Rep. 1: 19–21.

Dooner, H. K. (1979) Identification of an R-locus region that controls the tissue specificity of anthocyanin formation in maize. Genetics 93:703–710.

Dooner, H., Robbins, T. P. and Jorgensen, R. A. (1991). Genetic and developmental control of anthocyanin biosynthesis. Annu. Rev. Genet. 25: 173–199.

Dorer, D. R., and S. Henikoff, 1994. Expansions of transgene repeats cause heterochromatin formation and gene silencing in *Drosophila*. Cell 77: 993–1002.

Dorweiler, J. E., Carey, C. C., Kubo, K. M., Hollick, J. B., Kermicle, J. L., et al., 2000 Mediator of paramutation 1 (Mops) is required for the establishment and maintenance of paramutation at multiple maize loci. Plant Cell 12: 2101–2118.

Eggelston, et al. (1995). Molecular organization and germinal instability of R-stippled maize. Genetics 141: 347–360.

Elmayan, T., Balzergue, S., Béon, F., Bourdon, V., Daubremet, J., Guenet, Y., Mourrain, P., Palauqui, J.-C., Vernhettes, S., Vialle, T., Wostrikoff, K. and Vaucheret, H. (1998). *Arabidopsis* mutants impaired in cosuppression. Plant Cell 10: 1747–1757.

Eshed, Y., Baum, S. F. and Bowman, J. L. (1999). Distinct mechanisms promote polarity establishment in carpels of *Arabidopsis*. Cell 99: 199–209.

Fagard, M. and Vaucheret, H. (2000). Annu. Rev. Plant Physiol. Plant Mol. Biol. 51:167–194.

Feinberg, A. P. and Vogelstein, B. (1983). A technique for radiolabeling DNA restriction endonuclease fragments to high specific activity. Anal. Biochem. 132: 6–13.

Finnegan, E. J., Peacock, W. J. and Dennis, E. S. (1996). Reduced DNA methylation in *Arabidopsis thaliana* results in abnormal plant development. Proc. Natl. Acad. Sci. USA 93: 8449–8454.

Furner, I. J., Sheikh, M. A. and Collett, C. E. (1998). Gene silencing and homology-dependent gene silencing in *Arabidopsis:* genetic modifiers and DNA methylation. Genetics 149: 651–662.

Gibbons, R. J., McDowell, T. L., Raman, S., O'Rourke, D. M., Garrick, D., Ayyub, H. and Higgs, D. R. (2000). Mutations in ATRX, encoding a SWI/SNF-like protein, cause diverse changes in the pattern of DNA methylation. Nat. Genet. 24: 368–371.

Goff, S. A., Cone, K. C. and Chandler, V. L. (1992). Functional analysis of the transcriptional activator encoded by the maize b gene: Evidence for a direct functional interaction between two classes of regulatory proteins. Genes Dev. 6: 864–875.

Goff, S. A., Klein, T. M., Roth, B. A., Fromm, M. E., Cone, K. C., Radicella, J. P. and Chander, V. L. (1990). Transactivation of anthocyanin biosynthetic genes following transfer of B regulatory genes into maize tissues. EMBO J 9: 2517–2522.

Grewal, S. I. S. and Klar, A. J. S. (1996). Chromosomal inheritance of epigenetic states in fission yeast during mitosis and meiosis. Cell 86: 95–101.

Grossniklaus, U., Vielle-Calzada, J. P., Hoeppner, M. A. and Gagliano, W. B. (1998). Maternal control of embryogenesis by MEDEA, a Polycomb group gene in *Arabidopsis*. Science 280:446–450.

Henikoff, S. and Comai, L. (1998). Trans-sensing effects: the ups and downs of being together. Cell 93: 329–332.

Henikoff, S., Jackson, J. M., and P. B. Talbert, 1995. Distance and pairing effects on the brown Dominant heterochromatic element in *Drosophila*. Genetics 140: 1007–1017.

Hollick, J. B. and Chandler, V. L. (2001). Genetic factors required to maintain repression of a paramutagenic maize pl1 allele. Genetics 157: 369–378.

Hollick, J. B. and Chandler, V. L. (1998). Epigenetic allelic states of a maize transcriptional regulatory locus exhibit overdominant gene action. Genetics 150: 891–897.

Hollick, J. B. and Gordon, M. P. (1993). A poplar tree proteinase inhibitor-like gene promoter is responsive to wounding in transgenic tobacco. Plant Mol. Biol. 22: 561–572.

Hollick, J. B., Dorweiler, J. E. and Chandler, V. L. (1997). Paramutation and related allelic interactions. Trends Genet. 13: 302–308.

Hollick, J. B., Patterson, G. I., Asmundsson, I. M. and Chandler, V. L. (2000). Paramutation alters regulatory control of the maize P/locus. Genetics 154: 1827–1838.

Hollick, J. B., Patterson, G. I., Coe, E. H., Jr., Cone, K. C. and Chandler, V. L. (1995). Allelic interactions heritably alter the activity of a metastable maize P/allele. Genetics 141: 709–719.

Holliday, R., Ho, T. and Paulin, R. (1996). Gene silencing in mammalian cells. In Epigenetic Mechanisms of Gene Regulation, V. E. A. Russo, R. A. Martienssen and A. D. Riggs, eds (New York: Cold Spring Harbor Laboratory Press), 47–59.

Irish, E. E., Langdale, J. A. and Nelson, T. M. (1994). Interactions between tassel seed genes and other sex determining genes in maize. Dev. Genet. 15: 155–171.

Jeddeloh, J. A., Stokes, T. L. and Richards, E. J. (1999). Maintenance of genomic methylation requires a SWI2/SNF2-like protein. Nature Genet. 22: 94–97.

Jiang, J. M., Nasuda, S., Dong, F. G., Scherrer, C. W., Woo, S. S., Wing, R. A., Gill, B. S. and Ward, D. C. (1996). A conserved repetitive DNA element located in the centromeres of cereal chromosomes. Proc. Natl. Acad. Sci. USA 93: 14210–14213.

Jorgensen, R. A. (1995). Cosuppression, flower color patterns, and metastable gene expression states. Science 268: 686–691.

Kakutani, T., Jeddeloh, J., Flowers, S. K., Munakata, K., and E. J. Richards, 1996 Developmental abnormalities and epimutations associated with DNA hypomethylation mutations. Proc. Natl. Acad. Sci. USA 93: 12406–12411.

Kakutani, T., Munakata, K., Richards, E. J. and Hirochika, H. (1999). Meiotically and mitotically stable inheritance of DNA hypomethylation induced by ddm1 mutation of *Arabidopsis thaliana*. Genetics 151: 831–838.

Kermicle, J. L., and M. Alleman, 1980. Gametic imprinting in maize in relation to the angiosperm life cycle. Development Suppl. 9–14.

Kermicle, J. L. (1996). Epigenetic silencing and activation of a maize r gene. In Epigenetic Mechanisms of Gene Regulation, V. E. A. Russo, R. A. Martienssen and A. D. Riggs, eds (New York: Cold Spring Harbor Laboratory Press), 267–287.

Kermicle, J. L., Eggleston, W. and Alleman, M. (1995). Organization of paramutagenicity in R-stippled maize. Genetics 141: 361–372.

Ketting R F, Haverkamp T H, van Luenen H G, Plasterk R H. Mut-7 of C. elegans, required for transposon silencing and RNA interference, is a homolog of Werner syndrome helicase and RNaseD. Cell. 1999 Oct. 15;99(2):133–41.

Lisch, D., Chomet, P. & Freeling, M. (1995) Genetics 139, 1777–96.

Lisch, D. & Freeling, M. (1994) Maydica 39, 289–300.

Loo, S. and Rine, J. (1995). Silencing and heritable domains of gene expression. Annu. Rev. Cell Dev. Biol. 11: 519–548.

Ludwig, W. F., Habera, L. F., Dellaporta, S. L. and Wessler, S. R. (1989). Lc, a member of the maize r gene family responsible for tissue-specific anthocyanin production, encodes a protein similar to transcriptional activators and contains the myc-homology region. Proc. Natl. Acad. Sci. USA 86: 7092–7096.

Lund, G., Das, O. P. and Messing, J. (1995). Tissue-specific DNase I-sensitive sites of the maize P gene and their changes upon epimutation. Plant J. 7: 797–807.

Martienssen, R. & Baron, A. (1994) Genetics 136, 1157–70.

Martienssen, R. A., 1996. Epigenetic silencing Mu transposable elements in maize, pp. 593–608 in Epigenetic Mechanisms of Gene Regulation, edited by V. E. A. RUSSO, R. A. MARTIENSSEN and A. D. RIGGS. Cold Spring Harbor Laboratory Press, Plainview, N.Y.

Martienssen, R. A. (1996). Paramutation and gene silencing in plants. Curr. Biol. 6: 810–813.

Matzke, A. J. M., Neuhuber, F., Park, Y.-D., Ambros, D. F. and Matzke, M. A. (1994). Homology-dependent gene silencing in transgenic plants, epistatic silencing loci contain multiple copies of methylated transgenes. Mol. Gen. Genet. 244: 219–229.

Matzke, M. A., Matzke, A. J. M. and Eggleston, W. B. (1996). Paramutation and transgene silencing: a common response to invasive DNA? Trends Plant Sci. 1: 382–388.

McClintock, B. (1957). Genetic and cytological studies of maize. Carnegie Inst. Wash. Yrbk. 56: 393–401.

McClintock, B. (1963). Further studies of gene-control systems in maize. Carnegie Inst. of Wash. Year Book 62: 486–493.

McMullen, M. D., Hunter, B., Phillips, R. L. and Rubenstein, I. (1986). The structure of the maize ribosomal DNA spacer region. Nucl. Acids Res. 14: 4953–4968.

McMullen, M. D., Phillips, R. L. and Rubenstein, I. (1991). Molecular analysis of the nucleolus organizer region in maize. In Chromosome Engineering in Plants: Genetics, Breeding and Evolution, P. K. Gupta and T. Tsuchiya, eds (New York: Elsevier Science), 561–576.

McWhirter and Brink (1962). Continuous variation in level of paramutation at the R locus in maize. Genetics 47: 1053–1074.

Meyer, P. and Saedler, H. (1996). Homology dependent gene silencing in plants. Annu. Rev. Plant Physiol. Plant Mol. Biol. 47: 23–48.

Meyer, P., Heidmann, I. and Niedenhoff, I. (1993). Differences in DNA methylation are associated with a paramutation phenomenon in transgenic petunia. Plant J. 4: 89–100.

Mikula B C. (1995) Environmental programming of heritable epigenetic changes in paramutant R-gene expression using temperature and light at a specific stage of early development in maize seedlings. Genetics. 1995 140:1379–87.

Mittelsten Scheid, O., Afsar, K. and Paszkowski, J. (1998). Release of epigenetic gene silencing by trans-acting mutations in *Arabidopsis*. Proc. Natl. Acad. Sci. USA 95: 632–637.

Morris, J. R., Chen, J.-I., Filandrinos, S. T., Dunn, R. C., Fisk, R., Geyer, P. K. and Wu, C.-t. (1999). An analysis of transvection at the yellow locus of *Drosophila melanogaster*. Genetics 151: 633–651.

Mourrain, P., Beclin, C., Elmayan, T., Feuerbach, F., Godon, C., et al., 2000 *Arabidopsis* SGS2 and SGS3 genes are required for posttranscriptional gene silencing and natural virus resistance. Cell 101: 533–542.

Neal (1998). Characterization of the organization and paramutagenicity of the maize R-marbled allele. M. S. Dissertation, Virginia Commonwealth University, Richmond, Va., U.S.A.

Neuffer, M. G., 1978 Induction of genetic variability, pp. 579–600, in Maize Breeding and Genetics, edited by D. B. Walden. John Wiley & Sons, New York.

Neuffer, M. G., and E. H. Coe Jr., 1978. Paraffin oil technique for treating mature corn pollen with chemical mutagens. Maydica 23: 21–28.

Ogas, J., Kaurmann, S., Henderson, J. and Somerville, C. (1999). PICKLE is a CHD3 chromatin-remodeling factor that regulates the transition from embryonic to vegetative development in *Arabidopsis*. Proc. Natl. Acad. Sci. USA 96: 13839–13844.

O'Reilly, C., Shepherd, N. S., Pereira, A., Schwarz-Sommer, Z., Bertram, I., Robertson, D. S., Peterson, P. A. & Saedler, H. (1985) Embo J. 4, 591–597.

PaI-Bhadra, M., Bhadra, U., and J. A. Birchler, 1997. Cosuppression in *Drosophila*: Gene silencing of Alcohol dehydrogenase by white-Adh transgenes is Polycomb dependent. Cell 90: 479–490.

Panavas T, Weir J, Walker E L 1999 The structure and paramutagenicity of the R-marbled haplotype of *Zea mays*. Genetics 153(2): 979–91.

Patterson, G. I., Harris, L. J., Walbot, V. and Chandler, V. L. (1991). Genetic Analysis of B-Peru, a regulatory gene in maize. Genetics 126: 205–220.

Patterson, G. I., Kubo, K. M., Shroyer, T. and Chandler, V. L. (1995). Sequences required for paramutation of the maize b gene map to a region containing the promoter and upstream sequences. Genetics 140: 1389–1406.

Patterson, G. I., Thorpe, C. J. and Chandler, V. L. (1993). Paramutation, an allelic interaction, is associated with a stable and heritable reduction of transcription of the maize b regulatory gene. Genetics 135: 881–894.

Paul, A.-L., Vasil, V., Vasil, I. K. and Ferl, R. J. (1987). Constitutive and anaerobically induced DNase-l-hypersensitive sites in the 5' region of the maize Adh1 gene. Proc. Natl. Acad. Sci. USA 84: 799–803.

Pirrotta, V. (1998). Polycombing the genome: PcG, trxG, and chromatin silencing. Cell 93: 333–336.

Quinn (1999). Characterization of the transposable element responsible for germinal and somatic instability of the maize R-marbled allele. M. S. Dissertation, Virginia Commonwealth University, Richmond, Va., U.S.A.

Radicella, J. P., Brown, D., Tolar, L. A. and Chandler, V. L. (1992). Allelic diversity of the maize b regulatory gene: different leader and promoter sequences of two b alleles determine distinct tissue specificities of anthocyanin production. Genes and Development 6: 2152–2164.

Radicella, J. P., Turks, D. and Chandler, V. L. (1991). Cloning and nucleotide sequence of a cDNA encoding B-Peru, a regulatory protein of the anthocyanin pathway in maize. Plant Mol. Biol. 17: 127–130.

Robbins, T. P., Walker, E. L., Kermicle, J. L., Alleman, M., and Dellaporta, S. L. 1991. Meiotic instability of the R-r complex arising from displaced intragenic exchange and intrachromosomal rearrangement. Genetics 129: 217–283.

Ronchi, A., Petroni, K., and C. Tonelli, 1995. The reduced expression of endogenous duplications (REED) in the maize R gene family is mediated by DNA methylation. EMBO J. 14: 5318–5328.

Ronemus, M. J., Galbiati, M., Ticknor, C., Chen, J., and S. L. Dellaporta, 1996. Demethylation-induced developmental pleiotropy in *Arabidopsis*. Science 273: 654–657.

Ronsseray, S., M. Lehmann, D. Nouaud, and D. Anxolabehere, 1996. The regulatory properties of autonomous subtelomeric P elements are sensitive to a Suppressor of variegation in *Drosophila melanogaster*. Genetics 143:1663–1674.

Sass, G. L. and Henikoff, S. (1998). Comparative analysis of Position-Effect Variegation mutations in *Drosophila melanogaster* delineates the targets of modifiers. Genetics 148: 733–741.

Sastry, G. R. K., Cooper, H. B., Jr., and Brink, R. A. 1965. Paramutation and somatic mosaicism in maize. Genetics 52: 407–424.

Selinger, D. A. and Chandler, V. L. (1999). A mutation in the pale aleurone color1 gene identifies a novel regulator of the maize anthocyanin pathway. Plant Cell 11: 5–14.

Selinger, D. A. and Chandler, V. L. (2001) B-Bolivia, an allele of the maize b1 gene with variable expression, contains a high copy retrotransposon-related sequence immediately upstream. Plant Physiol. 125:1363–79.

Selinger D A, Lisch D, Chandler V L. (1999) The maize regulatory gene B-Peru contains a DNA rearrangement that specifies tissue-specific expression through both positive and negative promoter elements. Genetics. 149:1125–38.

Sherman, J. M. and Pillus, L. (1997). An uncertain silence. Trends Genet. 13: 308 313.

Shih, K. L. and Brink, R. A. 1969. Effects of X-irradiation on aleurone pigmenting potential of standard Rr and a paramutant form of Rr in maize. Genetics 61: 167–177.

Spiker, S., Murray, M. G. and Thompson, W. F. (1983). DNase I sensitivity of transcriptionally active genes in intact nuclei and isolated chromatin of plants. Proc. Natl. Acad. Sci. USA 80: 815–819.

Steinmuller, K. and Apel, K. (1986). A simple and efficient procedure for isolating plant chromatin which is suitable for studies of DNase I-sensitive domains and hypersensitive sites. Plant Mol. Biol. 7: 87–94.

Styles, E. D., and E. H. Coe Jr., 1986. Unstable expression of an R allele with a3 in maize. J. Hered. 77: 389–393.

Styles, E. D. and Brink, R. A. (1968). The metastable nature of paramutable R alleles in maize. IV. Parallel enhancement of R action in heterozygotes with r and in hemizygotes. Genetics 61: 801–811.

Styles, E. D., Ceska, 0. and Seah, K.-T. (1973). Developmental differences in action of r and b alleles in maize. Can. J. Genet. Cytol. 15: 59–72.

Tabara H, Sarkissian M, Kelly W G, Fleenor J, Grishok A, Timmons L, FireA, Mello C C. The rde-1 gene, RNA interference, and transposon silencing in C. elegans. Cell. 1999 Oct. 15, 1999(2):123–32.

Talbert, L. E., Patterson, G. I. & Chandler, V. L. (1989) J Mol Evol 29, 28–39.

Todd, J. J., and L. O. Vodkin, 1996. Duplications that suppress and deletions that restore expression from a chalcone synthase multigene family. Plant Cell 8: 687–699.

Vielle-Calzada, J. P., Baskar, R., and U. Grossniklaus, 2000 Delayed activation of the paternal genome during seed development. Nature 404: 91–94.

Vongs, A., Kakutani, T., Martienssen, R. and Richards, E. J. (1993). *Arabidopsis thaliana* DNA methylation mutants. Science 260: 1926–1928.

Wakimoto, B. T. (1998). Beyond the nucleosome: epigenetic aspects of position-effect variegation in *Drosophila*. Cell 93: 321–324.

Walker E L, Robbins T P, Bureau T E, Kermicle J, Dellaporta S L. (1995) Transposon-mediated chromosomal rearrangements and gene duplications in the formation of the maize R-r complex. EMBO J. 14:2350–63.

Walker, E. (1998). Paramutation of the r1 locus of maize is associated with increased cytosine methylation. Genetics 148: 1973–1981.

Wallrath, L. (1998). Unfolding the mysteries of heterochromatin. Curr. Opin. Genet. Dev. 8:147–153.

Watson, J. C. and Thompson, W. F. (1986). Purification and restriction endonuclease analysis of plant nuclear DNA. Methods Enzymol. 118: 57–75.

Weiler, K. S., and B. T. Wakimoto, 1995. Heterochromatin and gene expression in *Drosophila.* Annu. Rev. Genetics 29: 577–605.

Wienand, U., Weydemann, U., Niesbach-Klosgen, U., Peterson, P. A. and Saedler, H. (1986). Molecular-cloning of the c2 locus of *Zea mays,* the gene coding for chalcone synthase. Mol. Gen. Genet. 203: 202–207.

What is claimed is:

1. A mutant mop1-1, Mop2-1, rmr1-1, or rmr2-1 corn plant comprising a transgene, wherein the transgene is hypomethylated compared to the methylation state of the transgene in a non-mutant transgenic corn plant and the expression of said transgene is at least two-fold higher as compared to the expression of the transgene in said non-mutant transgenic corn plant.

2. Seed from the mutant, transgenic corn plant of claim 1, wherein said seed comprises the transgene, wherein the transgene is hypomethylated and the expression of said transgene is at least two-fold higher as compared to the expression of the transgene in said non-mutant transgenic corn seed.

3. Seed produced by crossing the mutant transgenic plant of claim 1 and another plant or by self-pollinating the mutant, transgenic corn plant of claim 1, wherein said seed comprises the transgene, wherein the transgene is hypomethylated and the expression of said transgene is at least two-fold higher as compared to the expression of the transgene in said non-mutant transgenic corn seed.

4. A tissue culture of regenerable cells of the plant of claim 1.

5. The mutant, transgenic corn plant of claim 1 wherein the higher expression of the transgene is detectable by RNA analytical measurements.

6. A corn seed genotypically designated rmr2-1 having ATCC Accession Number PTA-3956, further comprising a transgene wherein the transgene is hypomethylated compared to the methylation state of the transgene in a non-mutant corn seed and the expression of said transgene is at least two-fold higher as compared to the expression of the transgene in said non-mutant corn seed.

7. A corn plant produced from the seed of claim 6.

8. Pollen or an ovule of the plant of claim 7.

9. A population of corn plants produced by growing the seed of the corn plant of claim 7.

10. Progeny seed comprising the rmr2-1 mutation produced from crossing the plant of claim 7 with another corn plant or by self-pollinating the plant of claim 7, wherein said seed further comprises the transgene, wherein the transgene is hypomethylated and the expression of said transgene is at least two-fold higher as compared to the expression of the transgene in said non-mutant corn seed.

11. A corn plant comprising the rmr2-1 mutation produced from the seed of claim 10, wherein said plant further comprises the transgene, wherein the transgene is hypomethylated and the expression of said transgene is at least two-fold higher as compared to the expression of the transgene in said non-mutant corn plant.

12. A tissue culture of regenerable cells comprising the rmr2-1 mutation of corn plant genotypically designated rmr2-1, wherein the tissue culture can regenerate into a plant having all the physiological and morphological characteristics of the corn plant rmr2-1, a sample of the seed of said corn plant rmr2-1 having been deposited under ATCC Accession Number PTA-3956, and wherein the cells further comprise a transgene, wherein the transgene is hypomethylated and the expression of said transgene is at least two-fold higher as compared to the expression of the transgene in non-mutant corn cells.

13. The tissue culture of claim 12, wherein the regenerable cells comprise cells derived from embryos, immature embryos, meristematic cells, immature tassels, microspores, pollen, leaves, anthers, roots, root tips, silk, flowers, kernels, ears, cobs, husks, or stalks.

14. The tissue culture of claim 13, wherein the regenerable cells comprise protoplasts or callus.

15. A corn plant regenerated from the tissue culture of claim 12, wherein said corn plant has all of the genotypic, physiological and morphological characteristics of the corn plant designated rmr2-1, and comprises said hypomethylated transgene.

16. A process of producing corn seed comprising the rmr2-1 mutation, comprising self-pollinating a plant genotypically designated rmr2-1 and further comprising a transgene or crossing a first parent corn plant with a second parent corn plant, wherein said first or second corn plant is the corn plant designated rmr2-1 and further comprising the transgene, a sample of the seed of said corn plant designated rmr2-1 having been deposited under ATCC Accession No. PTA-3956, wherein said seed comprising the rmr2-1 mutation produced from the cross comprises the transgene, wherein the transgene is hypomethylated compared to the methylation state of the transgene in a non-mutant corn seed and the expression of said transgene is at least two-fold higher as compared to the expression of the transgene in said non-mutant corn seed.

17. The process of claim 16, wherein crossing comprises the steps of:
    (a) planting in pollinating proximity seeds of said first and second corn plants;
    (b) cultivating the seeds of said first and second corn plants into plants that bear flowers;
    (c) emasculating the male flowers of said first or second corn plant to produce an emasculated corn plant;
    (d) allowing cross-pollination to occur between said first and second corn plants; and
    (e) harvesting seeds produced on said emasculated corn plant.

18. The process of claim 17, further comprising growing said harvested seed to produce a hybrid corn plant.

19. A corn seed genotypically designated Mop2-1 having ATCC Accession Number PTA-4030, further comprising a transgene wherein the transgene is hypomethylated compared to the methylation state of the transgene in a non-mutant corn seed and the expression of said transgene is at least two-fold higher as compared to the expression of the transgene in said non-mutant corn seed.

20. A corn plant produced from the seed of claim 19.

21. Pollen or an ovule of the plant of claim 20.

22. A population of corn plants produced by growing the seed of the corn plant of claim 20.

23. Progeny seed comprising the Mop2-1 mutation produced from crossing the plant of claim 20 with another corn plant or by self-pollinating the plant of claim 20, wherein said seed further comprises the transgene, wherein the transgene is hypomethylated and the expression of said transgene is at least two-fold higher as compared to the expression of the transgene in said non-mutant corn seed.

24. A corn plant comprising the Mop2-1 mutation produced from the seed of claim 23, wherein said plant further comprises the transgene, wherein the transgene is hypomethylated and the expression of said transgene is at least two-fold higher as compared to the expression of the transgene in said non-mutant corn plant.

25. A tissue culture of regenerable cells comprising the Mop2-1 mutation of a corn plant genotypically designated Mop2-1, wherein the tissue culture can regenerate into a plant having all the physiological and morphological characteristics of the corn plant Mop2-1, a sample of the seed of said corn plant Mop2-1 having been deposited under ATCC Accession Number PTA-4030, and wherein the cells further comprise a transgene, wherein the transgene is hypomethylated and the expression of said transgene is at least two-fold higher as compared to the expression of the transgene in non-mutant corn cells.

26. The tissue culture of claim 25, wherein the regenerable cells comprise cells derived from embryos, immature embryos, meristematic cells, immature tassels, microspores, pollen, leaves, anthers, roots, root tips, silk, flowers, kernels, ears, cobs, husks, or stalks.

27. The tissue culture of claim 26, wherein the regenerable cells comprise protoplasts or callus.

28. A corn plant regenerated from the tissue culture of claim 25, wherein said corn plant has all of the genotypic, physiological and morphological characteristics of the corn plant designated Mop2-1, and comprises said hypomethylated transgene.

29. A process of producing corn seed comprising the Mop2-1 mutation, comprising self-pollinating a plant genotypically designated Mop2-1 and further comprising a transgene or crossing a first parent corn plant with a second parent corn plant, wherein said first or second corn plant is the corn plant designated Mop2-1, and further comprising a transgene, a sample of the seed of said corn plant designated Mop2-1 having been deposited under ATCC Accession No. PTA-4030, wherein said seed comprising the Mop2-1 mutation produced from the cross comprises the transgene, wherein the transgene is hypomethylated compared to the methylation state of the transgene in a non-mutant corn seed and the expression of said transgene is at least two-fold higher as compared to the expression of the transgene in said non-mutant corn seed.

30. The process of claim 29, wherein crossing comprises the steps of:
  (a) planting in pollinating proximity seeds of said first and second corn plants;
  (b) cultivating the seeds of said first and second corn plants into plants that bear flowers;
  (c) emasculating the male flowers of said first or second corn plant to produce an emasculated corn plant;
  (d) allowing cross-pollination to occur between said first and second corn plants; and
  (e) harvesting seeds produced on said emasculated corn plant.

31. The process of claim 30, further comprising growing said harvested seed to produce a hybrid corn plant.

32. A corn seed genotypically designated rmr1-1 having ATCC Accession Number PTA-3965, further comprising a transgene wherein the transgene is hypomethylated compared to the methylation state of the transgene in a non-mutant corn seed and the expression of said transgene is at least two-fold higher as compared to the expression of the transgene in said non-mutant corn seed.

33. A corn plant produced from the seed of claim 32.

34. Pollen or an ovule of the plant of claim 33.

35. A population of corn plants produced by growing the seed of the corn plant of claim 33.

36. Progeny seed comprising the rmr1-1 mutation produced from crossing the plant of claim 33 with another corn plant or by self-pollinating the plant of claim 33, wherein said seed further comprises the transgene, wherein the transgene is hypomethylated and the expression of said transgene is at least two-fold higher as compared to the expression of the transgene in said non-mutant corn seed.

37. A corn plant comprising the rmr1-1 mutation produced from the seed of claim 36, wherein said plant further comprises the transgene, wherein the transgene is hypomethylated and the expression of said transgene is at least two-fold higher as compared to the expression of the transgene in said non-mutant corn plant.

38. A tissue culture of regenerable cells comprising the rmr1-1 mutation of corn plant genotypically designated rmr1-1, wherein the tissue culture can regenerate into a plant having all the physiological and morphological characteristics of the corn plant rmr1-1, a sample of the seed of said corn plant rmr1-1 having been deposited under ATCC Accession Number PTA-3965, and wherein the cells further comprise a transgene, wherein the transgene is hypomethylated and the expression of said transgene is at least two-fold higher as compared to the expression of the transgene in non-mutant corn cells.

39. The tissue culture of claim 38, wherein the regenerable cells comprise cells derived from embryos, immature embryos, meristematic cells, immature tassels, microspores, pollen, leaves, anthers, roots, root tips, silk, flowers, kernels, ears, cobs, husks, or stalks.

40. The tissue culture of claim 39, wherein the regenerable cells comprise protoplasts or callus.

41. A corn plant regenerated from the tissue culture of claim 38, wherein said corn plant has all of the genotypic, physiological and morphological characteristics of the corn plant designated rmr1-1, and comprises said hypomethylated transgene.

42. A process of producing corn seed comprising the rmr1-1 mutation, comprising self-pollinating a plant genotypically designated rmr1-1 and further comprising a transgene or crossing a first parent corn plant with a second parent corn plant, wherein said first or second corn plant is the corn plant rmr1-1, and further comprising a transgene, a sample of the seed of said corn plant rmr1-1 having been deposited under ATCC Accession No. PTA-3965, wherein said seed comprising the rmr1-1 mutation produced from the cross comprises the transgene, wherein the transgene is hypomethylate compared to the methylation state of the transgene in a non-mutant corn seed and the expression of said transgene is at least two-fold higher as compared to the expression of the transgene in said non-mutant corn seed.

43. The process of claim 42, wherein crossing comprises the steps of:
  (a) planting in pollinating proximity seeds of said first and second corn plants;
  (b) cultivating the seeds of said first and second corn plants into plants that bear flowers;
  (c) emasculating the male flowers of said first or second corn plant to produce an emasculated corn plant;
  (d) allowing cross-pollination to occur between said first and second corn plants; and
  (e) harvesting seeds produced on said emasculated corn plant.

44. The process of claim 43, further comprising growing said harvested seed to produce a hybrid corn plant.

45. A corn seed genotypically designated mop1-1 having ATCC Accession Number PTA3828, further comprising a transgene wherein the transgene is hypomethylated compared to the methylation state of the transgene in a non-mutant corn seed and the expression of said transgene is at least two-fold higher as compared to the expression of the transgene in said non-mutant corn seed.

46. A corn plant produced from the seed of claim 45.

47. Pollen or an ovule of the plant of claim 46.

48. A population of corn plants produced by growing the seed of the corn plant of claim 46.

49. Progeny seed comprising the mop1-1 mutation produced from crossing the plant of claim 46 with another corn plant or by self-pollinating the plant of claim 46, wherein said seed further comprises the transgene, wherein the transgene is hypomethylated and the expression of said transgene is at least two-fold higher as compared to the expression of the transgene in said non-mutant corn seed.

50. A corn plant comprising the mop1-1 mutation produced from the seed of claim 49, wherein said plant further comprises the transgene, wherein the transgene is hypomethylated and the expression of said transgene is at least two-fold higher as compared to the expression of the transgene in said non-mutant corn plant.

51. A tissue culture of regenerable cells comprising the mop1-1 mutation of corn plant genotypically designated mop1-1, wherein the tissue culture can regenerate into a plant having all the physiological and morphological characteristics of the corn plant mop1-1, a sample of the seed of said corn plant mop1-1 having ATCC Accession Number PTA3828 and wherein the cells further comprise a transgene, wherein the transgene is hypomethylated and the expression of said transgene is at least two-fold higher as compared to the expression of the transgene in non-mutant corn cells.

52. The tissue culture of claim 51, wherein the regenerable cells comprise cells derived from embryos, immature embryos, meristematic cells, immature tassels, microspores, pollen, leaves, anthers, roots, root tips, silk, flowers, kernels, ears, cobs, husks, or stalks.

53. The tissue culture of claim 52, wherein the regenerable cells comprise protoplasts or callus.

54. A corn plant regenerated from the tissue culture of claim 51, wherein said corn plant has all of the physiological and morphological characteristics of the corn plant designated mop1-1, and comprises said hypomethylated transgene.

55. A process of producing corn seed comprising the mop1-1 mutation, comprising self-pollinating a plant genotypically designated mop1-1 and further comprising a transgene or crossing a first parent corn plant with a second parent corn plant, wherein said first or second corn plant is the corn plant designated mop1-1 and further comprising the transgene, a sample of the seed of said corn plant designated mop1-1 having been deposited under ATCC Accession No. PTA3828, wherein said seed comprising the mop1-1 mutation produced from the cross comprises the transgene, wherein the transgene is hypomethylated compared to the methylation state of the transgene in a non-mutant corn seed and the expression of said transgene is at least two-fold higher as compared to the expression of the transgene in said non-mutant corn seed.

56. The process of claim 55, wherein crossing comprises the steps of:
(a) planting in pollinating proximity seeds of said first and second corn plants;
(b) cultivating the seeds of said first and second corn plants into plants that bear flowers;
(c) emasculating the male flowers of said first or second corn plant to produce an emasculated corn plant;
(d) allowing cross-pollination to occur between said first and second corn plants; and
(e) harvesting seeds produced on said emasculated corn plant.

57. The process of claim 56, further comprising growing said harvested seed to produce a hybrid corn plant.

* * * * *